US011473104B2

(12) United States Patent
Krom et al.

(10) Patent No.: US 11,473,104 B2
(45) Date of Patent: Oct. 18, 2022

(54) ENGINEERED PHAGEMIDS

(71) Applicants: Massachusetts Institute of Technology, Cambridge, MA (US); Trustees of Boston University, Boston, MA (US); President and Fellows of Harvard College, Cambridge, MA (US)

(72) Inventors: Russell-John Krom, Boston, MA (US); James J. Collins, Newton, MA (US); Prerna Saluja Bhargava, Watertown, MA (US); Michael Andrew Lobritz, Newton, MA (US)

(73) Assignees: Massachusetts Institute of Technology, Cambridge, MA (US); Trustees of Boston University, Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/780,668

(22) PCT Filed: Dec. 4, 2015

(86) PCT No.: PCT/US2015/064020
§ 371 (c)(1),
(2) Date: Jun. 1, 2018

(87) PCT Pub. No.: WO2017/095440
PCT Pub. Date: Jun. 8, 2017

(65) Prior Publication Data
US 2018/0355378 A1 Dec. 13, 2018

(51) Int. Cl.
| | | |
|---|---|---|
| *C12N 15/86* | (2006.01) | |
| *A61K 35/76* | (2015.01) | |
| *C07K 14/245* | (2006.01) | |
| *C07K 14/35* | (2006.01) | |
| *C12N 15/63* | (2006.01) | |
| *C12N 15/70* | (2006.01) | |
| *C12N 15/74* | (2006.01) | |
| *C07K 14/46* | (2006.01) | |
| *C07K 14/435* | (2006.01) | |
| *C07K 14/61* | (2006.01) | |

(52) U.S. Cl.
CPC ............ *C12N 15/86* (2013.01); *A61K 35/76* (2013.01); *C07K 14/245* (2013.01); *C07K 14/43572* (2013.01); *C07K 14/461* (2013.01); *C07K 14/463* (2013.01); *C12N 15/63* (2013.01); *C12N 15/70* (2013.01); *C12N 15/74* (2013.01); *C12N 2795/14132* (2013.01); *C12N 2795/14143* (2013.01)

(58) Field of Classification Search
None
See application file for complete search history.

(56) References Cited

U.S. PATENT DOCUMENTS

| | | | |
|---|---|---|---|
| 2003/0113293 A1* | 6/2003 | Bermudes | A61K 48/00 424/93.2 |
| 2003/0147852 A1 | 8/2003 | Schaak | |
| 2015/0004705 A1 | 1/2015 | Lu et al. | |

FOREIGN PATENT DOCUMENTS

| | | | |
|---|---|---|---|
| WO | WO 2010/141135 A2 | 12/2010 | |
| WO | WO 2013/148321 A1 | 10/2013 | |
| WO | WO 2014/124226 A1 | 8/2014 | |

OTHER PUBLICATIONS

Couturier et al., Trends In Microbiology, 1998, 6(7):269-275. (Year: 1998).*
Lu et al., PNAS, Mar. 24, 2009, 106(12): 4629-4634. (Year: 2009).*
Boman et al., Mechanisms of action on *Escherichia coli* of cecropin P1 and PR-39, two antibacterial peptides from pig intestine. Infection and Immunity. 1993;61(7):2978-84.
Brogden et al., Antimicrobial peptides: pore formers or metabolic inhibitors in bacteria? Nat Rev Microbiol. Mar. 2005;3(3):238-50.
Chasteen et al., Eliminating helper phage from phage display. Nucleic Acids Research. 2006;34(21):e145, 11 pages. Epub Nov. 6, 2006.
Citorik et al., Bacteriophage-based synthetic biology for the study of infectious diseases. Curr Opinions in Microbiology. 2014;19:59-69. Epub Jul. 3, 2014.
Cole et al., Isolation and Characterization of Pleurocidin, an Antimicrobial Peptide in the Skin Secretions of Winter Flounder. J Biol Chem. Jun. 1997;272(18):12008-13. doi: 10.1074/jbc.272.18.12008.
Jouenne et al., Antibacterial activity of synthetic dermaseptins against growing and nongrowing *Escherichia coli* cultures. J Antimicrob Chemother. Jul. 1998;42(1):87-90.
Krom et al., Engineered phagemids for nonlytic, targeted antibacterial therapies. Nano Lett. 2015;15:4808-13. doi: 10.1021/acs.nanolett.5b01943.
Li et al., Apidaecin-type peptides: biodiversity, structure-function relationships and mode of action. Peptides. Sep. 2006;27(9):2350-9. Epub May 3, 2006.
Litcofsky et al., Iterative plug-and-play methodology for constructing and modifying synthetic gene networks. Nat Methods. Nov. 2012;9(11):1077-80. doi: 10.1038/nmeth.2205. Epub Oct. 7, 2012.
Park et al., Structure-activity analysis of buforin II, a histone H2A-derived antimicrobial peptide: The proline hinge is responsible for the cell-penetrating ability of buforin II. PNAS. Jul. 18, 2000;97(15):8245-50.

(Continued)

*Primary Examiner* — Nicole Kinsey White
(74) *Attorney, Agent, or Firm* — Wolf, Greenfield & Sacks, P.C.

(57) ABSTRACT

Provided herein, in some embodiments, are engineered phagemids that comprise at least one synthetic genetic circuit, wherein the at least one synthetic genetic circuit comprises gene sequences encoding at least one non-lytic antimicrobial peptides (AMPs) and/or antibacterial toxin proteins, a stable origin of replication, and a bacteriophage-packaging signal, wherein the engineered phagemid does not comprise some or all gene sequences encoding bacteriophage proteins required for assembly of a bacteriophage particle.

18 Claims, 7 Drawing Sheets

Specification includes a Sequence Listing.

(56) References Cited

OTHER PUBLICATIONS

Russel et al., Genetic analysis of the filamentous bacteriophage packaging signal and of the proteins that interact with it. J Virol. Aug. 1989;63(8):3284-95.
Westwater et al., Use of genetically engineered phage to deliver antimicrobial agents to bacteria: an alternative therapy for treatment of bacterial infections. Antimicrob Agents Chemother. Apr. 2003;47(4):1301-7. doi: 10.1128/AAC.47.4.1301-1307.2003.
Krom et al., Targeted Antibacterial Therapies. Nano Lett. Jul. 8, 2015;15(7):4808-13. doi: 10.1021/acs.nanolett.5b01943. Epub Jun. 8, 2015.
PCT/US2015/064020, dated Jun. 14, 2018, International Preliminary Report on Patentability.
PCT/US2015/064020, dated Feb. 8, 2016, International Search Report and Written Opinion.
EP 15909953.0, dated Mar. 21, 2019, Extended European Search Report.

* cited by examiner

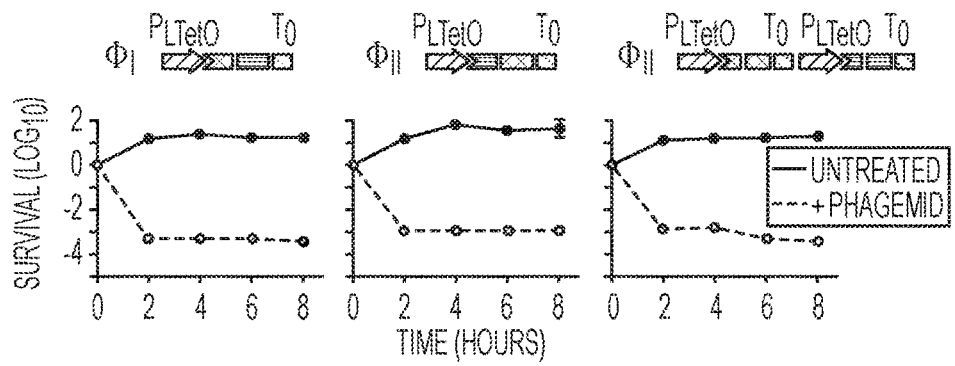
FIG. 4A
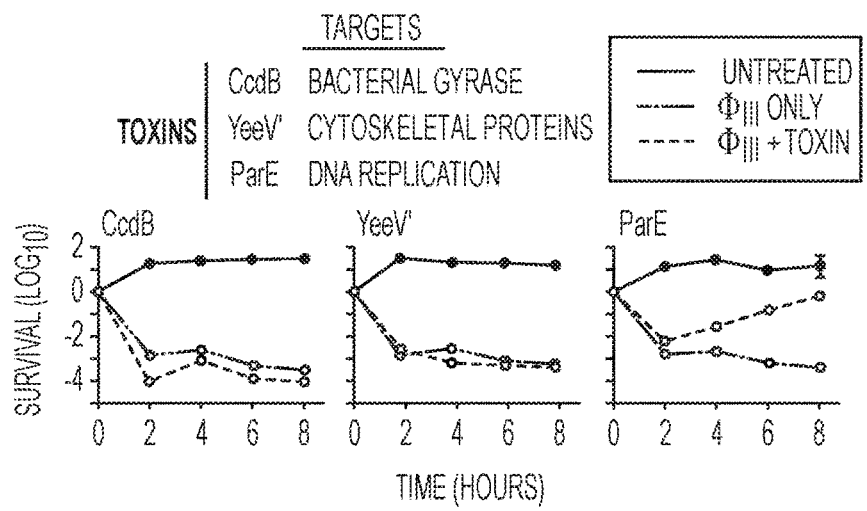
FIG. 4B
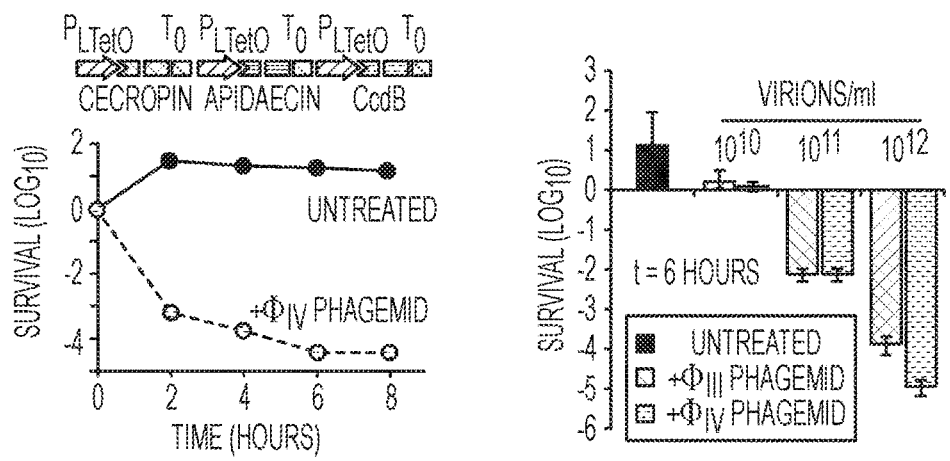
FIG. 4C
FIG. 4D

SEQUENCE LISTING

<160> NUMBER OF SEQ ID NOS: 67

<210> SEQ ID NO 1
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 1
gcccgcaagc tttccctatc agtgatagag attgaca                                    37

<210> SEQ ID NO 2
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 2
atttttggta ccggtcagtg cgtcctgctg atgtgct                                    37

<210> SEQ ID NO 3
<211> LENGTH: 37
<212> TYPE: DNA
<213> ORGANISM: Artificial Sequence

```
<220> FEATURE:
<223> OTHER INFORMATION: Synthetic Polynucleotide

<400> SEQUENCE: 3
tatttaggat cccgagaatt ggcttggact cctgttg                              37

<210> SEQ ID NO 4
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 4
gattatgagc tctgactact gcttggattc tcaccaa                              37

<210> SEQ ID NO 5
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 5
tatttactcg agagcgccct gtagcggcgc att                                  33

<210> SEQ ID NO 6
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 6
ggcgcgaata tttaattcgc gttaaatttt tgttaaatca gctcattttt taaccaatag     60

<210> SEQ ID NO 7
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 7
aatttaggta ccctataagt tacacaacat aaggaggaat ataatgcgtc gtcgtccgcg     60
tcc                                                                   63

<210> SEQ ID NO 8
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 8
agaattccgc ggttacggga aacgcggcgg gaaacgc                              37

<210> SEQ ID NO 9
<211> LENGTH: 62
<212> TYPE: DNA
<213> ORGANISM: Artificial Sequence
<220> FEATURE:
<223> OTHER INFORMATION: Synthetic Polynucleotide

<400> SEQUENCE: 9
```

```
atttattgta cattctatca aagtatcata aggaggagaa taatgcgtcg tcgtccgcgt      60
cc                                                                    62
```

<210> SEQ ID NO 10
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 10

```
gaggtcggat ccttacggga acgcggcgg gaaacgc                               37
```

<210> SEQ ID NO 11
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 11

```
atttatggta cccaacaggg attcgttaat ttaaggaggt ctccaaatgg gcaacaaccg      60
```

<210> SEQ ID NO 12
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 12

```
atttatccgc ggttaaatgc gcggatgcgg cg                                   32
```

<210> SEQ ID NO 13
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 13

```
attgcgtgta cagaggtaca actcaactaa tataaggagg ttcaaaatgg gcaacaaccg      60
```

<210> SEQ ID NO 14
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 14

```
atcgcgggat ccttaaatgc gcggatgcgg cg                                   32
```

<210> SEQ ID NO 15
<211> LENGTH: 57
<212> TYPE: DNA
<213> ORGANISM: Artificial Sequence
<220> FEATURE:
<223> OTHER INFORMATION: Synthetic Polynucleotide

<400> SEQUENCE: 15

```
atttttggta cccgactaac aactctataa ggaggtccat aaatgacccg cagcagc         57
```

<210> SEQ ID NO 16
<211> LENGTH: 32

```
<212> TYPE: DNA
<213> ORGANISM: Artificial Sequence
<220> FEATURE:
<223> OTHER INFORMATION: Synthetic Polynucleotide

<400> SEQUENCE: 16
attgccccgc ggttatttgc gcagcaggcg at                              32

<210> SEQ ID NO 17
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 17
atttattgta cagaggtaca actcaactaa tataaggagg ttcaaaatga cccgcagcag    60

<210> SEQ ID NO 18
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 18
gcgcccggat ccttatttgc gcagcaggcg at                              32

<210> SEQ ID NO 19
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 19
atttatggta cctaaaagag gagactcacc cttaaggagg tataagatgg cgctgtggaa    60

<210> SEQ ID NO 20
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 20 attccccgc ggttagcttt ccgcgcccac ca                               32

<210> SEQ ID NO 21
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 21
atttattgta cacaagtaca gaggagtaag gaggtaaagt atggcgctgt ggaaaaacat    60

<210> SEQ ID NO 22
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 22
```
cctgcgggat ccttagcttt ccgcgcccac ca                                32

<210> SEQ ID NO 23
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 23
atttatggta ccaacggtaa gaggcataat ttaaggaggt aacacatggg ctggggcag    59

<210> SEQ ID NO 24
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 24
cgccgcccgc ggttacagat aatgggtcag cg                                32

<210> SEQ ID NO 25
<211> LENGTH: 60
<212> TYPE: DNA
<213> ORGANISM: Artificial Sequence
<220> FEATURE:
<223> OTHER INFORMATION: Synthetic Polynucleotide

<400> SEQUENCE: 25
attgtttgta cagatttata aaatcggaat agataaggag gtacacatgg gctggggcag   60

<210> SEQ ID NO 26
<211> LENGTH: 32
<212> TYPE: DNA
<213> ORGANISM: Artificial Sequence
<220> FEATURE:
<223> OTHER INFORMATION: Synthetic Polynucleotide

<400> SEQUENCE: 26
cgccgcggat ccttacagat aatgggtcag cg                                32

<210> SEQ ID NO 27
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 27
aatcatctgc agtccctatc agtgatagag attgacatcc ct                     42

<210> SEQ ID NO 28
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 28
ggcccggaat tctgactact gcttggattc tcaccaataa aa                     42

<210> SEQ ID NO 29
<211> LENGTH: 63
<212> TYPE: DNA
<213> ORGANISM: Artificial Sequence

```
<220> FEATURE:
<223> OTHER INFORMATION: Synthetic Polynucleotide

<400> SEQUENCE: 29
tataatggta cccagggagg gaaagtcaat aaggacggat attatgaaag cgttaacggc    60
cag                                                                 63

<210> SEQ ID NO 30
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 30
ccggccggat ccttacagcc agtcgccgtt gcgaata                             37

<210> SEQ ID NO 31
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 31
atttatccgc gggcctacta gaaactaata aggagactac cgagaatgga aaagaaatta    60
ccc                                                                 63

<210> SEQ ID NO 32
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 32
atttatggat ccttagtttt gttcatcttc cagcaagcgt gcgccgg                  47

<210> SEQ ID NO 33
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 33
atttatggta cctatccatc attaacgacc aaatcaagga ggacgtatgc agtttaaggt    60
ttacac                                                              66

<210> SEQ ID NO 34
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 34
ggccgcggat ccttatattc cccagaacat caggttaatg gcgtttt                  47

<210> SEQ ID NO 35
<211> LENGTH: 64
<212> TYPE: DNA
<213> ORGANISM: Artificial Sequence
<220> FEATURE:
```

<223> OTHER INFORMATION: Synthetic Polynucleotide

<400> SEQUENCE: 35
atttatggta ccgccccaac gaacaatatt actaaggagg aaagatatgc tgattctgac    60
tcgt    64

<210> SEQ ID NO 36
<211> LENGTH: 49
<212> TYPE: DNA
<213> ORGANISM: Artificial Sequence
<220> FEATURE:
<223> OTHER INFORMATION: Synthetic Polynucleotide

<400> SEQUENCE: 36
ggcattggat ccttagtaac tggactgctg ggatttttca gcctggata    49

<210> SEQ ID NO 37
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 37
attggcctta agtccctatc agtgatagag attgacatcc    40

<210> SEQ ID NO 38
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 38 atttcccta ggtgactact gcttggattc tcaccaataa    40

<210> SEQ ID NO 39
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 39
atttttggcg cctgactact gcttggattc tcaccaataa    40

<210> SEQ ID NO 40
<211> LENGTH: 40
<212> TYPE: DNA
<213> ORGANISM: Artificial Sequence
<220> FEATURE:
<223> OTHER INFORMATION: Synthetic Polynucleotide

<400> SEQUENCE: 40
attcagcaat tgtgactact gcttggattc tcaccaataa    40

<210> SEQ ID NO 41
<211> LENGTH: 68
<212> TYPE: DNA
<213> ORGANISM: Artificial Sequence
<220> FEATURE:
<223> OTHER INFORMATION: Synthetic Polynucleotide

<400> SEQUENCE: 41
tatattggta cccaagaaga tagaggaggt aatatacaag agaatgaaca ccctgccgga    60

```
                                              -continued tacccatg                                                            68

<210> SEQ ID NO 42
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 42
gggcggccgc ggttattttt ccaccagaaa gttcaccgca tc                      42

<210> SEQ ID NO 43
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 43
atttattgta caagcctaac ggaagtcgac tagtaaggag aactaaatga acaccctgcc   60
ggata                                                               65

<210> SEQ ID NO 44
<211> LENGTH: 42
<212> TYPE: DNA
<213> ORGANISM: Artificial Sequence
<220> FEATURE:
<223> OTHER INFORMATION: Synthetic Polynucleotide

<400> SEQUENCE: 44
gggcggggat ccttattttt ccaccagaaa gttcaccgca tc                      42

<210> SEQ ID NO 45
<211> LENGTH: 63
<212> TYPE: DNA
<213> ORGANISM: Artificial Sequence
<220> FEATURE:
<223> OTHER INFORMATION: Synthetic Polynucleotide

<400> SEQUENCE: 45
atttatggta cctcacaatc aaatctaagg agttacaaat gaccgcgtat attctgaccg   60
ctg                                                                 63

<210> SEQ ID NO 46
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 46
attgatccgc ggttagcctt tcaggcgatc cgccagg                            37

<210> SEQ ID NO 47
<211> LENGTH: 70
<212> TYPE: DNA
<213> ORGANISM: Artificial Sequence
<220> FEATURE:
<223> OTHER INFORMATION: Synthetic Polynucleotide

<400> SEQUENCE: 47
atttattgta catacactat attaacctaa aaaggagcgt aacgaatgac cgcgtatatt   60
```

-continued ctgaccgctg                                                            70

<210> SEQ ID NO 48
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 48
ggcgcgggat ccttagcctt tcaggcgatc cgccagg                              37

<210> SEQ ID NO 49
<211> LENGTH: 66
<212> TYPE: DNA
<213> ORGANISM: Artificial Sequence
<220> FEATURE:
<223> OTHER INFORMATION: Synthetic Polynucleotide

<400> SEQUENCE: 49
aattatccgc ggtaccaacc ccctattag aataaggagt atcacgcatg cagtttaagg      60
tttaca                                                                66

<210> SEQ ID NO 50
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 50
caggggccgc ggttatattc cccagaacat caggttaatg gcgtttt                   47

<210> SEQ ID NO 51
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 51
ccggggggat ccttatattc cccagaacat caggttaatg gcgtttt                   47

<210> SEQ ID NO 52
<211> LENGTH: 55
<212> TYPE: DNA
<213> ORGANISM: Artificial Sequence
<220> FEATURE:
<223> OTHER INFORMATION: Synthetic Polynucleotide

<400> SEQUENCE: 52
atttatggcg cctccctatc agtgatagag attgacatcc ctatcagtga tagag          55

<210> SEQ ID NO 53
<211> LENGTH: 51
<212> TYPE: DNA
<213> ORGANISM: Artificial Sequence
<220> FEATURE:
<223> OTHER INFORMATION: Synthetic Polynucleotide

<400> SEQUENCE: 53
attcaggata tctgactact gcttggattc tcaccaataa aaaacgcccg g              51

<210> SEQ ID NO 54
<211> LENGTH: 51

```
<212> TYPE: DNA
<213> ORGANISM: Artificial Sequence
<220> FEATURE:
<223> OTHER INFORMATION: Synthetic Polynucleotide

<400> SEQUENCE: 54
attcagccta ggtgactact gcttggattc tcaccaataa aaaacgcccg g          51

<210> SEQ ID NO 55
<211> LENGTH: 2454
<212> TYPE: DNA
<213> ORGANISM: Artificial Sequence
<220> FEATURE:
<223> OTHER INFORMATION: pRJK034 synthetic cloning vector

<400> SEQUENCE: 55
gacgtctgtg caagtactac tgttctgcag tcacttgaat tcgatacccca gctgggtgga    60 gtgcaccaag gagcatgcga aggaaacgtt tcgcagaagc tttccctatc agtgatagag   120
attgacatcc ctatcagtga tagagatact gagcacatca gcaggacgca ctgaccggta   180
ccactttgcc gcggagtatt tgtacatttg aaggatcccg agaattggct tggactcctg   240
ttgatagatc cagtaatgac ctcagaactc catctggatt tgttcagaac gctcggttgc   300
cgccgggcgt tttttattgg tgagaatcca agcagtagtc agagctcgga ctgcttaagt   360
cgctccatat gctcgttccc gggactacac aattgtcccc cggcgccagg ttgatatct   420 atcgccctag gaccgtctc gagagaatca atattaatcc aacgcgtggc atcaaataaa   480
acgaaaggct cagtcgaaag actgggcctt tcgttttatc tgttgtttgt cggtgaacgc   540
tctcctgagt aggacaaatc cgccgcccta gacttaggcg ttcggctgcg gcgagcggta   600
tcagctcact caaaggcggt aatacggtta tccacagaat caggggataa cgcaggaaag   660
aacatgtgag caaaaggcca gcaaaaggcc aggaaccgta aaaaggccgc gttgctggcg   720
ttttcccata ggctccgccc ccctgacgag catcacaaaa atcgacgctc aagtcagagg   780
tggcgaaacc cgacaggact ataaagatac caggcgtttc cccctggaag ctccctcgtg   840
cgctctcctg ttccgaccct gccgcttacc ggatacctgt ccgcctttct cccttcggga   900
agcgtggcgc tttctcatag ctcacgctgt aggtatctca gttcggtgta ggtcgttcgc   960
tccaagctgg gctgtctgca cgaaccccc gttcagcccg accgctgcgc cttatccggt    1020
aactatcgtc ttgagtccaa cccggtaaga cgacttat cgccactggc agcagccact     1080
ggtaacagga ttagcagagc gaggtatgta ggcggtgcta cagagttctt gaagtggtgg   1140
cctaactacg gctacactag aaggacagta tttggtatct gcgctctgct gaagccagtt   1200
accttcggaa aaagagttgg tagctcttga tccggcaaac aaaccaccgc tggtagcggt   1260
ggtttttttg tttgcaagca gcagattacg cgcagaaaaa aaggatctca agaagatcct   1320
ttgatctttt ctacggggtc tgacgctcag tggaacgaaa actcacgtta agggattttg   1380
gtcatggcta gtgcttggat tctcaccaat aaaaaacgcc cggcggcaac cgagcgttct   1440
gaacaaatcc agatggagtt ctgaggtcat tactggatct atcaacagga gtccaagcca   1500
attctcgaac cccagagtcc cgctcagaag aactcgtcaa gaaggcgata gaaggcgatg   1560
cgctgcgaat cgggagcggc gataccgtaa agcacgagga gcggtcagc ccattcgccg    1620 ccaagctctt cagcaatatc acgggtagcc aacgctatgt cctgatagcg gtccgccaca   1680
cccagccggc cacagtcgat gaatccagaa aagcggccat tttccaccat gatattcggc   1740
aagcaggcat cgccgtgggt cacgacgaga tcctcgccgt cgggcatacg cgccttgagc   1800
```

```
ctggcgaaca gttcggctgg cgcgagcccc tgatgctctt cgtccagatc atcctgatcg   1860
acaagaccgg cttccatccg agtacgtgct cgctcgatgc gatgtttcgc ttggtggtcg   1920
aatgggcagg tagccggatc aagcgtatgc agccgccgca ttgcatcagc catgatggat   1980
actttctcgg caggagcaag gtgagatgac aggagatcct gccccggcac ttcgcccaat   2040
agcagccagt cccttcccgc ttcagtgaca acgtcgagca cagccgcgca aggaacgccc   2100
gtcgtggcca gccacgatag ccgcgctgcc tcgtcttgca gttcattcag ggcaccggac   2160
aggtcggtct tgacaaaaag aaccgggcga ccctgcgctg acagccggaa cacggcggca   2220
tcagagcagc cgattgtctg ttgtgcccag tcatagccga atagcctctc acccaagcc    2280 gccggagaac ctgcgtgcaa tccatcttgt tcaatcatgc gaaacgatcc tcatcctgtc   2340
tcttgatcag atcttgatcc cctgcgccat cagatccttg gcggcaagaa agccatccag   2400
tttactttgc agggcttccc aaccttacca gagggcggcc caactggcaa ttcc         2454
```

<210> SEQ ID NO 56
<211> LENGTH: 3172
<212> TYPE: DNA
<213> ORGANISM: Artificial Sequence
<220> FEATURE:
<223> OTHER INFORMATION: pRJK037 synthetic cloning vector

<400> SEQUENCE: 56

```
gacgtctgtg caagtactac tgttctgcag tcacttgaat tcgatacccg gctgggtgga     60
gtgcaccaag gagcatgcga aggaaacgtt tcgcagaagc tttccctatc agtgatagag    120
attgacatcc ctatcagtga tagagatact gagcacatca gcaggacgca ctgaccggta    180
ccctataagt tacacaacat aaggaggaat ataatgcgtc gtcgtccgcg tccgccgtac    240
ctgccgcgtc cgcgtccgcc gccgttcttc ccgccgcgtc tgccgccgcg tatcccgccg    300
ggtttcccgc cgcgtttccc gccgcgtttc ccgtaaccgc ggagtatttg tacattctat    360
caaagtatca taaggaggag aataatgcgt cgtcgtccgc gtccgccgta cctgccgcgt    420
ccgcgtccgc cgccgttctt cccgccgcgt ctgccgccgc gtatcccgcc gggtttcccg    480
ccgcgtttcc cgccgcgttt cccgtaagga tcccgagaat tggcttggac tcctgttgat    540
agatccagta atgacctcag aactccatct ggatttgttc agaacgctcg gttgccgccg    600 ggcgttttt attggtgaga tccaagcag tagtcagagc tcggactgct taagtcgctc    660
catatgctcg ttcccgggac tacacaattg tccccggcg ccagggttga tatctatcgc    720
cctagggacc gtctcgagag cgccctgtag cggcgcatta gcgcggcgg gtgtggtggt    780 tacgcgcagc gtgaccgcta cacttgccag cgccctagcg cccgctcctt tcgctttctt    840
cccttccttt ctcgccacgt tcgccggctt tccccgtcaa gctctaaatc ggggctccc    900 tttagggttc cgatttagtg ctttacggca cctcgacccc aaaaaacttg attagggtga    960
tggttcacgt agtgggccat cgccctgata cggttttt cgccctttga cgttggagtc    1020
cacgttcttt aatagtggac tcttgttcca actggaaca acactcaacc ctatctcggt   1080
ctattctttt gatttataag ggattttgcc gatttcggcc tattggttaa aaaatgagct   1140
gatttaacaa aaatttaacg cgaattaaat attaatccaa cgcgtggcat caaataaaac   1200
gaaaggctca gtcgaaagac tgggcctttc gttttatctg ttgtttgtcg gtgaacgctc   1260
tcctgagtag acaaatccg ccgcctaga cttaggcgtt cggctgcggc gagcggtatc    1320
agctcactca aaggcggtaa tacggttatc cacagaatca ggggataacg caggaaagaa   1380
catgtgagca aaaggccagc aaaaggccag gaaccgtaaa aaggccgcgt tgctggcgtt   1440
```

```
tttccatagg ctccgcccc ctgacgagca tcacaaaaat cgacgctcaa gtcagaggtg    1500
gcgaaacccg acaggactat aaagatacca ggcgtttccc cctggaagct ccctcgtgcg    1560
ctctcctgtt ccgaccctgc cgcttaccgg atacctgtcc gcctttctcc cttcgggaag    1620
cgtggcgctt tctcatagct cacgctgtag gtatctcagt tcggtgtagg tcgttcgctc    1680
caagctgggc tgtctgcacg aaccccccgt tcagcccgac cgctgcgcct tatccggtaa    1740
ctatcgtctt gagtccaacc cggtaagaca cgacttatcg ccactggcag cagccactgg    1800
taacaggatt agcagagcga ggtatgtagg cggtgctaca gagttcttga agtggtggcc    1860
taactacggc tacactagaa ggacagtatt tggtatctgc gctctgctga agccagttac    1920
cttcggaaaa agagttggta gctcttgatc cggcaaacaa accaccgctg gtagcggtgg    1980
tttttttgtt tgcaagcagc agattacgcg cagaaaaaaa ggatctcaag aagatccttt    2040
gatcttttct acggggtctg acgctcagtg gaacgaaaac tcacgttaag ggattttggt    2100 catgagctagt gcttggattc tcaccaataa aaaacgcccg gcggcaaccg agcgttctga    2160
acaaatccag atggagttct gaggtcatta ctggatctat caacaggagt ccaagccaat    2220
tctcgaaccc cagagtcccg ctcagaagaa ctcgtcaaga aggcgataga aggcgatgcg    2280
ctgcgaatcg ggagcggcga taccgtaaag cacgaggaag cggtcagccc attcgccgcc    2340
aagctcttca gcaatatcac gggtagccaa cgctatgtcc tgatagcggt ccgccacacc    2400
cagccggcca cagtcgatga atccagaaaa gcggccattt tccaccatga tattcggcaa    2460
gcaggcatcg ccgtgggtca cgacgagatc ctcgccgtcg gcatacgcg ccttgagcct    2520 ggcgaacagt tcggctggcg cgagcccctg atgctcttcg tccagatcat cctgatcgac    2580
aagaccggct tccatccgag tacgtgctcg ctcgatgcga tgtttcgctt ggtggtcgaa    2640
tgggcaggta gccggatcaa gcgtatgcag ccgccgcatt gcatcagcca tgatggatac    2700
tttctcggca ggagcaaggt gagatgacag gagatcctgc cccggcactt cgcccaatag    2760
cagccagtcc cttcccgctt cagtgacaac gtcgagcaca gccgcgcaag gaacgcccgt    2820
cgtggccagc cacgatagcc gcgctgcctc gtcttgcagt tcattcaggg caccggacag    2880
gtcggtcttg acaaaaagaa ccgggcgacc ctgcgctgac agccggaaca cggcggcatc    2940
agagcagccg attgtctgtt gtgcccagtc atagccgaat agcctctcca cccaagccgc    3000
cggagaacct gcgtgcaatc catcttgttc aatcatgcga acgatcctc atcctgtctc    3060 ttgatcagat cttgatcccc tgcgccatca gatccttggc ggcaagaaag ccatccagtt    3120
tactttgcag ggcttcccaa ccttaccaga gggcggccca actggcaatt cc            3172
```

<210> SEQ ID NO 57
<211> LENGTH: 3053
<212> TYPE: DNA
<213> ORGANISM: Artificial Sequence
<220> FEATURE:
<223> OTHER INFORMATION: pRJK046 synthetic cloning vector

<400> SEQUENCE: 57

```
gacgtctgtg caagtactac tgttctgcag tcacttgaat tcgatacccca gctgggtgga     60 gtgcaccaag gagcatgcga aggaaacgtt tcgcagaagc tttccctatc agtgatagag    120
attgacatcc ctatcagtga tagagatact gagcacatca gcaggacgca ctgaccggta    180
cccaacaggg attcgttaat ttaaggaggt ctccaaatgg gcaacaaccg cccggtgtat    240
attccgcagc gcgcccgcc gcatccgcgc atttaaccgc ggagtatttg tacagaggta    300
```

```
caactcaact aatataagga ggttcaaaat gggcaacaac cgcccggtgt atattccgca    360
gccgcgcccg ccgcatccgc gcatttaagg atcccgagaa ttggcttgga ctcctgttga    420
tagatccagt aatgacctca gaactccatc tggatttgtt cagaacgctc ggttgccgcc    480
gggcgttttt tattggtgag aatccaagca gtagtcagag ctcggactgc ttaagtcgct    540
ccatatgctc gttcccggga ctacacaatt gtccccggc gccagggttg atatctatcg     600
ccctagggac cgtctcgaga gcgccctgta gcggcgcatt aagcgcggcg ggtgtggtgg    660
ttacgcgcag cgtgaccgct acacttgcca gcgccctagc gcccgctcct ttcgctttct    720
tcccttcctt tctcgccacg ttcgccggct ttccccgtca agctctaaat cgggggctcc    780
ctttagggtt ccgatttagt gctttacggc acctcgaccc caaaaaactt gattagggtg    840
atggttcacg tagtgggcca tcgccctgat agacggtttt cgcccctttg acgttggagt    900
ccacgttctt aatagtgga ctcttgttcc aaactggaac aacactcaac cctatctcgg      960
tctattcttt tgatttataa gggattttgc cgatttcggc ctattggtta aaaaatgagc   1020
tgatttaaca aaaatttaac gcgaattaaa tattaatcca acgcgtggca tcaaataaaa   1080
cgaaaggctc agtcgaaaga ctgggccttt cgttttatct gttgtttgtc ggtgaacgct   1140
ctcctgagta ggacaaatcc gccgcccag acttaggcgt tcggctgcgg cgagcggtat     1200
cagctcactc aaaggcggta atacggttat ccacagaatc aggggataac gcaggaaaga   1260
acatgtgagc aaaaggccag caaaaggcca ggaaccgtaa aaaggccgcg ttgctggcgt   1320
ttttccatag gctccgcccc cctgacgagc atcacaaaaa tcgacgctca agtcagaggt   1380
ggcgaaaccc gacaggacta taaagatacc aggcgtttcc ccctggaagc tccctcgtgc   1440
gctctcctgt tccgaccctg ccgcttaccg gatacctgtc cgcctttctc ccttcgggaa   1500
gcgtggcgct ttctcatagc tcacgctgta ggtatctcag ttcggtgtag gtcgttcgct   1560
ccaagctggg ctgtctgcac gaaccccccg ttcagcccga ccgctgcgcc ttatccggta   1620
actatcgtct tgagtccaac ccggtaagac acgacttatc gccactggca gcagccactg   1680
gtaacaggat tagcagagcg aggtatgtag gcggtgctac agagttcttg aagtggtggc   1740
ctaactacgg ctacactaga aggacagtat ttggtatctg cgctctgctg aagccagtta   1800
ccttcggaaa aagagttggt agctcttgat ccggcaaaca accaccgct ggtagcggtg     1860 gtttttttgt ttgcaagcag cagattacgc gcagaaaaaa aggatctcaa gaagatcctt   1920
tgatcttttc tacggggtct gacgctcagt ggaacgaaaa ctcacgttaa gggattttgg   1980
tcatggctag tgcttggatt ctcaccaata aaaaacgccc ggcggcaacc gagcgttctg   2040
aacaaatcca gatggagttc tgaggtcatt actggatcta tcaacaggag tccaagccaa   2100
ttctcgaacc ccagagtccc gctcagaaga actcgtcaag aaggcgatag aaggcgatgc   2160
gctgcgaatc gggagcggcg ataccgtaaa gcacgaggaa gcggtcagcc cattcgccgc   2220
caagctcttc agcaatatca cgggtagcca acgctatgtc ctgatagcgg tccgccacac   2280
ccagccggcc acagtcgatg aatccagaaa agcggccatt ttccaccatg atattcggca   2340
agcaggcatc gccgtgggtc acgacgagat cctcgccgtc gggcatacgc gccttgagcc   2400
tggcgaacag ttcggctggc gcgagcccct gatgctcttc gtccagatca tcctgatcga   2460
caagaccggc ttccatccga gtacgtgctc gctcgatgcg atgtttcgct tggtggtcga   2520
atgggcaggt agccggatca agcgtatgca gccgccgcat tgcatcagcc atgatggata   2580
ctttctcggc aggagcaagg tgagatgaca ggagatcctg ccccggcact cgcccaata    2640 gcagccagtc ccttcccgct tcagtgacaa cgtcgagcac agccgcgcaa ggaacgcccg   2700
```

```
tcgtggccag ccacgatagc cgcgctgcct cgtcttgcag ttcattcagg gcaccggaca    2760
ggtcggtctt gacaaaaaga accgggcgac cctgcgctga cagccggaac acggcggcat    2820
cagagcagcc gattgtctgt tgtgcccagt catagccgaa tagcctctcc acccaagccg    2880
ccggagaacc tgcgtgcaat ccatcttgtt caatcatgcg aaacgatcct catcctgtct    2940
cttgatcaga tcttgatccc ctgcgccatc agatccttgg cggcaagaaa gccatccagt    3000
ttactttgca gggcttccca accttaccag agggcggccc aactggcaat tcc            3053

<210> SEQ ID NO 58
<211> LENGTH: 2692
<212> TYPE: DNA
<213> ORGANISM: Artificial Sequence
<220> FEATURE:
<223> OTHER INFORMATION: pRJK055 synthetic cloning vector

<400> SEQUENCE: 58
gacgtctgtg caagtactac tgttctgcag tcacttgaat tcgatacccca gctgggtgga     60 gtgcaccaag gagcatgcga aggaaacgtt tcgcagaagc tttccctatc agtgatagag    120
attgacatcc ctatcagtga tagagatact gagcacatca gcaggacgca ctgaccggta    180
cccgactaac aactctataa ggaggtccat aaatgacccg cagcagccgc gcgggcctgc    240
agtttccggt gggccgcgtg catcgcctgc tgcgcaaaga ctacaaagac gacgacgaca    300
aataaccgcg gagtatttgt acagaggtac aactcaacta atataaggag gttcaaaatg    360
acccgcagca gccgcgcggg cctgcagttt ccggtgggcc gcgtgcatcg cctgctgcgc    420
aaagactaca agacgacga cgacaaataa ggatcccgag aattggcttg gactcctgtt    480
gatagatcca gtaatgacct cagaactcca tctggatttg ttcagaacgc tcggttgccg    540
ccgggcgttt tttattggtg agaatccaag cagtagtcag agctcggact gcttaagtcg    600
ctccatatgc tcgttcccgg gactacacaa ttgtccccca gcgccagggt tgatatctat    660
cgccctaggg accgtctcga gagaatcaat attaatccaa cgcgtggcat caaataaaac    720
gaaaggctca gtcgaaagac tgggcctttc gttttatctg ttgtttgtcg gtgaacgctc    780
tcctgagtag gacaaatccg ccgccctaga cttaggcgtt cggctgcggc gagcggtatc    840
agctcactca aaggcggtaa tacggttatc cacagaatca ggggataacg caggaaagaa    900
catgtgagca aaaggccagc aaaaggccag gaaccgtaaa aaggccgcgt tgctggcgtt    960
tttccatagg ctccgccccc ctgacgagca tcacaaaaat cgacgctcaa gtcagaggtg   1020
gcgaaacccg acaggactat aaagatacca ggcgtttccc cctggaagct ccctcgtgcg   1080
ctctcctgtt ccgaccctgc cgcttaccgg atacctgtcc gcctttctcc cttcgggaag   1140
cgtggcgctt tctcatagct cacgctgtag gtatctcagt tcggtgtagg tcgttcgctc   1200
caagctgggc tgtctgcacg aaccccccgt tcagcccgac cgctgcgcct tatccggtaa   1260
ctatcgtctt gagtccaacc cggtaagaca cgacttatcg ccactggcag cagccactgg   1320
taacaggatt agcagagcga ggtatgtagg cggtgctaca gagttcttga agtggtggcc   1380
taactacggc tacactagaa ggacagtatt tggtatctgc gctctgctga agccagttac   1440
cttcggaaaa agagttggta gctcttgatc cggcaaacaa accaccgctg gtagcggtgg   1500
tttttttgtt tgcaagcagc agattacgcg cagaaaaaaa ggatctcaag aagatccttt   1560
gatcttttct acggggtctg acgctcagtg gaacgaaaac tcacgttaag ggattttggt   1620
catggctagt gcttggattc tcaccaataa aaaacgcccg gcggcaaccg agcgttctga   1680
```

| | |
|---|---|
| acaaatccag atggagttct gaggtcatta ctggatctat aacaggagt ccaagccaat | 1740 |
| tctcgaaccc cagagtcccg ctcagaagaa ctcgtcaaga aggcgataga aggcgatgcg | 1800 |
| ctgcgaatcg ggagcggcga taccgtaaag cacgaggaag cggtcagccc attcgccgcc | 1860 |
| aagctcttca gcaatatcac gggtagccaa cgctatgtcc tgatagcggt ccgccacacc | 1920 |
| cagccggcca cagtcgatga atccagaaaa gcggccattt tccaccatga tattcggcaa | 1980 |
| gcaggcatcg ccgtgggtca cgacgagatc ctcgccgtcg gcatacgcg ccttgagcct | 2040 |
| ggcgaacagt tcggctggcg cgagccctg atgctcttcg tccagatcat cctgatcgac | 2100 |
| aagaccggct tccatccgag tacgtgctcg ctcgatgcga tgtttcgctt ggtggtcgaa | 2160 |
| tgggcaggta gccggatcaa gcgtatgcag ccgccgcatt gcatcagcca tgatggatac | 2220 |
| tttctcggca ggagcaaggt gagatgacag agatcctgc cccggcactt cgcccaatag | 2280 |
| cagccagtcc cttcccgctt cagtgacaac gtcgagcaca ccgcgcaag gaacgcccgt | 2340 |
| cgtggccagc cacgatagcc gcgctgcctc gtcttgcagt tcattcaggg caccggacag | 2400 |
| gtcggtcttg acaaaaagaa ccgggcgacc ctgcgctgac agccggaaca cggcggcatc | 2460 |
| agagcagccg attgtctgtt gtgcccagtc atagccgaat agcctctcca cccaagccgc | 2520 |
| cggagaacct gcgtgcaatc catccttgttc aatcatgcga acgatcctc atcctgtctc | 2580 |
| ttgatcagat cttgatcccc tgcgccatca gatccttggc ggcaagaaag ccatccagtt | 2640 |
| tactttgcag ggcttcccaa ccttaccaga gggcggccca actggcaatt cc | 2692 |

<210> SEQ ID NO 59
<211> LENGTH: 2696
<212> TYPE: DNA
<213> ORGANISM: Artificial Sequence
<220> FEATURE:
<223> OTHER INFORMATION: pRJK062 synthetic cloning vector

<400> SEQUENCE: 59

| | |
|---|---|
| gacgtctgtg caagtactac tgttctgcag tcacttgaat tcgatacca gctgggtgga | 60 |
| gtgcaccaag gagcatgcga aggaaacgtt tcgcagaagc tttccctatc agtgatagag | 120 |
| attgacatcc ctatcagtga tagagatact gagcacatca gcaggacgca ctgaccggta | 180 |
| cctaaaagag gagactcacc cttaaggagg tataagatgg cgctgtggaa aaacatgctg | 240 |
| aaaggcattg gcaaactggc gggcaaagcg cgctgggcg cggtgaaaaa actggtgggc | 300 |
| gcggaaagct aaccgcggag tatttgtaca caagtacaga ggagtaagga ggtaaagtat | 360 |
| ggcgctgtgg aaaaacatgc tgaaaggcat tggcaaactg gcgggcaaag cggcgctggg | 420 |
| cgcggtgaaa aaactggtgg gcgcggaaag ctaaggatcc cgagaattgg cttggactcc | 480 |
| tgttgataga tccagtaatg acctcagaac tccatctgga tttgttcaga acgctcggtt | 540 |
| gccgccgggc gttttttatt ggtgagaatc caagcagtag tcagagctcg gactgcttaa | 600 |
| gtcgctccat atgctcgttc ccgggactac acaattgtcc ccggcgcca gggttgatat | 660 |
| ctatcgccct agggaccgtc tcgagagaat caatattaat ccaacgcgtg gcatcaaata | 720 |
| aaacgaaagg ctcagtcgaa agactgggcc tttcgtttta tctgttgttt gtcggtgaac | 780 |
| gctctcctga gtaggacaaa tccgccgccc tagacttagg cgttcggctg cggcgagcgg | 840 |
| tatcagctca ctcaaaggcg gtaatacggt tatccacaga atcagggat aacgcaggaa | 900 |
| agaacatgtg agcaaaaggc cagcaaaagg ccaggaaccg taaaaaggcc gcgttgctgg | 960 |
| cgttttttcca taggctccgc cccctgacg agcatcacaa aaatcgacgc tcaagtcaga | 1020 |
| ggtggcgaaa cccgacagga ctataaagat accaggcgtt tcccctggaa gctccctcg | 1080 |

```
tgcgctctcc tgttccgacc ctgccgctta ccggatacct gtccgccttt ctcccttcgg   1140
gaagcgtggc gctttctcat agctcacgct gtaggtatct cagttcggtg taggtcgttc   1200
gctccaagct gggctgtctg cacgaacccc ccgttcagcc cgaccgctgc gccttatccg   1260
gtaactatcg tcttgagtcc aacccggtaa gacacgactt atcgccactg gcagcagcca   1320
ctggtaacag gattagcaga gcgaggtatg taggcggtgc tacagagttc ttgaagtggt   1380
ggcctaacta cggctacact agaaggacag tatttggtat ctgcgctctg ctgaagccag   1440
ttaccttcgg aaaaagagtt ggtagctctt gatccggcaa acaaaccacc gctggtagcg   1500 gtggttttt tgtttgcaag cagcagatta cgcgcagaaa aaaggatct caagaagatc    1560 ctttgatctt ttctacgggg tctgacgctc agtggaacga aaactcacgt taagggattt   1620
tggtcatggc tagtgcttgg attctcacca ataaaaaacg cccggcggca accgagcgtt   1680
ctgaacaaat ccagatggag ttctgaggtc attactggat ctatcaacag gagtccaagc   1740
caattctcga accccagagt cccgctcaga gaactcgtc aagaaggcga tagaaggcga    1800
tgcgctgcga atcgggagcg gcgataccgt aaagcacgag gaagcggtca gcccattcgc   1860
cgccaagctc ttcagcaata tcacgggtag ccaacgctat gtcctgatag cggtccgcca   1920
cacccagccg gccacagtcg atgaatccag aaaagcggcc attttccacc atgatattcg   1980
gcaagcaggc atcgccgtgg gtcacgacga gatcctcgcc gtcgggcata cgcgccttga   2040
gcctggcgaa cagttcggct ggcgcgagcc cctgatgctc ttcgtccaga tcatcctgat   2100
cgacaagacc ggcttccatc cgagtacgtg ctcgctcgat gcgatgtttc gcttggtggt   2160
cgaatgggca ggtagccgga tcaagcgtat gcagccgccg cattgcatca gccatgatgg   2220
atactttctc ggcaggagca aggtgagatg acaggagatc ctgccccggc acttcgccca   2280
atagcagcca gtcccttccc gcttcagtga caacgtcgag cacagccgcg caaggaacgc   2340
ccgtcgtggc cagccacgat agccgcgctg cctcgtcttg cagttcattc agggcaccgg   2400
acaggtcggt cttgacaaaa agaaccgggc gaccctgcgc tgacagccgg aacacggcgg   2460
catcagagca gccgattgtc tgttgtgccc agtcatagcc gaatagcctc tccacccaag   2520
ccgccggaga acctgcgtgc aatccatctt gttcaatcat gcgaaacgat cctcatcctg   2580
tctcttgatc agatcttgat cccctgcgcc atcagatcct ggcggcaag aaagccatcc    2640 agtttacttt gcagggcttc ccaaccttac cagagggcgg cccaactggc aattcc       2696
```

<210> SEQ ID NO 60
<211> LENGTH: 2671
<212> TYPE: DNA
<213> ORGANISM: Artificial Sequence
<220> FEATURE:
<223> OTHER INFORMATION: pRJK070 synthetic cloning vector

<400> SEQUENCE: 60

```
gacgtctgtg caagtactac tgttctgcag tcacttgaat tcgatacccca gctgggtgga   60 gtgcaccaag gagcatgcga aggaaacgtt tcgcagaagc tttccctatc agtgatagag   120
attgacatcc ctatcagtga tagagatact gagcacatca gcaggacgca ctgaccggta   180
ccaacggtaa gaggcataat ttaaggaggt aacacatggg ctggggcagc ttttttaaaa   240
aagcggcgca tgtgggcaaa catgtgggca aagcggcgct gacccattat ctgtaaccgc   300
ggagtatttg tacagattta taaatcgga atagataagg aggtacacat gggctggggc    360
agctttttta aaaagcggc gcatgtgggc aaacatgtgg gcaaagcggc gctgacccat    420
```

```
tatctgtaag gatcccgaga attggcttgg actcctgttg atagatccag taatgacctc    480
agaactccat ctggatttgt tcagaacgct cggttgccgc cgggcgtttt ttattggtga    540
gaatccaagc agtagtcaga gctcggactg cttaagtcgc tccatatgct cgttcccggg    600
actacacaat tgtcccccgg cgccagggtt gatatctatc gccctaggga ccgtctcgag    660
agaatcaata ttaatccaac gcgtggcatc aaataaaacg aaaggctcag tcgaaagact    720
gggcctttcg ttttatctgt tgtttgtcgg tgaacgctct cctgagtagg acaaatccgc    780
cgccctagac ttaggcgttc ggctgcggcg agcggtatca gctcactcaa aggcggtaat    840
acggttatcc acagaatcag gggataacgc aggaaagaac atgtgagcaa aaggccagca    900
aaaggccagg aaccgtaaaa aggccgcgtt gctggcgttt ttccataggc tccgcccccc    960
tgacgagcat cacaaaaatc gacgctcaag tcagaggtgg cgaaacccga caggactata   1020
aagataccag gcgtttcccc ctggaagctc cctcgtgcgc tctcctgttc cgaccctgcc   1080
gcttaccgga tacctgtccg cctttctccc ttcgggaagc gtggcgcttt ctcatagctc   1140
acgctgtagg tatctcagtt cggtgtaggt cgttcgctcc aagctgggct gtctgcacga   1200
accccccgtt cagcccgacc gctgcgcctt atccggtaac tatcgtcttg agtccaaccc   1260
ggtaagacac gacttatcgc cactggcagc agccactggt aacaggatta gcagagcgag   1320
gtatgtaggc ggtgctacag agttcttgaa gtggtggcct aactacggct acactagaag   1380
gacagtattt ggtatctgcg ctctgctgaa gccagttacc ttcggaaaaa gagttggtag   1440
ctcttgatcc ggcaaacaaa ccaccgctgg tagcggtggt ttttttgttt gcaagcagca   1500
gattacgcgc agaaaaaaag gatctcaaga agatcctttg atcttttcta cggggtctga   1560
cgctcagtgg aacgaaaact cacgttaagg gattttggtc atgctagtg cttggattct   1620
caccaataaa aaacgcccgg cggcaaccga gcgttctgaa caaatccaga tggagttctg   1680
aggtcattac tggatctatc aacaggagtc caagccaatt ctcgaacccc agagtcccgc   1740
tcagaagaac tcgtcaagaa ggcgatagaa ggcgatgcgc tgcgaatcgg gagcggcgat   1800
accgtaaagc acgaggaagc ggtcagccca ttcgccgcca agctcttcag caatatcacg   1860
ggtagccaac gctatgtcct gatagcggtc cgccacaccc agccggccac agtcgatgaa   1920
tccagaaaag cggccatttt ccaccatgat attcggcaag caggcatcgc cgtgggtcac   1980
gacgagatcc tcgccgtcgg catacgcgc ttgagcctg cgaacagtt cggctggcgc   2040
gagcccctga tgctcttcgt ccagatcatc ctgatcgaca agaccggctt ccatccgagt   2100
acgtgctcgc tcgatgcgat gtttcgcttg gtggtcgaat gggcaggtag ccggatcaag   2160
cgtatgcagc cgccgcattg catcagccat gatggatact ttctcggcag gagcaaggtg   2220
agatgacagg agatcctgcc ccggcacttc gcccaatagc agccagtccc ttcccgcttc   2280
agtgacaacg tcgagcacag ccgcgcaagg aacgcccgtc gtggccagcc acgatagccg   2340
cgctgcctcg tcttgcagtt cattcagggc accggacagg tcggtcttga caaaaagaac   2400
cgggcgaccc tgcgctgaca gccggaacac ggcggcatca gagcagccga ttgtctgttg   2460
tgcccagtca tagccgaata gcctctccac ccaagccgcc ggagaacctg cgtgcaatcc   2520
atcttgttca atcatgcgaa acgatcctca tcctgtctct tgatcagatc ttgatccct   2580
gcgccatcag atccttggcg gcaagaaagc catccagttt actttgcagg gcttcccaac   2640
cttaccagag ggcggcccaa ctggcaattc c                                  2671

<210> SEQ ID NO 61
<211> LENGTH: 3172
```

<212> TYPE: DNA
<213> ORGANISM: Artificial Sequence
<220> FEATURE:
<223> OTHER INFORMATION: pPh037 synthetic cloning vector

<400> SEQUENCE: 61

| | | | | | |
|---|---|---|---|---|---|
| gacgtctgtg | caagtactac | tgttctgcag | tcacttgaat | tcgatacccca | gctgggtgga | 60 |
| gtgcaccaag | gagcatgcga | aggaaacgtt | tcgcagaagc | tttccctatc | agtgatagag | 120 |
| attgacatcc | ctatcagtga | tagagatact | gagcacatca | gcaggacgca | ctgaccggta | 180 |
| ccctataagt | tacacaacat | aaggaggaat | ataatgcgtc | gtcgtccgcg | tccgccgtac | 240 |
| ctgccgcgtc | cgcgtccgcc | gccgttcttc | ccgccgcgtc | tgccgccgcg | tatcccgccg | 300 |
| ggtttcccgc | cgcgtttccc | gccgcgtttc | ccgtaaccgc | ggagtatttg | tacattctat | 360 |
| caaagtatca | taaggaggag | aataatgcgt | cgtcgtccgc | gtccgccgta | cctgccgcgt | 420 |
| ccgcgtccgc | cgccgttctt | cccgccgcgt | ctgccgccgc | gtatcccgcc | gggtttcccg | 480 |
| ccgcgtttcc | cgccgcgttt | cccgtaagga | tcccgagaat | tggcttggac | tcctgttgat | 540 |
| agatccagta | atgacctcag | aactccatct | ggatttgttc | agaacgctcg | gttgccgccg | 600 |
| ggcgtttttt | attggtgaga | atccaagcag | tagtcagagc | tcggactgct | taagtcgctc | 660 |
| catatgctcg | ttcccgggac | tacacaattg | tcccccggcg | ccagggttga | tatctatcgc | 720 |
| cctagggacc | gtctcgagag | cgccctgtag | cggcgcatta | agcgcggcgg | gtgtggtggt | 780 |
| tacgcgcagc | gtgaccgcta | cacttgccag | cgccctagcg | cccgctcctt | tcgctttctt | 840 |
| cccttccttt | ctcgccacgt | tcgccggctt | tccccgtcaa | gctctaaatc | ggggggctccc | 900 |
| tttagggttc | cgatttagtg | ctttacggca | cctcgacccc | aaaaaacttg | attagggtga | 960 |
| tggttcacgt | agtgggccat | cgccctgata | gacggttttt | cgccctttga | cgttggagtc | 1020 |
| cacgttcttt | aatagtggac | tcttgttcca | aactggaaca | acactcaacc | ctatctcggt | 1080 |
| ctattctttt | gatttataag | ggattttgcc | gatttcggcc | tattggttaa | aaaatgagct | 1140 |
| gatttaacaa | aaatttaacg | cgaattaaat | attaatccaa | cgcgtggcat | caaataaaac | 1200 |
| gaaaggctca | gtcgaaagac | tgggcctttc | gtttttatctg | ttgtttgtcg | gtgaacgctc | 1260 |
| tcctgagtag | gacaaatccg | ccgccctaga | cttaggcgtt | cggctgcggc | gagcggtatc | 1320 |
| agctcactca | aaggcggtaa | tacggttatc | cacagaatca | ggggataacg | caggaaagaa | 1380 |
| catgtgagca | aaaggccagc | aaaaggccag | gaaccgtaaa | aaggccgcgt | tgctggcgtt | 1440 |
| tttccatagg | ctccgccccc | ctgacgagca | tcacaaaaat | cgacgctcaa | gtcagaggtg | 1500 |
| gcgaaacccg | acaggactat | aaagatacca | ggcgtttccc | cctggaagct | ccctcgtgcg | 1560 |
| ctctcctgtt | ccgaccctgc | cgcttaccgg | atacctgtcc | gcctttctcc | cttcgggaag | 1620 |
| cgtggcgctt | tctcatagct | cacgctgtag | gtatctcagt | tcggtgtagg | tcgttcgctc | 1680 |
| caagctgggc | tgtctgcacg | aaccccccgt | tcagcccgac | cgctgcgcct | tatccggtaa | 1740 |
| ctatcgtctt | gagtccaacc | cggtaagaca | cgacttatcg | ccactggcag | cagccactgg | 1800 |
| taacaggatt | agcagagcga | ggtatgtagg | cggtgctaca | gagttcttga | agtggtggcc | 1860 |
| taactacggc | tacactagaa | ggacagtatt | tggtatctgc | gctctgctga | agccagttac | 1920 |
| cttcggaaaa | agagttggta | gctcttgatc | cggcaaacaa | accaccgctg | gtagcggtgg | 1980 |
| tttttttgtt | tgcaagcagc | agattacgcg | cagaaaaaaa | ggatctcaag | aagatccttt | 2040 |
| gatcttttct | acggggtctg | acgctcagtg | gaacgaaaac | tcacgttaag | ggattttggt | 2100 |
| catggctagt | gcttggattc | tcaccaataa | aaaacgcccg | gcggcaaccg | agcgttctga | 2160 |

```
acaaatccag atggagttct gaggtcatta ctggatctat aacaggagt ccaagccaat    2220
tctcgaaccc cagagtcccg ctcagaagaa ctcgtcaaga aggcgataga aggcgatgcg    2280
ctgcgaatcg ggagcggcga taccgtaaag cacgaggaag cggtcagccc attcgccgcc    2340
aagctcttca gcaatatcac gggtagccaa cgctatgtcc tgatagcggt ccgccacacc    2400
cagccggcca cagtcgatga atccagaaaa gcggccattt tccaccatga tattcggcaa    2460
gcaggcatcg ccgtgggtca cgacgagatc ctcgccgtcg gcatacgcg ccttgagcct    2520
ggcgaacagt tcggctggcg cgagcccctg atgctcttcg tccagatcat cctgatcgac    2580
aagaccggct tccatccgag tacgtgctcg ctcgatgcga tgtttcgctt ggtggtcgaa    2640
tgggcaggta gccggatcaa gcgtatgcag ccgccgcatt gcatcagcca tgatggatac    2700
tttctcggca ggagcaaggt gagatgacag agatcctgc cccggcactt cgcccaatag    2760
cagccagtcc cttcccgctt cagtgacaac gtcgagcaca ccgcgcaag gaacgcccgt    2820
cgtggccagc cacgatagcc gcgctgcctc gtcttgcagt tcattcaggg caccggacag    2880
gtcggtcttg acaaaaagaa ccgggcgacc ctgcgctgac agccggaaca cggcggcatc    2940
agagcagccg attgtctgtt gtgcccagtc atagccgaat agcctctcca cccaagccgc    3000
cggagaacct gcgtgcaatc catccttgttc aatcatgcga aacgatcctc atcctgtctc    3060
ttgatcagat cttgatcccc tgcgccatca gatccttggc ggcaagaaag ccatccagtt    3120
tactttgcag ggcttcccaa ccttaccaga gggcggccca actggcaatt cc             3172

<210> SEQ ID NO 62
<211> LENGTH: 3053
<212> TYPE: DNA
<213> ORGANISM: Artificial Sequence
<220> FEATURE:
<223> OTHER INFORMATION: pPh046 synthetic cloning vector

<400> SEQUENCE: 62
gacgtctgtg caagtactac tgttctgcag tcacttgaat tcgataccca gctgggtgga      60
gtgcaccaag gagcatgcga aggaaacgtt tcgcagaagc tttccctatc agtgatagag     120
attgacatcc ctatcagtga tagagatact gagcacatca gcaggacgca ctgaccggta     180
cccaacaggg attcgttaat ttaaggaggt ctccaaatgg caacaaccg cccggtgtat     240
attccgcagc gcgcccgcc gcatccgcgc atttaaccgc ggagtatttg tacagaggta     300
caactcaact aatataagga ggttcaaaat gggcaacaac cgcccggtgt atattccgca     360
gccgcgcccg ccgcatccgc gcatttaagg atcccgagaa ttggcttgga ctcctgttga     420
tagatccagt aatgacctca gaactccatc tggatttgtt cagaacgctc ggttgccgcc     480
gggcgttttt tattggtgag aatccaagca gtagtcagag ctcggactgc ttaagtcgct     540
ccatatgctc gttcccggga ctacacaatt gtccccggc gccaggggttg atatctatcg     600
ccctagggac cgtctcgaga gcgccctgta gcggcgcatt aagcgcggcg ggtgtggtgg     660
ttacgcgcag cgtgaccgct acacttgcca gcgccctagc gcccgctcct ttcgctttct     720
tcccttcctt tctcgccacg ttcgccggct ttccccgtca gctctaaat cggggggctcc     780
ctttagggtt ccgatttagt gctttacggc acctcgaccc caaaaaactt gattagggtg     840
atggttcacg tagtgggcca tcgccctgat agacggtttt tcgccctttg acgttggagt     900
ccacgttctt taatagtgga ctcttgttcc aaactggaac aacactcaac cctatctcgg     960
tctattcttt tgatttataa gggatttttgc cgatttcggc ctattggtta aaaaatgagc    1020
tgatttaaca aaaatttaac gcgaattaaa tattaatcca acgcgtggca tcaaataaaa    1080
```

```
cgaaaggctc agtcgaaaga ctgggccttt cgttttatct gttgtttgtc ggtgaacgct    1140
ctcctgagta ggacaaatcc gccgcccctag acttaggcgt tcggctgcgg cgagcggtat   1200
cagctcactc aaaggcggta atacggttat ccacagaatc aggggataac gcaggaaaga   1260
acatgtgagc aaaaggccag caaaaggcca ggaaccgtaa aaaggccgcg ttgctggcgt   1320
ttttccatag gctccgcccc cctgacgagc atcacaaaaa tcgacgctca agtcagaggt   1380
ggcgaaaccc gacaggacta taaagatacc aggcgtttcc ccctggaagc tccctcgtgc   1440
gctctcctgt tccgaccctg ccgcttaccg gatacctgtc cgcctttctc ccttcgggaa   1500
gcgtggcgct ttctcatagc tcacgctgta ggtatctcag ttcggtgtag gtcgttcgct   1560
ccaagctggg ctgtctgcac gaaccccccg ttcagcccga ccgctgcgcc ttatccggta   1620
actatcgtct tgagtccaac ccggtaagac acgacttatc gccactggca gcagccactg   1680
gtaacaggat tagcagagcg aggtatgtag gcggtgctac agagttcttg aagtggtggc   1740
ctaactacgg ctacactaga aggacagtat ttggtatctg cgctctgctg aagccagtta   1800
ccttcggaaa aagagttggt agctcttgat ccggcaaaca accaccgct ggtagcggtg    1860 gtttttttgt ttgcaagcag cagattacgc gcagaaaaaa aggatctcaa gaagatcctt   1920
tgatcttttc tacggggtct gacgctcagt ggaacgaaaa ctcacgttaa gggattttgg   1980
tcatggctag tgcttggatt ctcaccaata aaaaacgccc ggcggcaacc gagcgttctg   2040
aacaaatcca gatggagttc tgaggtcatt actggatcta tcaacaggag tccaagccaa   2100
ttctcgaacc ccagagtccc gctcagaaga actcgtcaag aaggcgatag aaggcgatgc   2160
gctgcgaatc gggagcggcg ataccgtaaa gcacgaggaa gcggtcagcc cattcgccgc   2220
caagctcttc agcaatatca cgggtagcca acgctatgtc ctgatagcgg tccgccacac   2280
ccagccggcc acagtcgatg aatccagaaa agcggccatt ttccaccatg atattcggca   2340
agcaggcatc gccgtgggtc acgacgagat cctcgccgtc gggcatacgc gccttgagcc   2400
tggcgaacag ttcggctggc gcgagcccct gatgctcttc gtccagatca tcctgatcga   2460
caagaccggc ttccatccga gtacgtgctc gctcgatgcg atgtttcgct tggtggtcga   2520
atgggcaggt agccggatca agcgtatgca gccgccgcat tgcatcagcc atgatggata   2580
ctttctcggc aggagcaagg tgagatgaca ggagatcctg ccccggcact tcgcccaata   2640
gcagccagtc ccttcccgct tcagtgacaa cgtcgagcac agccgcgcaa ggaacgcccg   2700
tcgtggccag ccacgatagc cgcgctgcct cgtcttgcag ttcattcagg gcaccggaca   2760
ggtcggtctt gacaaaaaga accgggcgac cctgcgctga cagccggaac acggcggcat   2820
cagagcagcc gattgtctgt tgtgcccagt catagccgaa tagcctctcc acccaagccg   2880
ccggagaacc tgcgtgcaat ccatcttgtt caatcatgcg aaacgatcct catcctgtct   2940
cttgatcaga tcttgatccc ctgcgccatc agatccttgg cggcaagaaa gccatccagt   3000
ttactttgca gggcttccca accttaccag agggcggccc aactggcaat tcc          3053
```

<210> SEQ ID NO 63  
<211> LENGTH: 3581  
<212> TYPE: DNA  
<213> ORGANISM: Artificial Sequence  
<220> FEATURE:  
<223> OTHER INFORMATION: pPh079 synthetic cloning vector

<400> SEQUENCE: 63

```
gacgtctgtg caagtactac tgttctgcag tccctatcag tgatagagat tgacatccct    60
```

```
atcagtgata gagatactga gcacatcagc aggacgcact gaccggtacc ctataagtta    120
cacaacataa ggaggaatat aatgcgtcgt cgtccgcgtc cgccgtacct gccgcgtccg    180
cgtccgccgc cgttcttccc gccgcgtctg ccgccgcgta tcccgccggg tttcccgccg    240
cgtttcccgc cgcgtttccc gtaaccgcgg agtatttgta cattctatca agtatcata     300 aggaggagaa taatgcgtcg tcgtccgcgt ccgccgtacc tgccgcgtcc gcgtccgccg    360
ccgttcttcc cgccgcgtct gccgccgcgt atcccgccgg gtttcccgcc gcgtttcccg    420
ccgcgtttcc cgtaaggatc ccgagaattg gcttggactc ctgttgatag atccagtaat    480
gacctcagaa ctccatctgg atttgttcag aacgctcggt tgccgccggg cgttttttat    540
tggtgagaat ccaagcagta gtcagaattc gatacccagc tgggtggagt gcaccaagga    600
gcatgcgaag gaaacgtttc gcagaagctt tccctatcag tgatagagat tgacatccct    660
atcagtgata gagatactga gcacatcagc aggacgcact gaccggtacc caacagggat    720
tcgttaattt aaggaggtct ccaaatgggc aacaaccgcc cggtgtatat tccgcagccg    780
cgcccgccgc atccgcgcat ttaaccgcgg agtatttgta cagaggtaca actcaactaa    840
tataaggagg ttcaaaatgg caacaaccg cccggtgtat attccgcagc cgcgcccgcc    900
gcatccgcgc atttaaggat cccgagaatt ggcttggact cctgttgata gatccagtaa    960
tgacctcaga actccatctg gatttgttca gaacgctcgg ttgccgccgg gcgtttttta    1020
ttggtgagaa tccaagcagt agtcagagct cggactgctt aagtcgctcc atatgctcgt    1080
tcccgggact acacaattgt cccccggcgc cagggttgat atctatcgcc ctagggaccg    1140
tctcgagagc gccctgtagc ggcgcattaa gcgcggcggg tgtggtggtt acgcgcagcg    1200
tgaccgctac acttgccagc gccctagcgc ccgctccttt cgctttcttc ccttcctttc    1260
tcgccacgtt cgccggcttt ccccgtcaag ctctaaatcg gggctccct ttagggttcc     1320 gatttagtgc tttacggcac ctcgacccca aaaaacttga ttagggtgat ggttcacgta    1380
gtgggccatc gccctgatag acggttttc gccctttgac gttggagtcc acgttcttta     1440
atagtggact cttgttccaa actggaacaa cactcaaccc tatctcggtc tattctttg      1500 atttataagg gattttgccg atttcggcct attggttaaa aaatgagctg atttaacaaa    1560
aatttaacgc gaattaaata ttaatccaac gcgtggcatc aaataaaacg aaaggctcag    1620
tcgaaagact gggcctttcg ttttatctgt tgtttgtcgg tgaacgctct cctgagtagg    1680
acaaatccgc cgccctagac ttaggcgttc ggctgcggcg agcggtatca gctcactcaa    1740
aggcggtaat acggttatcc acagaatcag gggataacgc aggaaagaac atgtgagcaa    1800
aaggccagca aaaggccagg aaccgtaaaa aggccgcgtt gctggcgttt ttccataggc    1860
tccgcccccc tgacgagcat cacaaaaatc gacgctcaag tcagaggtgg cgaaacccga    1920
caggactata aagataccag gcgtttcccc ctggaagctc cctcgtgcgc tctcctgttc    1980
cgaccctgcc gcttaccgga tacctgtccg cctttctccc ttcgggaagc gtggcgcttt    2040
ctcatagctc acgctgtagg tatctcagtt cggtgtaggt cgttcgctcc aagctgggct    2100
gtctgcacga accccccgtt cagcccgacc gctgcgcctt atccggtaac tatcgtcttg    2160
agtccaaccc ggtaagacac gacttatcgc cactggcagc agccactggt aacaggatta    2220
gcagagcgag gtatgtaggc ggtgctacag agttcttgaa gtggtggcct aactacggct    2280
acactagaag gacagtattt ggtatctgcg ctctgctgaa gccagttacc ttcggaaaaa    2340
gagttggtag ctcttgatcc ggcaaacaaa ccaccgctgg tagcggtggt ttttttgttt    2400
gcaagcagca gattacgcgc agaaaaaaag gatctcaaga agatcctttg atcttttcta    2460
```

-continued

```
cggggtctga cgctcagtgg aacgaaaact cacgttaagg gattttggtc atggctagtg    2520
cttggattct caccaataaa aaacgcccgg cggcaaccga gcgttctgaa caaatccaga    2580
tggagttctg aggtcattac tggatctatc aacaggagtc caagccaatt ctcgaacccc    2640
agagtcccgc tcagaagaac tcgtcaagaa ggcgatagaa ggcgatgcgc tgcgaatcgg    2700
gagcggcgat accgtaaagc acgaggaagc ggtcagccca ttcgccgcca agctcttcag    2760
caatatcacg ggtagccaac gctatgtcct gatagcggtc cgccacaccc agccggccac    2820
agtcgatgaa tccagaaaag cggccatttt ccaccatgat attcggcaag caggcatcgc    2880
cgtgggtcac gacgagatcc tcgccgtcgg catacgcgc cttgagcctg gcgaacagtt    2940
cggctggcgc gagcccctga tgctcttcgt ccagatcatc ctgatcgaca agaccggctt    3000
ccatccgagt acgtgctcgc tcgatgcgat gtttcgcttg gtggtcgaat gggcaggtag    3060
ccggatcaag cgtatgcagc cgccgcattg catcagccat gatggatact ttctcggcag    3120
gagcaaggtg agatgacagg agatcctgcc ccggcacttc gcccaatagc agccagtccc    3180
ttcccgcttc agtgacaacg tcgagcacag ccgcgcaagg aacgcccgtc gtggccagcc    3240
acgatagccg cgctgcctcg tcttgcagtt cattcagggc accggacagg tcggtcttga    3300
caaaaagaac cgggcgaccc tgcgctgaca gccggaacac ggcggcatca gagcagccga    3360
ttgtctgttg tgcccagtca tagccgaata gcctctccac ccaagccgcc ggagaacctg    3420
cgtgcaatcc atcttgttca atcatgcgaa acgatcctca tcctgtctct tgatcagatc    3480
ttgatcccct gcgccatcag atccttggcg gcaagaaagc catccagttt actttgcagg    3540
gcttcccaac cttaccagag ggcggcccaa ctggcaattc c                       3581
```

<210> SEQ ID NO 64
<211> LENGTH: 4263
<212> TYPE: DNA
<213> ORGANISM: Artificial Sequence
<220> FEATURE:
<223> OTHER INFORMATION: pPh110 synthetic cloning vector

<400> SEQUENCE: 64

```
gacgtctgtg caagtactac tgttctgcag tccctatcag tgatagagat tgacatccct     60
atcagtgata gagatactga gcacatcagc aggacgcact gaccggtacc ctataagtta    120
cacaacataa ggaggaatat aatgcgtcgt cgtccgcgtc cgccgtacct gccgcgtccg    180
cgtccgccgc cgttcttccc gccgcgtctg ccgccgcgta tcccgccggg tttcccgccg    240
cgtttcccgc cgcgtttccc gtaaccgcgg agtatttgta cattctatca aagtatcata    300
aggaggagaa taatgcgtcg tcgtccgcgt ccgccgtacc tgccgcgtcc gcgtccgccg    360
ccgttcttcc cgccgcgtct gccgccgcgt atcccgccgg gtttcccgcc gcgtttcccg    420
ccgcgtttcc cgtaaggatc ccgagaattg gcttggactc ctgttgatag atccagtaat    480
gacctcagaa ctccatctgg atttgttcag aacgctcggt tgccgccggg cgtttttttat    540 tggtgagaat ccaagcagta gtcagaattc gatacccagc tgggtggagt gcaccaagga    600
gcatgcgaag gaaacgtttc gcagaagctt tccctatcag tgatagagat tgacatccct    660
atcagtgata gagatactga gcacatcagc aggacgcact gaccggtacc caacagggat    720
tcgttaattt aaggaggtct ccaaatgggc aacaaccgcc cggtgtatat tccgcagccg    780
cgcccgccgc atccgcgcat ttaaccgcgg agtatttgta cagaggtaca actcaactaa    840
tataaggagg ttcaaaatgg gcaacaaccg cccggtgtat attccgcagc cgcgcccgcc    900
```

```
gcatccgcgc atttaaggat cccgagaatt ggcttggact cctgttgata gatccagtaa    960
tgacctcaga actccatctg gatttgttca gaacgctcgg ttgccgccgg gcgttttta    1020
ttggtgagaa tccaagcagt agtcagagct cggactgctt aagtccctat cagtgataga   1080
gattgacatc cctatcagtg atagagatac tgagcacatc agcaggacgc actgaccggt   1140
acccaagaag atagaggagg taatatacaa gagaatgaac accctgccgg atacccatgt   1200
gcgcgaagcg agccgctgcc cgagcccggt gaccatttgg cagaccctgc tgacccgcct   1260
gctggatcag cattatggcc tgaccctgaa cgatacccccg tttgcggatg aacgtgtgat   1320
tgaacagcat attgaagcgg gcattagcct gtgcgatgcg gtgaacttc tggtggaaaa    1380
ataaccgcgg agtatttgta caagcctaac ggaagtcgac tagtaaggag aactaaatga   1440
acaccctgcc ggatacccat gtgcgcgaag cgagccgctg cccgagcccg gtgaccattt   1500
ggcagaccct gctgacccgc ctgctggatc agcattatgg cctgaccctg aacgataccc   1560
cgtttgcgga tgaacgtgtg attgaacagc atattgaagc gggcattagc ctgtgcgatg   1620
cggtgaactt tctggtggaa aaataaggat cccgagaatt ggcttggact cctgttgata   1680
gatccagtaa tgacctcaga actccatctg gatttgttca gaacgctcgg ttgccgccgg   1740
gcgttttta ttggtgagaa tccaagcagt agtcacaatt gtccccccggc gccagggttg    1800
atatctatcg ccctagggac cgtctcgaga gcgccctgta gcggcgcatt aagcgcggcg   1860
ggtgtggtgg ttacgcgcag cgtgaccgct acacttgcca gcgccctagc gcccgctcct   1920
ttcgctttct tcccttcctt tctcgccacg ttcgccggct ttccccgtca gctctaaat   1980
cgggggctcc ctttagggtt ccgatttagt gctttacggc acctcgaccc caaaaaactt   2040
gattagggtg atggttcacg tagtgggcca tcgccctgat agacggtttt tcgcccttg    2100
acgttggagt ccacgttctt taatagtgga ctcttgttcc aaactggaac aacactcaac   2160
cctatctcgg tctattcttt tgatttataa gggattttgc cgatttcggc ctattggtta   2220
aaaaatgagc tgatttaaca aaaatttaac gcgaattaaa tattaatcca acgcgtggca   2280
tcaaataaaa cgaaaggctc agtcgaaaga ctgggccttt cgttttatct gttgtttgtc   2340
ggtgaacgct ctcctgagta ggacaaatcc gccgccctag acttaggcgt tcggctgcgg   2400
cgagcggtat cagctcactc aaaggcggta atacggttat ccacagaatc aggggataac   2460
gcaggaaaga acatgtgagc aaaaggccag caaaaggcca ggaaccgtaa aaaggccgcg   2520
ttgctggcgt ttttccatag gctccgcccc cctgacgagc atcacaaaaa tcgacgctca   2580
agtcagaggt ggcgaaaccc gacaggacta taaagatacc aggcgtttcc ccctggaagc   2640
tccctcgtgc gctctcctgt tccgaccctg ccgcttaccg gatacctgtc cgcctttctc   2700
ccttcgggaa gcgtggcgct ttctcatagc tcacgctgta ggtatctcag ttcggtgtag   2760
gtcgttcgct ccaagctggg ctgtctgcac gaacccccccg ttcagcccga ccgctgcgcc   2820
ttatccggta actatcgtct tgagtccaac ccggtaagac acgacttatc gccactggca   2880
gcagccactg gtaacaggat tagcagagcg aggtatgtag gcggtgctac agagttcttg   2940
aagtggtggc ctaactacgg ctacactaga aggacagtat ttggtatctg cgctctgctg   3000
aagccagtta ccttcggaaa aagagttggt agctcttgat ccggcaaaca aaccaccgct   3060
ggtagcggtg gttttttgt ttgcaagcag cagattacgc gcagaaaaaa aggatctcaa   3120
gaagatcctt tgatctttc tacggggtct gacgctcagt ggaacgaaaa ctcacgttaa   3180
gggattttgg tcatgctag tgcttggatt ctcaccaata aaaaacgccc ggcggcaacc   3240
gagcgttctg aacaaatcca gatggagttc tgaggtcatt actggatcta tcaacaggag   3300
```

```
tccaagccaa ttctcgaacc ccagagtccc gctcagaaga actcgtcaag aaggcgatag    3360
aaggcgatgc gctgcgaatc gggagcggcg ataccgtaaa gcacgaggaa gcggtcagcc    3420
cattcgccgc caagctcttc agcaatatca cgggtagcca acgctatgtc ctgatagcgg    3480
tccgccacac ccagccggcc acagtcgatg aatccagaaa agcggccatt ttccaccatg    3540
atattcggca agcaggcatc gccgtgggtc acgacgagat cctcgccgtc gggcatacgc    3600
gccttgagcc tggcgaacag ttcggctggc gcgagcccct gatgctcttc gtccagatca    3660
tcctgatcga caagaccggc ttccatccga gtacgtgctc gctcgatgcg atgtttcgct    3720
tggtggtcga atgggcaggt agccggatca agcgtatgca gccgccgcat tgcatcagcc    3780
atgatggata ctttctcggc aggagcaagg tgagatgaca ggagatcctg ccccggcact    3840
tcgcccaata gcagccagtc ccttcccgct tcagtgacaa cgtcgagcac agccgcgcaa    3900
ggaacgcccg tcgtggccag ccacgatagc cgcgctgcct cgtcttgcag ttcattcagg    3960
gcaccggaca ggtcggtctt gacaaaaaga accgggcgac cctgcgctga cagccggaac    4020
acggcggcat cagagcagcc gattgtctgt tgtgcccagt catagccgaa tagcctctcc    4080
acccaagccg ccgagaaacc tgcgtgcaat ccatcttgtt caatcatgcg aaacgatcct    4140
catcctgtct cttgatcaga tcttgatccc ctgcgccatc agatccttgg cggcaagaaa    4200
gccatccagt ttactttgca gggcttccca accttaccag agggcggccc aactggcaat    4260
tcc                                                                   4263

<210> SEQ ID NO 65
<211> LENGTH: 4461
<212> TYPE: DNA
<213> ORGANISM: Artificial Sequence
<220> FEATURE:
<223> OTHER INFORMATION: pPh112 synthetic cloning vector

<400> SEQUENCE: 65
gacgtctgtg caagtactac tgttctgcag tccctatcag tgatagagat tgacatccct      60
atcagtgata gagatactga gcacatcagc aggacgcact gaccggtacc ctataagtta     120
cacaacataa ggaggaatat aatgcgtcgt cgtccgcgtc cgccgtacct gccgcgtccg     180
cgtccgccgc cgttcttccc gccgcgtctg ccgccgcgta tccgccgggg tttcccgccg     240
cgtttcccgc cgcgttttcc cgtaaccgcg gagtatttgta cattctatca aagtatcata     300
aggaggagaa taatgcgtcg tcgtccgcgt ccgccgtacc tgccgcgtcc gcgtccgccg     360
ccgttcttcc cgccgcgtct gccgccgcgt atccgccggg gtttcccgcc gcgtttcccg     420
ccgcgtttcc cgtaaggatc ccgagaattg gcttggactc ctgttgatag atccagtaat     480
gacctcagaa ctccatctgg atttgttcag aacgctcggt tgccgccggg cgttttttat     540
tggtgagaat ccaagcagta gtcagaattc gatacccagc tgggtggagt gcaccaagga     600
gcatgcgaag gaaacgtttc gcagaagctt tccctatcag tgatagagat tgacatccct     660
atcagtgata gagatactga gcacatcagc aggacgcact gaccggtacc caacagggat     720
tcgttaattt aaggaggtct ccaaatgggc aacaaccgcc cggtgtatat tccgcagccg     780
cgcccgccgc atccgcgcat ttaaccgcgg agtatttgta cagaggtaca actcaactaa     840
tataaggagg ttcaaaatgg caacaaccg cccggtgtat attccgcagc cgcgcccgcc     900
gcatccgcgc atttaaggat cccgagaatt ggcttggact cctgttgata gatccagtaa     960
tgacctcaga actccatctg gatttgttca gaacgctcgg ttgccgccgg gcgttttta    1020
```

```
ttggtgagaa tccaagcagt agtcagagct cggactgctt aagtccctat cagtgataga   1080
gattgacatc cctatcagtg atagagatac tgagcacatc agcaggacgc actgaccggt   1140
acctcacaat caaatctaag gagttacaaa tgaccgcgta tattctgacc gctgaagcgg   1200
aagcggatct gcgcggcatt attcgctata cccgccgcga atggggcgcg cgcaggtgc    1260 gccgctatat tgcgaaactg aacagggca ttgcgcgcct ggcggcgggc gaaggcccgt    1320
ttaaagatat gagcgaactg tttccggcgc tgcgcatggc gcgctgcgaa catcattatg   1380
tgttttgcct gccgcgcgcg ggcgaaccgg cgctggtggt ggcgattctg catgaacgca   1440
tggatctgat gacccgcctg gcggatcgcc tgaaaggcta accgcggagt atttgtacat    1500
acactatatt aacctaaaaa ggagcgtaac gaatgaccgc gtatattctg accgctgaag   1560
cggaagcgga tctgcgcggc attattcgct atacccgccg cgaatggggc gcggcgcagg   1620
tgcgccgcta tattgcgaaa ctggaacagg gcattgcgcg cctggcggcg ggcgaaggcc   1680
cgtttaaaga tatgagcgaa ctgtttccgg cgctgcgcat ggcgcgctgc gaacatcatt   1740
atgtgttttg cctgccgcgc gcgggcgaac cggcgctggt ggtggcgatt ctgcatgaac   1800
gcatggatct gatgacccgc ctggcggatc gcctgaaagg ctaaggatcc cgagaattgg   1860
cttggactcc tgttgataga tccagtaatg acctcagaac tccatctgga tttgttcaga   1920
acgctcggtt ccgccgggc gttttttatt ggtgagaatc caagcagtag tcacaattgt    1980
cccccggcgc cagggttgat atctatcgcc ctagggaccg tctcgagagc ccctgtagc    2040 ggcgcattaa gcgcggcggg tgtggtggtt acgcgcagcg tgaccgctac acttgccagc   2100
gccctagcgc ccgctccttt cgcttctttc ccttcctttc tcgccacgtt cgccggcttt   2160
ccccgtcaag ctctaaatcg ggggctccct ttagggttcc gatttagtgc tttacggcac   2220
ctcgacccca aaaaacttga ttagggtgat ggttcacgta gtgggccatc gccctgatag   2280 acggttttc gccctttgac gttggagtcc acgttcttta atagtggact cttgttccaa    2340 actgaacaa cactcaaccc tatctcggtc tattcttttg atttataagg gattttgccg    2400
atttcggcct attggttaaa aaatgagctg atttaacaaa aatttaacgc gaattaaata   2460
ttaatccaac gcgtggcatc aaataaaacg aaaggctcag tcgaaagact gggcctttcg   2520
ttttatctgt tgtttgtcgg tgaacgctct cctgagtagg acaaatccgc cgccctagac   2580
ttaggcgttc ggctgcggcg agcggtatca gctcactcaa aggcggtaat acggttatcc   2640
acagaatcag gggataacgc aggaaagaac atgtgagcaa aaggccagca aaaggccagg   2700
aaccgtaaaa aggccgcgtt gctggcgttt ttccataggc tccgcccccc tgacgagcat   2760
cacaaaaatc gacgctcaag tcagaggtgg cgaaacccga caggactata agataccag    2820 gcgtttcccc ctggaagctc cctcgtgcgc tctcctgttc cgaccctgcc gcttaccgga   2880
tacctgtccg ccttctccc ttcgggaagc gtggcgcttt ctcatagctc acgctgtagg    2940
tatctcagtt cggtgtaggt cgttcgctcc aagctgggct gtctgcacga accccccgtt   3000
cagcccgacc gctgcgcctt atccggtaac tatcgtcttg agtccaaccc ggtaagacac   3060
gacttatcgc cactggcagc agccactggt aacaggatta gcagagcgag gtatgtaggc   3120
ggtgctacag agttcttgaa gtggtggcct aactacggct acactagaag gacagtattt   3180
ggtatctgcg ctctgctgaa gccagttacc ttcggaaaaa gagttggtag ctcttgatcc   3240
ggcaaacaaa ccaccgctgg tagcggtggt ttttttgttt gcaagcagca gattacgcgc   3300
agaaaaaaag gatctcaaga agatcctttg atcttttcta cggggtctga cgctcagtgg   3360
aacgaaaact cacgttaagg gattttggtc atggctagtg cttggattct caccaataaa   3420
```

```
aaacgcccgg cggcaaccga gcgttctgaa caaatccaga tggagttctg aggtcattac   3480
tggatctatc aacaggagtc caagccaatt ctcgaacccc agagtcccgc tcagaagaac   3540
tcgtcaagaa ggcgatagaa ggcgatgcgc tgcgaatcgg gagcggcgat accgtaaagc   3600
acgaggaagc ggtcagccca ttcgccgcca agctcttcag caatatcacg ggtagccaac   3660
gctatgtcct gatagcggtc cgccacaccc agccggccac agtcgatgaa tccagaaaag   3720
cggccatttt ccaccatgat attcggcaag caggcatcgc cgtgggtcac gacgagatcc   3780
tcgccgtcgg catacgcgc cttgagcctg gcgaacagtt cggctggcgc gagcccctga   3840
tgctcttcgt ccagatcatc ctgatcgaca agaccggctt ccatccgagt acgtgctcgc   3900
tcgatgcgat gtttcgcttg gtggtcgaat gggcaggtag ccggatcaag cgtatgcagc   3960
cgccgcattg catcagccat gatggatact ttctcggcag gagcaaggtg agatgacagg   4020
agatcctgcc ccggcacttc gcccaatagc agccagtccc ttcccgcttc agtgacaacg   4080
tcgagcacag ccgcgcaagg aacgcccgtc gtggccagcc acgatagccg cgctgcctcg   4140
tcttgcagtt cattcagggc accggacagg tcggtcttga caaaaagaac cgggcgaccc   4200
tgcgctgaca gccggaacac ggcggcatca gagcagccga ttgtctgttg tgcccagtca   4260
tagccgaata gcctctccac ccaagccgcc ggagaacctg cgtgcaatcc atcttgttca   4320
atcatgcgaa acgatcctca tcctgtctct tgatcagatc ttgatcccct gcgccatcag   4380
atccttggcg gcaagaaagc catccagttt actttgcagg gcttcccaac cttaccagag   4440
ggcggcccaa ctggcaattc c                                            4461

<210> SEQ ID NO 66
<211> LENGTH: 4447
<212> TYPE: DNA
<213> ORGANISM: Artificial Sequence
<220> FEATURE:
<223> OTHER INFORMATION: pPh113 synthetic cloning vector

<400> SEQUENCE: 66
gacgtctgtg caagtactac tgttctgcag tccctatcag tgatagagat tgacatccct     60
atcagtgata gagatactga gcacatcagc aggacgcact gaccggtacc ctataagtta    120
cacaacataa ggaggaatat aatgcgtcgt cgtccgcgtc cgccgtacct gccgcgtccg    180
cgtccgccgc cgttcttccc gccgcgtctg ccgccgcgta tccgccgggg tttcccgccg    240
cgtttcccgc cgcgtttccc gtaaccgcgg agtatttgta cattctatca aagtatcata    300
aggaggagaa taatgcgtcg tcgtccgcgt ccgccgtacc tgccgcgtcc gcgtccgccg    360
ccgttcttcc cgccgcgtct gccgccgcgt atccgccgg gtttcccgcc gcgtttcccg    420
ccgcgttccc cgtaaggatc ccgagaattg gcttggactc ctgttgatag atccagtaat    480
gacctcagaa ctccatctgg atttgttcag aacgctcggt tgccgccggg cgttttttat    540
tggtgagaat ccaagcagta gtcagaattc gatacccagc tgggtggagt gcaccaagga    600
gcatgcgaag gaaacgtttc gcagaagctt tccctatcag tgatagagat tgacatccct    660
atcagtgata gagatactga gcacatcagc aggacgcact gaccggtacc caacagggat    720
tcgttaattt aaggaggtct ccaaatgggc aacaaccgcc cggtgtatat tccgcagccg    780
cgcccgccgc atccgcgcat ttaaccgcgg agtatttgta cagaggtaca actcaactaa    840
tataaggagg ttcaaaatgg caacaaccg cccggtgtat attccgcagc cgcgcccgcc    900
gcatccgcgc atttaaggat cccgagaatt ggcttggact cctgttgata gatccagtaa    960
```

```
tgacctcaga actccatctg gatttgttca gaacgctcgg ttgccgccgg gcgttttta     1020 ttggtgagaa tccaagcagt agtcagagct cggactgctt aagtccctat cagtgataga    1080
gattgacatc cctatcagtg atagagatac tgagcacatc agcaggacgc actgaccggt    1140
acctatccat cattaacgac caaatcaagg aggacgtatg cagtttaagg tttacaccta    1200
taaaagagag agccgttatc gtctgtttgt ggatgtacag agtgatatta ttgacacgcc    1260
cgggcgacgg atggtgatcc ccctggccag tgcacgtctg ctgtcagata aagtctcccg    1320
tgaactttac ccggtggtgc atatcgggga tgaaagctgg cgcatgatga ccaccgatat    1380
ggccagtgtg ccggtctccg ttatcgggga agaagtggct gatctcagcc accgcgaaaa    1440
tgacatcaaa aacgccatta acctgatgtt ctggggaata taaccgcggt accaaccccc    1500
ctattagaat aaggagtatc acgcatgcag tttaaggttt acacctataa aagagagagc    1560
cgttatcgtc tgtttgtgga tgtacagagt gatattattg acacgcccgg cgacggatg    1620 gtgatccccc tggccagtgc acgtctgctg tcagataaag tctcccgtga actttacccg    1680
gtggtgcata tcggggatga aagctggcgc atgatgacca ccgatatggc cagtgtgccg    1740
gtctccgtta tcggggaaga agtggctgat ctcagccacc gcgaaaatga catcaaaaac    1800
gccattaacc tgatgttctg gggaatataa ggatcccgag aattggcttg gactcctgtt    1860
gatagatcca gtaatgacct cagaactcca tctggatttg ttcagaacgc tcggttgccg    1920
ccgggcgttt tttattggtg agaatccaag cagtagtcac aattgtcccc cggcgccagg    1980
gttgatatct atcgccctag gaccgtctc gagagcgccc tgtagcggcg cattaagcgc    2040
ggcgggtgtg gtggttacgc gcagcgtgac cgctacactt gccagcgccc tagcgcccgc    2100
tcctttcgct ttcttccctt cctttctcgc cacgttcgcc ggctttcccc gtcaagctct    2160
aaatcggggg ctcccttag ggttccgatt tagtgcttta cggcacctcg accccaaaaa     2220
acttgattag ggtgatggtt cacgtagtgg gccatcgccc tgatagacgg ttttttcgccc   2280 tttgacgttg gagtccacgt tctttaatag tggactcttg ttccaaactg gaacaacact    2340
caaccctatc tcggtctatt cttttgattt ataagggatt ttgccgattt cggcctattg    2400
gttaaaaaat gagctgattt aacaaaaatt taacgcgaat taaatattaa tccaacgcgt    2460
ggcatcaaat aaaacgaaag gctcagtcga agactgggc ctttcgtttt atctgttgtt     2520
tgtcggtgaa cgctctcctg agtaggacaa atccgccgcc ctagacttag cgttcggct    2580 gcggcgagcg gtatcagctc actcaaaggc ggtaatacgg ttatccacag aatcagggga    2640
taacgcagga aagaacatgt gagcaaaagg ccagcaaaag gccaggaacc gtaaaaaggc    2700
cgcgttgctg gcgttttttcc ataggctccg ccccctgac gagcatcaca aaaatcgacg    2760
ctcaagtcag aggtggcgaa acccgacagg actataaaga taccaggcgt ttccccctgg    2820
aagctccctc gtgcgctctc ctgttccgac cctgccgctt accggatacc tgtccgcctt    2880
tctcccttcg ggaagcgtgg cgctttctca tagctcacgc tgtaggtatc tcagttcggt    2940
gtaggtcgtt cgctccaagc tgggctgtct gcacgaaccc cccgttcagc ccgaccgctg    3000
cgccttatcc ggtaactatc gtcttgagtc caacccggta agacacgact tatcgccact    3060
ggcagcagcc actggtaaca ggattagcag agcgaggtat gtaggcggtg ctacagagtt    3120
cttgaagtgg tggcctaact acggctacac tagaaggaca gtatttggta tctgcgctct    3180
gctgaagcca gttaccttcg gaaaaagagt tggtagctct tgatccggca acaaaccac     3240 cgctggtagc ggtggttttt tgttgcaa gcagcagatt acgcgcagaa aaaaggatc      3300 tcaagaagat cctttgatct tttctacggg gtctgacgct cagtggaacg aaaactcacg    3360
```

-continued

```
ttaagggatt tggtcatgg ctagtgcttg gattctcacc aataaaaaac gcccggcggc    3420
aaccgagcgt tctgaacaaa tccagatgga gttctgaggt cattactgga tctatcaaca    3480
ggagtccaag ccaattctcg aaccccagag tcccgctcag aagaactcgt caagaaggcg    3540
atagaaggcg atgcgctgcg aatcgggagc ggcgataccg taaagcacga ggaagcggtc    3600
agcccattcg ccgccaagct cttcagcaat atcacgggta gccaacgcta tgtcctgata    3660
gcggtccgcc acacccagcc ggccacagtc gatgaatcca gaaaagcggc cattttccac    3720
catgatattc ggcaagcagg catcgccgtg ggtcacgacg agatcctcgc cgtcgggcat    3780
acgcgccttg agcctggcga acagttcggc tggcgcgagc ccctgatgct cttcgtccag    3840
atcatcctga tcgacaagac cggcttccat ccgagtacgt gctcgctcga tgcgatgttt    3900
cgcttggtgg tcgaatgggc aggtagccgg atcaagcgta tgcagccgcc gcattgcatc    3960
agccatgatg gatactttct cggcaggagc aaggtgagat gacaggagat cctgccccgg    4020
cacttcgccc aatagcagcc agtcccttcc cgcttcagtg acaacgtcga gcacagccgc    4080
gcaaggaacg cccgtcgtgg ccagccacga tagccgcgct gcctcgtctt gcagttcatt    4140
cagggcaccg gacaggtcgg tcttgacaaa aagaaccggg cgaccctgcg ctgacagccg    4200
gaacacggcg gcatcagagc agccgattgt ctgttgtgcc cagtcatagc cgaatagcct    4260
ctccacccaa gccgccggag aacctgcgtg caatccatct tgttcaatca tgcgaaacga    4320
tcctcatcct gtctcttgat cagatcttga tcccctgcgc catcagatcc ttggcggcaa    4380
gaaagccatc cagtttactt tgcagggctt cccaacctta ccagagggcg gcccaactgg    4440
caattcc                                                            4447
```

<210> SEQ ID NO 67
<211> LENGTH: 4619
<212> TYPE: DNA
<213> ORGANISM: Artificial Sequence
<220> FEATURE:
<223> OTHER INFORMATION: pPh115 synthetic cloning vector

<400> SEQUENCE: 67

```
gacgtctgtg caagtactac tgttctgcag tccctatcag tgatagagat tgacatccct      60
atcagtgata gagatactga gcacatcagc aggacgcact gaccggtacc ctataagtta     120
cacaacataa ggaggaatat aatgcgtcgt cgtccgcgtc cgccgtacct gccgcgtccg     180
cgtccgccgc cgttcttccc gccgcgtctg ccgccgcgta tcccgccggg tttcccgccg     240
cgtttcccgc cgcgttttcc cgtaaccgcg agtatttgta cattctatca aagtatcata     300
aggaggagaa taatgcgtcg tcgtccgcgt ccgccgtacc tgccgcgtcc gcgtccgccg     360
ccgttcttcc cgccgcgtct gccgccgcgt atcccgccgg gtttcccgcc gcgtttcccg     420
ccgcgtttcc cgtaaggatc ccgagaattg gcttggactc ctgttgatag atccagtaat     480
gacctcagaa ctccatctgg atttgttcag aacgctcggt tgccgccggg cgttttttat     540
tggtgagaat ccaagcagta gtcagaattc gatacccagc tgggtggagt gcaccaagga     600
gcatgcgaag gaaacgtttc gcagaagctt tccctatcag tgatagagat tgacatccct     660
atcagtgata gagatactga gcacatcagc aggacgcact gaccggtacc caacagggat     720
tcgttaattt aaggaggtct ccaaatgggc aacaaccgcc cggtgtatat tccgcagccg     780
cgcccgccgc atccgcgcat ttaaccgcgg agtatttgta cagaggtaca actcaactaa     840
tataaggagg ttcaaaatgg gcaacaaccg cccggtgtat attccgcagc cgcgcccgcc     900
```

```
gcatccgcgc atttaaggat cccgagaatt ggcttggact cctgttgata gatccagtaa    960
tgacctcaga actccatctg gatttgttca gaacgctcgg ttgccgccgg gcgtttttta   1020
ttggtgagaa tccaagcagt agtcagagct cggactgctt aagtccctat cagtgataga   1080
gattgacatc cctatcagtg atagagatac tgagcacatc agcaggacgc actgaccggt   1140
acctatccat cattaacgac caaatcaagg aggacgtatg cagtttaagg tttacaccta   1200
taaaagagag agccgttatc gtctgtttgt ggatgtacag agtgatatta ttgacacgcc   1260
cgggcgacgg atggtgatcc ccctggccag tgcacgtctg ctgtcagata aagtctcccg   1320
tgaactttac ccggtggtgc atatcgggga tgaaagctgg cgcatgatga ccaccgatat   1380
ggccagtgtg ccggtctccg ttatcgggga agaagtggct gatctcagcc accgcgaaaa   1440
tgacatcaaa aacgccatta acctgatgtt ctggggaata taaggatccc gagaattggc   1500
ttggactcct gttgatagat ccagtaatga cctcagaact ccatctggat tgttcagaa    1560
cgctcggttg ccgccgggcg ttttttattg gtgagaatcc aagcagtagt caggcgcctc   1620
cctatcagtg atagagattg acatccctat cagtgataga gatactgagc acatcagcag   1680
gacgcactga ccggtaccta tccatcatta cgaccaaat caaggaggac gtatgcagtt    1740
taaggtttac acctataaaa gagagagccg ttatcgtctg tttgtggatg tacagagtga   1800
tattattgac acgccgggc gacggatggt gatccccctg ccagtgcac gtctgctgtc     1860
agataaagtc tcccgtgaac tttacccggt ggtgcatatc ggggatgaaa gctggcgcat   1920
gatgaccacc gatatggcca gtgtgccggt ctccgttatc ggggaagaag tggctgatct   1980
cagccaccgc gaaaatgaca tcaaaaacgc cattaacctg atgttctggg gaatataagg   2040
atcccgagaa ttggcttgga ctcctgttga tagatccagt aatgacctca gaactccatc   2100
tggatttgtt cagaacgctc ggttgccgcc gggcgttttt tattggtgag aatccaagca   2160
gtagtcacct agggaccgtc tcgagagcgc cctgtagcgg cgcattaagc gcggcgggtg   2220
tggtggttac gcgcagcgtg accgctacac ttgccagcgc cctagcgccc gctcctttcg   2280
ctttcttccc ttcctttctc gccacgttcg ccggctttcc ccgtcaagct ctaaatcggg   2340
ggctcccttt agggttccga tttagtgctt tacggcacct cgaccccaaa aaacttgatt   2400
agggtgatgg ttcacgtagt gggccatcgc cctgatagac ggttttcgc cctttgacgt    2460
tggagtccac gttctttaat agtggactct gttccaaac tggaacaaca ctcaacccta    2520
tctcggtcta ttcttttgat ttataaggga ttttgccgat ttcggcctat tggttaaaaa   2580
atgagctgat ttaacaaaaa tttaacgcga ttaaatatt aatccaacgc gtggcatcaa    2640
ataaaacgaa aggctcagtc gaaagactgg gcctttcgtt ttatctgttg tttgtcggtg   2700
aacgctctcc tgagtaggac aaatccgccg ccctagactt aggcgttcgg ctgcggcgag   2760
cggtatcagc tcactcaaag gcggtaatac ggttatccac agaatcaggg gataacgcag   2820
gaaagaacat gtgagcaaaa ggccagcaaa aggccaggaa ccgtaaaaag gccgcgttgc   2880
tggcgttttt ccataggctc cgcccccctg acgagcatca caaaaatcga cgctcaagtc   2940
agaggtggcg aaacccgaca ggactataaa gataccaggc gtttccccct ggaagctccc   3000
tcgtgcgctc tcctgttccg accctgccgc ttaccggata cctgtccgcc tttctccctt   3060
cgggaagcgt ggcgctttct catagctcac gctgtaggta tctcagttcg gtgtaggtcg   3120
ttcgctccaa gctgggctgt ctgcacgaac cccccgttca gcccgaccgc tgcgccttat   3180
ccggtaacta tcgtcttgag tccaacccgg taagacacga cttatcgcca ctggcagcag   3240
ccactggtaa caggattagc agagcgaggt atgtaggcgg tgctacagag ttcttgaagt   3300
```

```
ggtggcctaa ctacggctac actagaagga cagtatttgg tatctgcgct ctgctgaagc    3360
cagttacctt cggaaaaaga gttggtagct cttgatccgg caaacaaacc accgctggta    3420
gcggtggttt ttttgtttgc aagcagcaga ttacgcgcag aaaaaaagga tctcaagaag    3480
atcctttgat cttttctacg gggtctgacg ctcagtggaa cgaaaactca cgttaaggga    3540
ttttggtcat ggctagtgct tggattctca ccaataaaaa acgcccggcg gcaaccgagc    3600
gttctgaaca aatccagatg gagttctgag gtcattactg gatctatcaa caggagtcca    3660
agccaattct cgaacccag agtcccgctc agaagaactc gtcaagaagg cgatagaagg    3720
cgatgcgctg cgaatcggga gcggcgatac cgtaaagcac gaggaagcgg tcagcccatt    3780
cgccgccaag ctcttcagca atatcacggg tagccaacgc tatgtcctga tagcggtccg    3840
ccacacccag ccggccacag tcgatgaatc cagaaaagcg gccatttcc accatgatat    3900 tcggcaagca ggcatcgccg tgggtcacga cgagatcctc gccgtcgggc atacgcgcct    3960
tgagcctggc gaacagttcg gctggcgcga gccctgatg ctcttcgtcc agatcatcct    4020
gatcgacaag accggcttcc atccgagtac gtgctcgctc gatgcgatgt ttcgcttggt    4080
ggtcgaatgg gcaggtagcc ggatcaagcg tatgcagccg ccgcattgca tcagccatga    4140
tggatacttt ctcggcagga gcaaggtgag atgacaggag atcctgcccc ggcacttcgc    4200
ccaatagcag ccagtccctt cccgcttcag tgacaacgtc gagcacagcc gcgcaaggaa    4260
cgcccgtcgt ggccagccac gatagccgcg ctgcctcgtc ttgcagttca ttcagggcac    4320
cggacaggtc ggtcttgaca aaaagaaccg ggcgaccctg cgctgacagc cggaacacgg    4380
cggcatcaga gcagccgatt gtctgttgtg cccagtcata gccgaatagc ctctccaccc    4440
aagccgccgg agaacctgcg tgcaatccat cttgttcaat catgcgaaac gatcctcatc    4500
ctgtctcttg atcagatctt gatccctgc gccatcagat ccttggcggc aagaaagcca    4560
tccagtttac tttgcagggc ttcccaacct taccagaggg cggcccaact ggcaattcc    4619
```

ENGINEERED PHAGEMIDS

FEDERALLY SPONSORED RESEARCH

This invention was made with government support under HDTRA1-14-1-0006 and HDTRA1-15-1-0040 awarded by the Defense Threat Reduction Agency (DTRA). The government has certain rights in the invention.

RELATED APPLICATION

This application is a national stage filing under 35 U.S.C. 371 of International Patent Application No. PCT/US2015/064020, filed Dec. 4, 2015, the contents of which is incorporated herein by reference in its entirety.

BACKGROUND

The increasing incidence of antibiotic-resistant bacterial infections is creating a global public health threat. Since conventional antibiotic drug discovery has failed to keep pace with the rise of resistance, a growing need exists to develop novel antibacterial methodologies. Replication-competent bacteriophages have been utilized in a limited fashion to treat bacterial infections.

SUMMARY

Current approaches to treating bacterial infections can result in the release of harmful endotoxins, leading to untoward side effects. Provided herein, are engineered bacterial phagemids that express antimicrobial peptides (AMPs) and protein toxins that disrupt intracellular processes, leading to rapid, non-lytic bacterial death. This method is highly modular, enabling one to readily alter the number and type of AMPs and toxins encoded by the phagemids. Furthermore, results provided herein show the effectiveness of engineered phagemids in an in vivo murine peritonitis infection model. Targeted, engineered phagemid therapy of the present disclosure can serve as a viable, non-antibiotic means to treat bacterial infections, while avoiding the health issues inherent to lytic and replicative bacteriophage use.

Some embodiments of the present disclosure provide engineered phagemids that comprise at least one synthetic genetic circuit, wherein the at least one synthetic generic circuit comprises a nucleic acid (containing gene sequences) encoding at least one non-lytic antimicrobial peptides (AMPs) and/or antibacterial toxin proteins, an origin of replication, and a bacteriophage-packaging signal, wherein the engineered phagemid does not comprise some or all gene sequences encoding bacteriophage proteins required for assembly of a bacteriophage particle. In some embodiments, the phagemids do not comprise any gene sequences encoding bacteriophage proteins required for assembly of a bacteriophage particle. In some embodiments, the origin of replication is the same as the bacteriophage-packaging signal. For example, F1 origin of replication can function as a packaging signal.

Also provided herein are phagemid particles and compositions comprising a (at least one) engineered phagemid of the present disclosure as well as composition comprising the phagemid particle(s).

Some embodiments of the present disclosure provide methods of treating a bacterial infection using at least one of the recombinant phagemids, phagemid particles or compositions as provided herein. In some embodiments, the methods comprise administering to a subject in need of treatment of a bacterial infection an effective amount of a recombinant phagemid, a phagemid particle or a composition as provided herein.

Also provided herein are phagemid systems comprising the engineered phagemid of claim 1, and a plasmid comprising a phagemid helper system that expresses bacteriophage proteins required for assembly of a bacteriophage particle, wherein the plasmid is not packaged in the bacteriophage particle. Some embodiments, provide a bacterial cell comprising such a phagemid system.

BRIEF DESCRIPTION OF THE DRAWINGS

The accompanying drawings are not intended to be drawn to scale. For purposes of clarity, not every component may be labeled in every drawing.

FIGS. 4A-4C show an example of modulation of AMP networks and enhancement by toxin networks. (A) Phagemids carrying synthetic networks that express combinations of cecropin and apidaecin antibacterial peptides were tested against EMG2 E. coli for their ability to cause bacterial death. These phagemid networks were designated $\phi_I$, $\phi_{II}$, and $\phi_{III}$ respectively. (B) Three toxin networks, expressing ccdB, yeeV', or parE genes were designed under regulation of the $P_{LTetO}$ promoter. These networks were cloned into the MCS of the $\phi_{III}$ plasmid, and purified particles were screened against EMG2 E. coli for possible synergy with cecropin and apidaecin networks. Purified phagemid particles were tested alongside $\phi_{III}$ particles for induction of bacterial death. (C) An overexpressing ccdB network was cloned into the MCS of the $\phi_{IV}$ plasmid. Purified phagemid particles were screened against EMG2 *E. coli* for their ability to cause non-lytic bacterial death. (D) Various final concentrations of $\phi_{III}$ and $\phi_{IV}$ phagemid particles were tested against target EMG2 bacteria. Bacterial cell viability was assessed 6 hours post infection.

DESCRIPTION

Antibiotic-resistant bacterial infections are an increasing concern in clinical and non-clinical settings. Current first-line treatments rely upon the administration of small-molecule antibiotics to induce bacterial cell death. These broad-spectrum treatments disrupt the patient's normal microflora, allowing resistant bacteria and fungal pathogens to take advantage of vacated niches. Bacteriophages offer several distinct advantages over traditional antibiotic treatment, including high bacterial target specificity and reduced collateral damage to the host microbiota. They also have the potential to deliver synthetic gene networks, which can be designed to disrupt bacterial structures and processes through the expression of antibacterial or sensitizing genes. Phage therapy has relied upon lytic bacteriophages, which cause bacterial cell death through the rupture of the bacterial cell membrane. However, bacterial lysis results in the release of expressed proteins and endotoxins into the surrounding environment. This in turn can lead to detrimental side effects, ranging from diarrhea to sepsis and even death.

Lysogenic bacteriophages, in contrast to their lytic counterparts, secrete mature bacteriophage particles without causing cellular lysis. Although lysogenic bacteriophages have been engineered to serve as adjuvants to antibiotics by overexpressing sensitizing proteins, their dependence upon antibiotics makes them inherently non-lethal and ineffective on their own. Lysogenic bacteriophage genomes become less reliable over time due to fluctuations in genome copy number as they become packaged into viral particles. Repeated infection-reinfection cycles can also render infected bacteria resistant to further bacteriophage infection as the target cell tries to escape superinfection, reducing the effect of repeated treatment. These limitations diminish the effectiveness of bacteriophage therapies as a viable treatment strategy.

Figure 6:
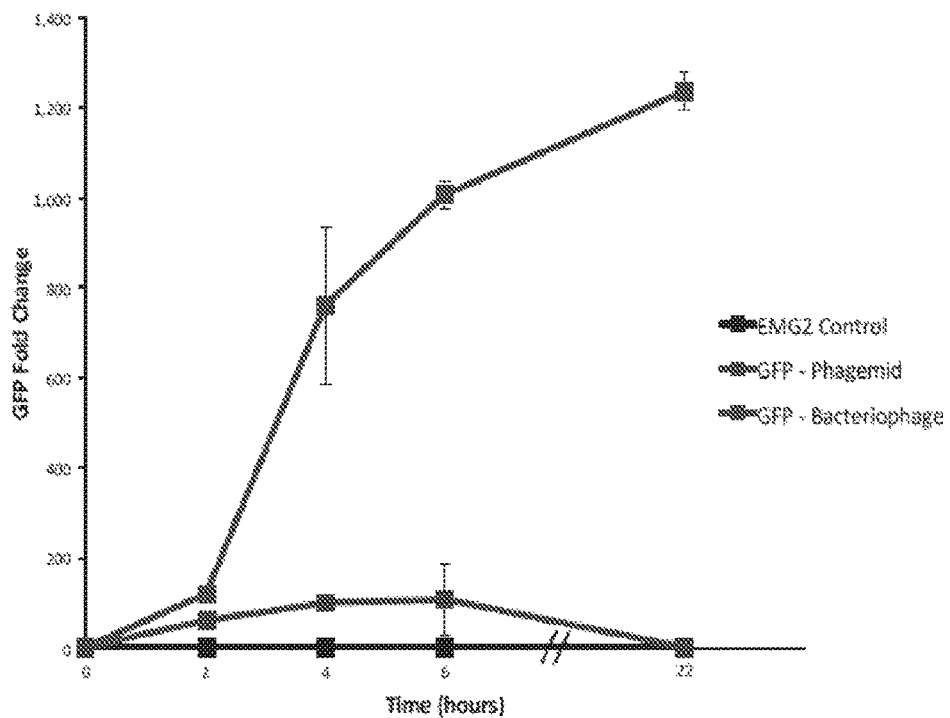
FIG. 6 shows gene expression by bacteriophage- and phagemid-delivered networks. Differences in synthetic network expression of a constitutive GFP-expressing network delivered by either the M13 bacteriophage or by its phagemid. Bacteriophage and phagemid particles carrying a constitutive GFP expression network were purified from liquid culture and used to infect EMG2 *E. coli*. Resulting GFP expression was tracked over time for fluorescence.

The present disclosure provides a modular bacterial phagemid system, which expresses a variety of non-lytic antimicrobial peptides (AMPs) and toxin proteins, to address the rising need for non-traditional, antibacterial treatment solutions. Phagemids, which employ bacteriophage proteins but selectively package a synthetic plasmid, provide a marked benefit over standard bacteriophage therapies, lytic and lysogenic alike. This system limits the serious side effects linked to lytic bacteriophage approaches and improves upon lysogenic therapies by allowing for the direct delivery of specific high-copy plasmids to target cells in a single round of infection, ensuring consistent network expression levels and long-term stability (FIG. 6).

The phagemid system as provided herein, in some embodiments, relies upon the expression of two plasmids: the first plasmid carries a bacteriophage-packaging signal and the desired antibacterial gene network, while the second plasmid contains a phagemid helper system (Chasteen L et al. *Nucleic Acids Research* 2006, 34 (21), e145-e145), which generates the bacteriophage proteins required for particle assembly but is not packaged itself. Together, these plasmids produce bacteriophage particles that selectively package an engineered plasmid harboring a synthetic gene network and a stable origin of replication rather than the bacteriophage genome. This approach allows for sustained network expression and reduces the formation of bacteriophage resistance by avoiding bacteriophage particle replication and superinfection in target cells, for example.

Figure 1:
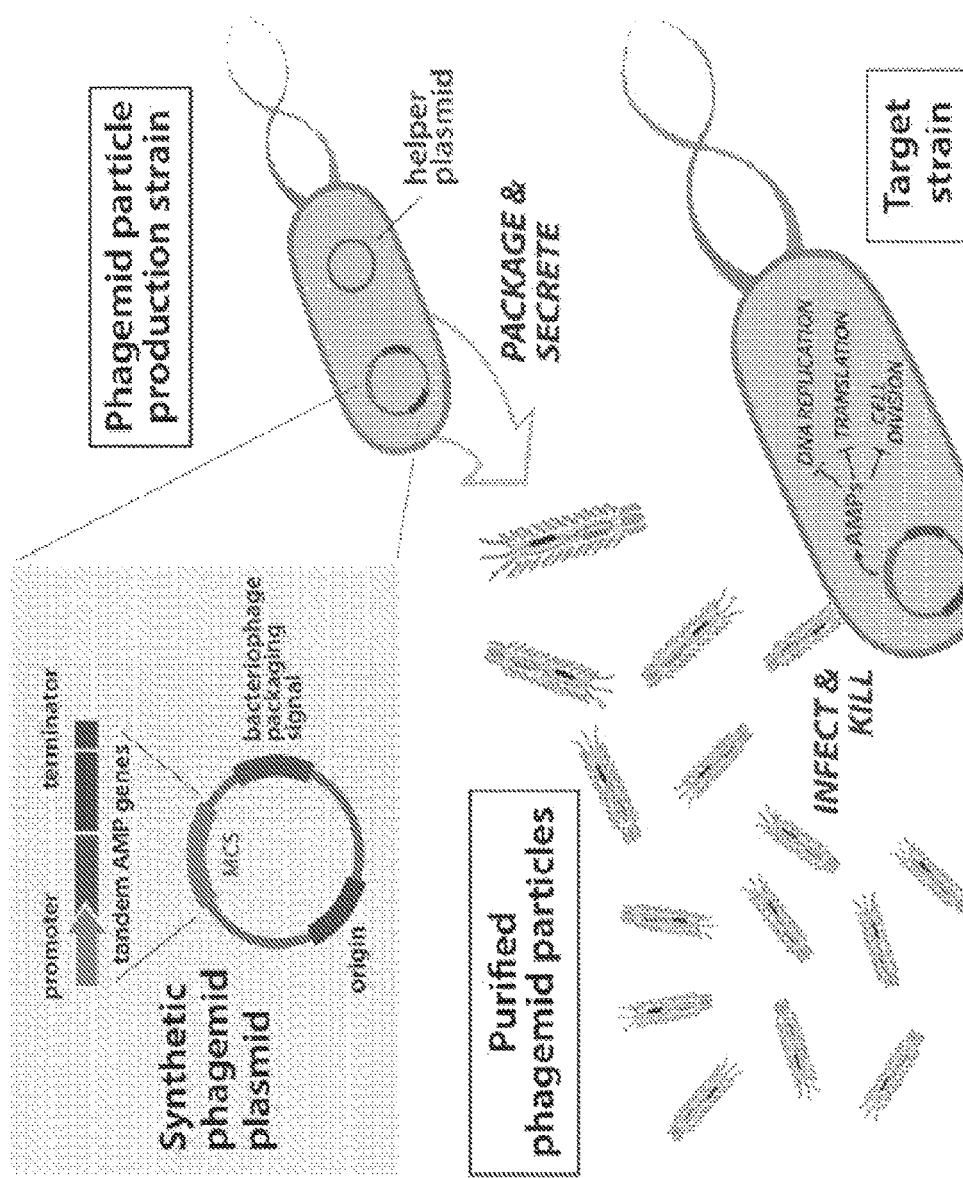
FIG. 1 shows an example of antibacterial phagemid construction. Phagemid plasmids, which carry an engineered antibacterial network, bacteriophage-packaging signal, and high-copy origin of replication, are first transformed into a production strain harboring a helper plasmid. Next, secreted phagemid particles are isolated from the production strain and purified. Resulting engineered phagemid particles are then used to infect target bacteria, causing expression of antibacterial proteins, which inhibit intracellular processes and cause non-lytic bacterial death.

This phagemid system is highly modular in part as due to a plug-and-play cloning platform (Litcofsky, K. D. et al. *Nature Methods* 2012, 9 (11), 1077-1080). This platform employs a high-copy plasmid that contains a large multiple cloning site (MCS) into which a range of engineered antibacterial networks were inserted along with the F1 origin of replication, which serves as the packaging signal for the M13 bacteriophage (Russel, M. et al. *Journal of Virology* 1989, 63 (8), 3284-3295). The fully constructed phagemid plasmid was then transformed into a production strain, carrying the M13cp phagemid helper plasmid. Phagemid particles produced by this strain were then used for single-round infection of the target *Escherichia coli* (*E. coli*) cells, leading to non-lytic bacterial cell death (FIG. 1).

Phagemids, Phagemid Particles and Phagemid Systems

A "phagemid" is a filamentous phage-derived vector containing the replication origin of a plasmid and the packaging signal of a bacteriophage. An "engineered phagemid" is a phagemid that does not occur in nature. An engineered phagemid may be recombinant or synthetic. A "recombinant" phagemid is constructed by joining nucleic acids (e.g., isolated nucleic acids, synthetic nucleic acids or a combination thereof). A "synthetic" phagemid is amplified, chemically synthesized, or synthesized by other means. In some embodiments, an engineered phagemid is a phagemid that has been modified by genetic or chemical means.

Examples of phagemids that may be used in accordance with the invention include, without limitation, M13-derived phagemids containing the F1 origin for filamentous phage packaging such as, for example, pBluescript II SK (+/−) and KS (+/−) phagemids, pBC SK and KS phagemids, pADL and P1-based phagemids (see, e.g., Westwater C A et al., *Microbiology* 148, 943-50 (2002); Kittleson J T et al., *ACS Synthetic Biology* 1, 583-89 (2012); Mead D A et al., *Biotechnology* 10, 85-102 (1988)). In some embodiments, a phagemid is an M13-derived phagemid. Other phagemids may be used in accordance with the present disclosure.

Engineered phagemids of the present disclosure, in some embodiments, comprise an origin of replication, which is a particular nucleotide sequence at which replication is initiated. In some embodiments, the origin of replication is an F1 origin of replication, which is derived from an F1 phage (a class I filamentous phage). Other origins of replication may be used in accordance with the present disclosure.

Engineered phagemids of the present disclosure, in some embodiments, comprise a bacteriophage-packaging signal, which is a cis-active region of a bacteriophage genome that signals the bacteriophage genome encapsidation.

Some embodiments of the present disclosure provide phagemid particles comprising an engineered phagemid. A "phagemid particle," as used herein, is a bacteriophage that contains an engineered phagemid but does not contain a bacteriophage genome. A bacteriophage is an obligate intracellular parasite that multiplies inside bacteria by making use of some or all of the host biosynthetic machinery. Though different phage may contain different materials, they all contain nucleic acid and protein, and may be covered by a lipid membrane. A bacteriophage genome typically consists of a single, linear or circular, double- or single-stranded nucleic acid. Depending on the phage, the nucleic acid can be either DNA or RNA.

In some embodiments, engineered phagemids do not comprise (lack, are free of) gene sequences encoding bacteriophage proteins required for assembly of a bacteriophage particle. Such genes vary among different types of bacteriophage. M13 bacteriophage, for example, is a filamentous bacteriophage composed of circular single stranded DNA (ssDNA) which is 6407 nucleotides long encapsulated in approximately 2700 copies of the major coat protein P8, and capped with 5 copies of two different minor coat proteins (P9, P6, P3) on the ends. The minor coat protein P3 attaches to the receptor at the tip of the F. pilus of the host Escherichia coli. The phage coat is primarily assembled from P8. Thus, in some embodiments, engineered phagemids do not comprise gene sequences encoding M13 P8. In some embodiments, engineered phagemids do not comprise gene sequences encoding M13 P8, P9. P6 or P3. In some embodiments, an engineered phagemid may comprise some, but not all, gene sequences encoding bacteriophage proteins required for assembly of a bacteriophage particle. For example, engineered phagemids may comprise 1, 2, 3 or more gene sequences encoding bacteriophage proteins required for assembly of a bacteriophage particle.

Engineered phagemids of the present disclosure, in some embodiments, comprise a multiple cloning site, which is a short segment of DNA containing many (e.g., 10-30) restriction sites. Restriction sites within an MCS are typically unique, occurring only once within a given phagemid.

Engineered phagemids of the present disclosure, in some embodiments, are considered high-copy-number phagemids. Copy number refers to the average or expected number of copies of the phagemid per host cell (e.g., bacterial cell). Copy number can depend on the origin of replication and its constituents, the size of the phagemid and the synthetic genetic circuit, and culture conditions (e.g., factors that influence the metabolic burden on the host cell). For high-copy-number phagemids, typically there are 500-700 copies per cell, although there may be more or less. For medium-copy-number phagemids, typically there are 20-100 copies for cell, and for low-copy-number phagemids, typically there are 15-20 copies per cell.

Some embodiments provide phagemid systems that comprise an engineered phagemid and a plasmid comprising a phagemid helper system that expresses bacteriophage proteins required for assembly of a bacteriophage particle, wherein the plasmid is not packaged in the bacteriophage particle. A phagemid helper system (Chasteen L et al. *Nucleic Acids Research* 2006, 34 (21), e145-e145, incorporated herein by reference) includes cell lines that contain M13-based helper plasmids that express phage packaging proteins, which assemble phagemid particles as efficiently as helper phage, but without helper phage contamination. Thus, phagemid systems, in some embodiments, comprise (a) an engineered phagemid that comprises at least one synthetic genetic circuit, wherein the at least one synthetic genetic circuit comprises gene sequences encoding at least one non-lytic antimicrobial peptides (AMPs) and/or antibacterial toxin proteins, a stable origin of replication, and a bacteriophage-packaging signal, wherein the engineered phagemid does not comprise some or all gene sequences encoding bacteriophage proteins required for assembly of a bacteriophage particle, and (b) a plasmid comprising nucleic acids that encode (or a phagemid helper system that expresses) bacteriophage proteins required for assembly of a bacteriophage particle, wherein the plasmid is not packaged (encapsidated) in the bacteriophage particle.

Antimicrobial Peptides and Antibacterial Toxin Proteins

Engineered phagemids of the present disclosure, in some embodiments, comprise a (at least one) synthetic genetic circuit that comprises gene sequences encoding at least one non-lytic antimicrobial peptides (AMPs) and/or antibacterial toxin proteins.

Antimicrobial peptides are potent, broad spectrum antibiotics that can be divided into subgroups based on their amino acid composition and structure. Antimicrobial peptides generally, but not always, have between 12 and 50 amino acids. These peptides typically include two or more positively charged residues provided by arginine, lysine or, in acidic environments, histidine, and a large proportion (generally >50%) of hydrophobic residues. The secondary structures of AMPs are typically $\alpha$-helical, $\beta$-stranded due to the presence of two or more disulfide bonds, $\beta$-hairpin or looped due to the presence of a single disulfide bond and/or cyclization of the peptide chain, or extended. Many of these peptides are unstructured in free solution, and fold into their final configuration upon partitioning into biological membranes. In some instances, AMPs contain hydrophilic amino acid residues aligned along one side and hydrophobic amino acid residues aligned along the opposite side of a helical molecule. This amphipathicity of the antimicrobial peptides allows them to partition into the membrane lipid bilayer. The ability to associate with membranes is a feature of many antimicrobial peptides, although membrane permeabilization is not necessary.

Examples of AMPs for use as provided herein include, without limitation, anionic peptides (rich in glutamic and aspartic acid), linear cationic $\alpha$-helical peptides (lack in cysteine), cationic peptide enriched for specific amino acids (rich in proline, arginine, phenylalanine, glycine, tryptophan) and anionic and cationic peptides that contain cysteine and form disulfide bonds (contain 1-3 disulfide bond(s)). Non-limiting examples of anionic peptides include maximin H5 from amphibians, dermcidin from humans. Non-limiting examples of linear cationic $\alpha$-helical peptides include cecropins, andropin, moricin, ceratotoxin and melittin from insects, magainin, dermaseptin, bombinin, brevinin-1, esculentins and buforin II from amphibians, CAP18 from rabbits, and LL37 from humans. Non-limiting examples of cationic peptides enriched for specific amino acids include abaecin, apidaecins from honeybees, prophenin from pigs, indolicidin from cattle. Non-limiting examples of anionic and cationic peptides that contain cysteine and form disulfide bonds include brevinins (1 bond), protegrin from pig (2 bonds), tachyplesins from horseshoe crabs (2 bonds), defensins from humans (3 bonds), and drosomycin in fruit flies (more than 3 bonds). Antimicrobial peptides are produced by all known species, including peptides from bacteria, from fungi, from hydra, insects (e.g., mastoparan, poneratoxin, cecropin, moricin, melittin and others), frogs (e.g., magainin, dermaseptin and others), and mammals (e.g., cathelicidins, defensins and protegrins).

In some embodiments, AMPs are non-lytic (do not cause cell lysis). Examples of non-lytic AMPs include, without limitation, cecropin PR-39, apidaecin Ia, buforin II, dermaseptin and pleurocidin.

Antibacterial toxin proteins encompassed by the present disclosure include, without limitation, CcdB, YeeV, YeeV truncated at the C terminus by 52 residues (YeeV'), ParE, Colicin (ColN) (including nuclease colicins (e.g., E3, D4, E6 (cleave rRNA), E5 and D (cleave tRNA), E2, E7, E8, E9 (cleave DNA) and pore-forming colicins (e.g., A, B, E1, Ia and Ib), Viriditoxin, RelE (and RelE-like proteins), YoeB, MqsR, YafQ and YgjN. Other antibacterial toxin proteins may be used in accordance with the present disclosure.

In some embodiments, the gene sequences encoding at least one non-lytic AMPs, at least one toxin protein, or at least one non-lytic AMP and at least one toxin protein comprises two (or three or four) tandem copies of the gene sequence.

Synthetic Gene Circuits

Engineered phagemids of the presents disclosure comprise at least one synthetic genetic circuit. An "engineered phagemid" is a phagemid (a filamentous phage-derived vector containing the replication origin of a plasmid and the packaging signal of a bacteriophage) that does not occur in nature. A "genetic circuit" is a collection of genetic elements (e.g., promoters, enhancers, terminators, and nucleic acids encoding proteins, such as AMPs) that interact with each other and with other substances or molecules in a cell to regulate gene expression.

An "engineered nucleic acid" is a nucleic acid (e.g., at least two nucleotides covalently linked together, and in some instances, containing phosphodiester bonds, referred to as a phosphodiester "backbone") that does not occur in nature. Engineered nucleic acids include recombinant nucleic acids and synthetic nucleic acids. A "recombinant nucleic acid" is a molecule that is constructed by joining nucleic acids (e.g., isolated nucleic acids, synthetic nucleic acids or a combination thereof) and, in some embodiments, can replicate in a living cell. A "synthetic nucleic acid" is a molecule that is amplified, chemically synthesized, or synthesized by other means. A synthetic nucleic acid includes those that are chemically modified, or otherwise modified, but can base pair with (also referred to as "binding to," e.g., transiently or stably) naturally-occurring nucleic acid molecules. Recombinant and synthetic nucleic acids also include those molecules that result from the replication of either of the foregoing.

While an engineered nucleic acid, as a whole, is not naturally-occurring, it may include wild-type nucleotide sequences. In some embodiments, an engineered nucleic acid comprises nucleotide sequences obtained from different organisms (e.g., obtained from different species). For example, in some embodiments, an engineered nucleic acid includes a murine nucleotide sequence, a bacterial nucleotide sequence, a human nucleotide sequence, a viral nucleotide sequence, or a combination of any two or more of the foregoing sequences.

In some embodiments, an engineered nucleic acid of the present disclosure may comprise a backbone other than a phosphodiester backbone. For example, an engineered nucleic acid, in some embodiments, may comprise phosphoramide, phosphorothioate, phosphorodithioate, O-methylphophoroamidite linkages, peptide nucleic acids or a combination of any two or more of the foregoing linkages. An engineered nucleic acid may be single-stranded (ss) or double-stranded (ds), as specified, or an engineered nucleic acid may contain portions of both single-stranded and double-stranded sequence. In some embodiments, an engineered nucleic acid contains portions of triple-stranded sequence. An engineered nucleic acid may comprise DNA (e.g., genomic DNA, cDNA or a combination of genomic DNA and cDNA), RNA or a hybrid molecule, for example, where the nucleic acid contains any combination of deoxyribonucleotides and ribonucleotides (e.g., artificial or natural), and any combination of two or more bases, including uracil, adenine, thymine, cytosine, guanine, inosine, xanthine, hypoxanthine, isocytosine and isoguanine.

Engineered nucleic acids of the present disclosure may be produced using standard molecular biology methods (see, e.g., *Green and Sambrook, Molecular Cloning*, A Laboratory Manual, 2012, Cold Spring Harbor Press). In some embodiments, nucleic acids are produced using GIBSON ASSEMBLY® Cloning (see, e.g., Gibson, D. G. et al. *Nature Methods,* 343-345, 2009; and Gibson, D. G. et al. *Nature Methods,* 901-903, 2010, each of which is incorporated by reference herein). GIBSON ASSEMBLY® typically uses three enzymatic activities in a single-tube reaction: 5' exonuclease, the 3' extension activity of a DNA polymerase and DNA ligase activity. The 5' exonuclease activity chews back the 5' end sequences and exposes the complementary sequence for annealing. The polymerase activity then fills in the gaps on the annealed regions. A DNA ligase then seals the nick and covalently links the DNA fragments together. The overlapping sequence of adjoining fragments is much longer than those used in Golden Gate Assembly, and therefore results in a higher percentage of correct assemblies. Other methods of producing engineered nucleic acids are known in the art and may be used in accordance with the present disclosure.

Expression of nucleic acids, including gene sequences, is typically driven by a promoter operably linked to the nucleic acid. A "promoter" refers to a control region of a nucleic acid at which initiation and rate of transcription of the remainder of a nucleic acid sequence are controlled. A promoter drives transcription or of the nucleic acid sequence that it regulates, thus, it is typically located at or near the transcriptional start site of a gene. A promoter, in some embodiments, is 100 to 1000 nucleotides in length. A promoter may also contain sub-regions at which regulatory proteins and other molecules may bind, such as RNA polymerase and other transcription factors. Promoters may be constitutive (e.g., CAG promoter, cytomegalovirus (CMV) promoter), inducible (also referred to as activatable), repressible, tissue-specific, developmental stage-specific or any combination of two or more of the foregoing.

A promoter is considered to be "operably linked" when it is in a correct functional location and orientation relative to a sequence of nucleic acid that it regulates (e.g., to control ("drive") transcriptional initiation and/or expression of that sequence).

A promoter, in some embodiments, is naturally associated with a nucleic acid and may be obtained by isolating the 5' non-coding sequence(s) located upstream of the coding region of the given nucleic acid. Such a promoter is referred to as an "endogenous" promoter.

A promoter, in some embodiments, is not naturally associated with a nucleic acid. Such a promoter is referred to as a "heterologous" promoter and includes, for example, promoters that regulate other nucleic acids and promoters obtained from other cells. A heterologous promoter may be synthetic or recombinant. Synthetic heterologous promoters, in some embodiments, contain various elements obtained from known transcriptional regulatory regions. Synthetic heterologous promoters, in some embodiments, contain mutations that alter expression through methods of genetic engineering that are known in the art. Recombinant heterologous promoters, in some embodiments, are produced by recombinant cloning, nucleic acid amplification (e.g., polymerase chain reaction (PCR)), or a combination of recombinant cloning and nucleic acid amplification (see U.S. Pat. Nos. 4,683,202 and 5,928,906).

A promoter, in some embodiments, is an inducible promoter. An "inducible promoter" regulates (e.g., activates or inactivates) transcriptional activity of a nucleic acid to which it is operably linked when the promoter is influenced by or contacted by a corresponding regulatory protein.

Examples of inducible promoters include, without limitation, chemically- or biochemically-regulated and physically-regulated promoters, such as alcohol-regulated promoters, tetracycline-regulated promoters (e.g., anhydrotetracycline (aTc)-responsive promoters and other tetracycline-responsive promoter systems, which include a tetracycline repressor protein (tetR), a tetracycline operator sequence (tetO) and a tetracycline transactivator fusion protein (tTA)), steroid-regulated promoters (e.g., promoters based on the rat glucocorticoid receptor, human estrogen receptor, moth ecdysone receptors, and promoters from the steroid/retinoid/thyroid receptor superfamily), metal-regulated promoters (e.g., promoters derived from metallothionein (proteins that bind and sequester metal ions) genes from yeast, mouse and human), pathogenesis-regulated promoters (e.g., induced by salicylic acid, ethylene or benzothiadiazole (BTH)), temperature/heat-inducible promoters (e.g., heat shock promoters), and light-regulated promoters (e.g., light responsive promoters from plant cells).

In some embodiments, inducible promoters of the present disclosure function in prokaryotic cells (e.g., bacterial cells). Examples of inducible promoters for use prokaryotic cells include, without limitation, bacteriophage promoters (e.g. Pls1con, T3, T7, SP6, PL) and bacterial promoters (e.g., Pbad, PmgrB, Ptrc2, Plac/ara, Ptac, Pm), or hybrids thereof (e.g. PLlacO, PLtetO). Examples of bacterial promoters for use in accordance with the present disclosure include, without limitation, positively regulated *E. coli* promoters such as positively regulated σ70 promoters (e.g., inducible pBad/araC promoter, Lux cassette right promoter, modified lamdba Prm promote, plac Or2-62 (positive), pBad/AraC with extra REN sites, pBad, P(Las) TetO, P(Las) CIO, P(Rh1), Pu, FecA, pRE, cadC, hns, pLas, pLux), σS promoters (e.g., Pdps), σ32 promoters (e.g., heat shock) and σ54 promoters (e.g., glnAp2); negatively regulated *E. coli* promoters such as negatively regulated σ70 promoters (e.g., Promoter (PRM+), modified lamdba Prm promoter, TetR-TetR-4C P(Las) TetO, P(Las) CIO, P(Lac) IQ, RecA_Dlex-O_DLacO1, dapAp, FecA, Pspac-hy, pcI, plux-cI, plux-lac, CinR, CinL, glucose controlled, modified Pr, modified Prm+, FecA, Pcya, rec A (SOS), Rec A (SOS), EmrR_regulated, BetI_regulated, pLac_lux, pTet_Lac, pLac/Mnt, pTet/Mnt, LsrA/cI, pLux/cI, LacI, LacIQ, pLacIQ1, pLas/cI, pLas/Lux, pLux/Las, pRecA with LexA binding site, reverse BBa_R0011, pLacI/ara-1, pLacIq, rrnB P1, cadC, hns, PfhuA, pBad/araC, nhaA, OmpF, RcnR), σS promoters (e.g., Lutz-Bujard LacO with alternative sigma factor σ38), σ32 promoters (e.g., Lutz-Bujard LacO with alternative sigma factor σ32), and σ54 promoters (e.g., glnAp2); negatively regulated *B. subtilis* promoters such as repressible *B. subtilis* σA promoters (e.g., Gram-positive IPTG-inducible, Xyl, hyper-spank) and σB promoters. Other inducible microbial promoters may be used in accordance with the present disclosure.

In some embodiments, at least one of the gene sequences encoding at least one non-lytic AMPs, at least one toxin protein, or at least one non-lytic AMP and at least one toxin protein is/are operably linked to a tetR-repressed $P_{LtetO}$ promoter.

In some embodiments, the ribosome binding site (RBS) for each antibacterial gene is selected independently. A "ribosomal binding site (RBS)" is a sequence on mRNA that is bound by the ribosome when initiating protein translation. In prokaryotes it is a region referred to as the Shine-Dalgarno sequence, 6-7 nucleotides upstream of a start codon. The sequence is complementary to the 3' end of the rRNA. The ribosome searches for this site and binds to it through base-pairing of nucleotides. Once the ribosome has bound, it recruits initiation factors and begins the translation process.

Bacterial Cells

Some embodiments provide bacterial cells comprising a phagemid system of the present disclosure. Bacteria are small (typical linear dimensions of around 1 micron), non-compartmentalized, with circular DNA and ribosomes of 70S. As used herein, the term "bacteria" encompasses all variants of bacteria, including endogenous bacteria. "Endogenous" bacteria naturally reside in a closed system (e.g., bacterial flora) and are typically non-pathogenic. The present disclosure encompasses non-pathogenic and/or pathogenic bacteria. Bacterial cells may be *Eubacteria* cells. *Eubacteria* can be further subdivided into Gram-positive and Gram-negative *Eubacteria*, which depend on a difference in cell wall structure. Also included herein are those classified based on gross morphology alone (e.g., cocci, bacilli). In some embodiments, the bacterial cells are Gram-negative cells, and in some embodiments, the bacterial cells are Gram-positive cells. Examples of bacterial cells include, without limitation, *Yersinia* spp., *Escherichia* spp., *Klebsiella* spp., *Bordetella* spp., *Neisseria* spp., *Aeromonas* spp., *Franciesella* spp., *Corynebacterium* spp., *Citrobacter* spp., *Chlamydia* spp., *Hemophilus* spp., *Brucella* spp., *Mycobacterium* spp., *Legionella* spp., *Rhodococcus* spp., *Pseudomonas* spp., *Helicobacter* spp., *Salmonella* spp., *Vibrio* spp., *Bacillus* spp., *Erysipelothrix* spp., *Salmonella* spp., *Streptomyces* spp., *Bacteroides* spp., *Prevotella* spp., *Clostridium* spp., *Bifidobacterium* spp., or *Lactobacillus* spp. In some embodiments, the bacterial cells are *Bacteroides thetaiotaomicron, Bacteroides fragilis, Bacteroides distasonis, Bacteroides vulgatus, Clostridium leptum, Clostridium coccoides, Staphylococcus aureus, Bacillus subtilis, Clostridium butyricum, Brevibacterium lactofermentum, Streptococcus agalactiae, Lactococcus lactis, Leuconostoc lactis, Actinobacillus actinobycetemcomitans, cyanobacteria, Escherichia coli, Helicobacter pylori, Selnomonas ruminatium, Shigella sonnei, Zymomonas mobilis, Mycoplasma mycoides, Treponema denticola, Bacillus thuringiensis, Staphylococcus lugdunensis, Leuconostoc oenos, Corynebacterium xerosis, Lactobacillus plantarum, Lactobacillus rhamnosus, Lactobacillus casei, Lactobacillus acidophilus, Streptococcus Enterococcus faecalis, Bacillus coagulans, Bacillus ceretus, Bacillus popillae, Synechocystis* strain PCC6803, *Bacillus liquefaciens, Pyrococcus abyssiSele-* nomonas nominantium, Lactobacillus hilgardii, Streptococcus ferus, Lactobacillus pentosus, Bacteroides fragilis, Staphylococcus epidermidis, Zymomonas mobilis, Streptomyces phaechromogenes, or Streptomyces ghanaenis. In some embodiments, the bacterial cells are of the E. coli strains BL21, DH5α, DH10B, BW25113, Nissle 1917 and/or MG1655 and/or derivatives of any of the foregoing strains (e.g., a modified strain with, for example, a mutation, insertion and/or plasmid).

In some embodiments, the bacterial cells are of a phyla selected from Actinobacteria, Aquificae, Armatimonadetes, Bacteroidetes, Caldiserica, Chlamydiae, Chloroflexi, Chrysiogenetes, Cyanobacteria, Deferribacteres, Deinococcus-*Thermus*, Dictyoglomi, Elusimicrobia, Fibrobacteres, Firmicutes (e.g., *Bacillus, Listeria, Staphylococcus*), Fusobacteria, Gemmatimonadetes, Nitrospirae, Planctomycetes, Proteobacteria (e.g., *Acidobacillus, Aeromonas, Burkholderia, Neisseria, Shewanella, Citrobacter, Enterobacter, Erwinia, Escherichia, Klebsiella, Kluyvera, Morganella, Salmonella, Shigella, Yersinia, Coxiella, Rickettsia, Legionella, Avibacterium, Haemophilus, Pasteurella, Acinetobacter, Moraxella, Pseudomonas, Vibrio, Xanthomonas*), Spirochaetes, Synergistets, Tenericutes (e.g., *Mycoplasma, Spiroplasma, Ureaplasma*), Thermodesulfobacteria and Thermotogae.

Methods of Treatment

Also provided herein are methods of treating a bacterial infection, such as a Actinobacteria, Aquificae, Armatimonadetes, Bacteroidetes, Caldiserica, Chlamydiae, Chloroflexi, Chrysiogenetes, Cyanobacteria, Deferribacteres, Deinococcus-*Thermus*, Dictyoglomi, Elusimicrobia, Fibrobacteres, Firmicutes (e.g., *Bacillus, Listeria, Staphylococcus*), Fusobacteria, Gemmatimonadetes, Nitrospirae, Planctomycetes, Proteobacteria (e.g., *Acidobacillus, Aeromonas, Burkholderia, Neisseria, Shewanella, Citrobacter, Enterobacter, Erwinia, Escherichia, Klebsiella, Kluyvera, Morganella, Salmonella, Shigella, Yersinia, Coxiella, Rickettsia, Legionella, Avibacterium, Haemophilus, Pasteurella, Acinetobacter, Moraxella, Pseudomonas, Vibrio, Xanthomonas*), Spirochaetes, Synergistets, Tenericutes (e.g., *Mycoplasma, Spiroplasma, Ureaplasma*), Thermodesulfobacteria or *Thermotoga* infection.

In some embodiments, the methods comprise administering (delivering) to a subject in need of treatment of a bacterial infection an effective amount of an engineered phagemid as provided herein.

In some embodiments, the methods comprise administering (delivering) to a subject in need of treatment of a bacterial infection an effective amount of phagemid particle as provided herein.

In some embodiments, the methods comprise administering (delivering) to a subject in need of treatment of a bacterial infection an effective amount of a composition comprising an engineered phagemid or phagemid particle as provided herein.

A subject may be a mammalian subject, such as a human subject.

In some embodiments, an "effective amount" is an amount effective to produce non-lytic bacterial cell death in a subject.

Provided herein, in some embodiments, is a synthetic biology platform for producing non-lytic, bacterial cellular death without reliance upon traditional antibiotics. By designing and applying phagemid constructs containing selected AMPs, alone or in combination with bacterial toxins, an approach was developed that achieved over a 5.0 log reduction in bacterial cell viability in vitro and resulted in over 80% survival in a virulent mouse model of peritonitis. While the approach presented here relies on M13 bacteriophage for phagemid production, similar systems can be produced using alternative bacteriophage systems to expand the repertoire of targetable bacteria. The modular nature of this system allows for the replacement and addition of individual components or whole networks within the engineered phagemid for the targeting of specific bacteria. When a packaging signal becomes characterized for a desired bacteriophage, it can be swapped with the F1 origin of replication in the synthetic antibacterial phagemid plasmid and cloned into a production strain that expresses the proper phage proteins. This enables production of both targeted and broad-spectrum antibacterial treatments, depending upon bacteriophage selection. While some toxins tested herein had little effect on the target *E. coli* strain, the selected toxins have a broad-range activity across many bacterial species. Additionally, since the choices for antibacterial peptides are broad spectrum, this system provides a therapeutic that can be readily modified to suit its target and will therefore function in many target bacteria. Due to the stable nature of phagemids and decreased likelihood of resistance formation through superinfection, the system of the present disclosure provides a marked advantage for targeting bacterial infections over current bacteriophage techniques.

With the benefits and importance of healthy bacterial microbiomes as well as the rapid rise in antibiotic resistance, targeted therapies such as those provided herein, which do not rely on classical antibiotics, could provide an invaluable tool for treating bacterial infections and reducing the prevalence of antibiotic-resistant bacterial strains without producing significant collateral damage in the commensal bacterial population.

The following numbered paragraphs are also encompassed by the present disclosure.

1. An engineered phagemid that comprises a (at least one) synthetic genetic circuit, wherein the synthetic genetic circuit comprises gene sequences encoding a (at least one) non-lytic antimicrobial peptides (AMPs) and/or antibacterial toxin proteins, an origin of replication, and a bacteriophage-packaging signal, wherein the engineered phagemid does not comprise some or all gene sequences encoding bacteriophage proteins required for assembly of a bacteriophage particle.

2. The engineered phagemid of paragraph 1, wherein the phagemid does not comprise any gene sequences encoding bacteriophage proteins required for assembly of a bacteriophage particle.

3. The engineered phagemid of paragraph 1 or 2, further comprising a multiple cloning site (MCS).

4. The engineered phagemid of any one of paragraphs 1-3, wherein the phagemid is a high-copy-number phagemid.

5. The engineered phagemid of any one of paragraphs 1-4, wherein the origin of replication is an F1 origin of replication.

6. The engineered phagemid of any one of paragraphs 1-5, wherein the engineered phagemid is an M13-derived phagemid.

7. The engineered phagemid of any one of paragraphs 1-6, wherein the gene sequences encoding a (at least one) non-lytic AMP, a (at least one)toxin protein, or a (at least one) non-lytic AMP and a (at least one) toxin protein comprises two tandem copies of the gene sequence.

8. The engineered phagemid of any one of paragraphs 1-7, wherein at least one of the gene sequences encoding a (at least one) non-lytic AMPs, a (at least one)toxin protein, or a (at least one)non-lytic AMP and a (at least one)toxin protein is/are operably linked to a tetR-repressed $P_{LtetO}$ promoter.

9. The engineered phagemid of any one of paragraphs 1-8, wherein the ribosome binding site (RBS) for each antibacterial gene is selected independently.

10. The engineered phagemid of any one of paragraphs 1-9, wherein the AMPs are selected from the group consisting of cecropin PR-39, apidaecin Ia, buforin II, dermaseptin and pleurocidin.

11. The engineered phagemid of any one of paragraphs 1-10, wherein the AMPs are selected from the group consisting of cecropin PR-39 and apidaecin Ia.

12. The engineered phagemid of any one of paragraphs 1-11, wherein the synthetic genetic circuit comprises gene sequences encoding cecropin PR-39 and apidaecin Ia.

13. The engineered phagemid of any one of paragraphs 1-12, wherein the synthetic genetic circuit comprises two copies of gene sequences encoding cecropin PR-39 and two copies of gene sequences encoding apidaecin Ia.

14. The engineered phagemid of paragraph 13, wherein the two copies of gene sequences encoding cecropin PR-39 and the two copies of gene sequences encoding apidaecin Ia are tandem copies of the gene sequences and are operably linked to a $P_{LtetO}$ promoter.

15. The engineered phagemid of any one of paragraphs 1-14, wherein the antibacterial toxin proteins are selected from the group consisting of CcdB, YeeV, YeeV truncated at the C terminus by 52 residues (YeeV') and ParE.

16. The engineered phagemid of any one of paragraphs 1-15, wherein the antibacterial toxin protein is CcdB, and wherein the synthetic genetic circuit comprises two tandem copies of gene sequences encoding CcdB.

17. A phagemid particle comprising the engineered phagemid of any one of paragraphs 1-16.

18. A composition comprising the engineered phagemid of any one of paragraphs 1-16.

19. A composition comprising the phagemid particle of paragraph 17.

20. A method of treating a bacterial infection, comprising administering to a subject in need of treatment of a bacterial infection an effective amount of the engineered phagemid of any one of paragraphs 1-16.

21. A method of treating a bacterial infection, comprising administering to a subject in need of treatment of a bacterial infection an effective amount of the phagemid particle of paragraph 17.

22. A method of treating a bacterial infection, comprising administering to a subject in need of treatment of a bacterial infection an effective amount of the composition of paragraph 18.

23. A method of treating a bacterial infection, comprising administering to a subject in need of treatment of a bacterial infection an effective amount of the composition of paragraph 19.

24. A phagemid system comprising the engineered phagemid of any one of paragraphs 1-16, and a plasmid comprising a phagemid helper system that expresses bacteriophage proteins required for assembly of a bacteriophage particle, wherein the plasmid is not packaged in the bacteriophage particle.

25. A bacterial cell comprising the phagemid system of paragraph 24.

26. A method, comprising transforming a bacterial cell with the phagemid system of claim 24.

27. The method of paragraph 26 further comprising isolating phagemid particles secreted by the bacterial cell.

28. The method of paragraph 27 further comprising delivering the isolated phagemid particles to a target bacterial cell.

EXAMPLES

Example 1

Figure 2A:
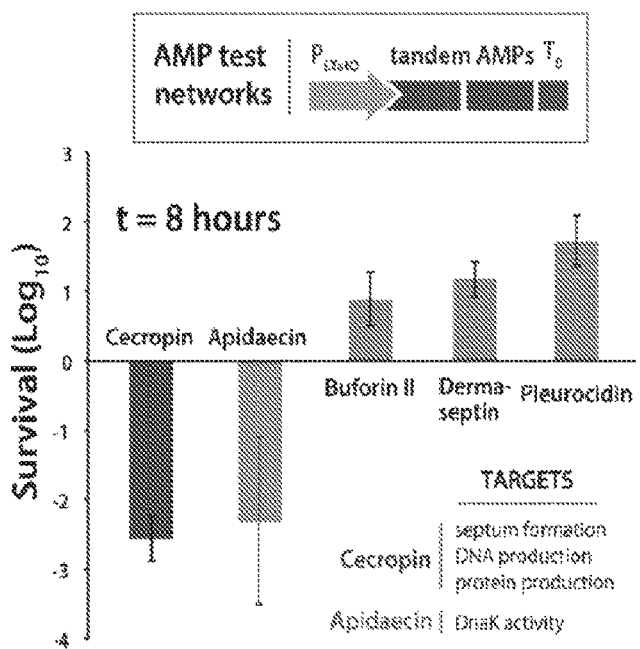
FIGS. 2A-2B show an example of testing antibacterial peptide candidates in test and phagemid networks. (A) Five antibacterial networks, expressing cecropin, apidaecin, buforin II, dermaseptin, or pleurocidin genes, were cloned into the testing strain, mgpro, and tested for their ability to cause bacterial cell death following induction with 100 ng/mL anhydrotetracycline (aTc), which relieves the inhibition of the $P_{LtetO}$ promoter by tetR. (B) Antibacterial networks expressing either cecropin or apidaecin networks were introduced into phagemid and bacteriophage plasmids, and the resulting particles were tested against EMG2 E. coli for their ability to cause non-lytic bacterial death.

In order to initially screen AMPs that cause non-lytic bacterial cell death, a test network expressing two tandem copies of the antibacterial gene of interest under regulation of the tetR-repressed $P_{LtetO}$ promoter was developed. This design allows for activation of antibacterial networks in target wildtype (WT) strains, but represses these networks in tetR (Tet repressor protein) expressing test and production strains. Synthetic design of the ribosome binding site (RBS) (Salis, H. M. et al. *Nature biotechnology* 2009, 27 (10), 946-950) for each antibacterial gene allowed for the independent tuning of expression levels. Five AMPs—cecropin PR-39 (Boman, H. G. et al. *Infection and Immunity* 1993, 61 (7), 2978-2984), apidaecin Ia (Li, W. F. et al. *Peptides* 2006, 27 (9), 2350-2359), buforin II (Park, C. B. et al. *PNAS* 2000, 97 (15), 8245-8250), dermaseptin (Jouenne, T. et al. *Journal of Antimicrobial Chemotherapy* 1998, 42 (1), 87-90), and pleurocidin (Cole, A. M. et al. *Journal of Biological Chemistry* 1997, 272 (18), 12008-12013)—were selected for their reported ability to rapidly disrupt intracellular processes and induce non-lytic bacterial death (Brogden, K. A. *Nature Reviews Microbiology* 2005, 3 (3), 238-250) (Table 1). Together with their $P_{LtetO}$ promoter, synthetic RBS, and terminator, these AMP genes were transformed into the test strain, mgpro, and their efficacy for bacterial death was measured upon anhydrotetracycline (aTc) induced expression (FIG. 2A). Cecropin PR-39 (cecropin) and apidaecin Ia (apidaecin) were effective at inducing bacterial cell death; cecropin inhibits septum formation as well as DNA and protein production, while apidaecin inhibits the enzyme DnaK and binds to bacterial lipopolysaccharide. The remaining AMPs tested did not induce bacterial cell death, possibly due to post-translational modifications or microenvironmental differences with previous studies that our growth conditions did not replicate. Based on these results, cecropin and apidaecin were used for subsequent experiments.

TABLE 1

List of AMPs

| Antimicrobial Peptide | Organism | Size (AA) | Mechanism of Action |
| --- | --- | --- | --- |
| Cecropin PR-39 | Pig | 39 | Inhibits Septum Formation, DNA Production, and Protein Production |
| Apidaecin Ia | Honeybee | 18 | Inhibits Enzyme DnaK and Binds to Bacterial LPS |
| Buforin II | Frog | 21 | Binds Nonspecifically to DNA and RNA |
| Dermaseptin | Frog | 32 | Inhibits DNA Production and Protein Production |
| Pleurocidin | Flounder | 25 | Inhibits DNA Production and Protein Production |

Figure 2B:
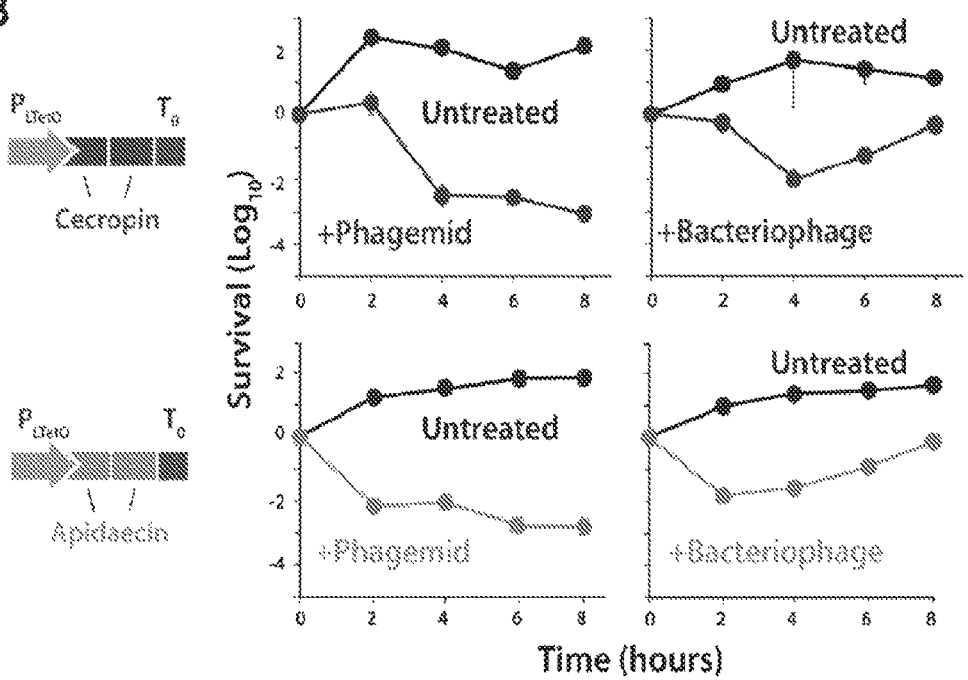

To examine the efficacy of cecropin and apidaecin as antibacterial therapeutics, these AMP expression networks were introduced into the phagemid system. After transforming the system into the phagemid production strain (DH5αpro) carrying the M13 helper plasmid, the purified phagemid particles were collected and screened against the target bacterial strain. Additionally, these antibacterial networks were introduced into the M13 bacteriophage system in order to compare their antibacterial effects. Treatment with phagemid particles harboring networks expressing cecropin or apidaecin reduced bacterial cell viability by 2-3 orders of magnitude (FIG. 2B). This effect persisted for several hours post infection. In contrast, target cells infected with bacteriophage particles carrying the same AMP expression networks failed to produce the same level of bacterial death. Although initial killing was observed, the cell population recovered after approximately four hours of infection, possibly due to inconsistent network expression.

Example 2

Figure 3A:
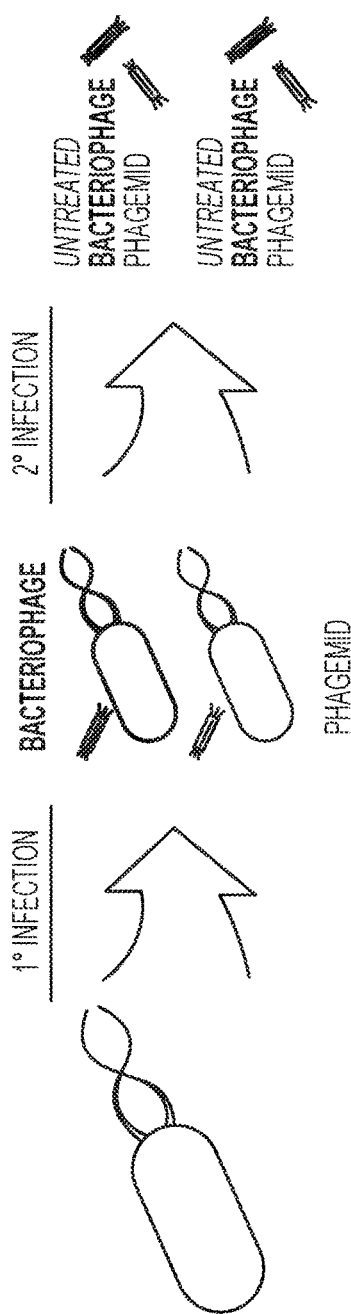
FIGS. 3A-3B show an example of bacteriophage resistance determination for phagemid and bacteriophage therapies. (A) EMG2 E. coli were infected with either bacteriophage or phagemid particles carrying the cecropin antibacterial network. Six hours post infection these cells were monitored for network functionality and diluted overnight. The following day a secondary infection of either bacteriophage or phagemid particles carrying a GFP expression network was administered. These cells, including an uninfected control, were then monitored for GFP expression 6 hours post infection. (B) Infection data from the primary infection with phagemid or bacteriophage particles carrying the cecropin network showed expected bacterial death. Reinfection data from the secondary infection with phagemid or bacteriophage particles carrying a GFP network show bacteriophage resistance formation in samples exposed to bacteriophage but not phagemid particles.
Figure 3B:
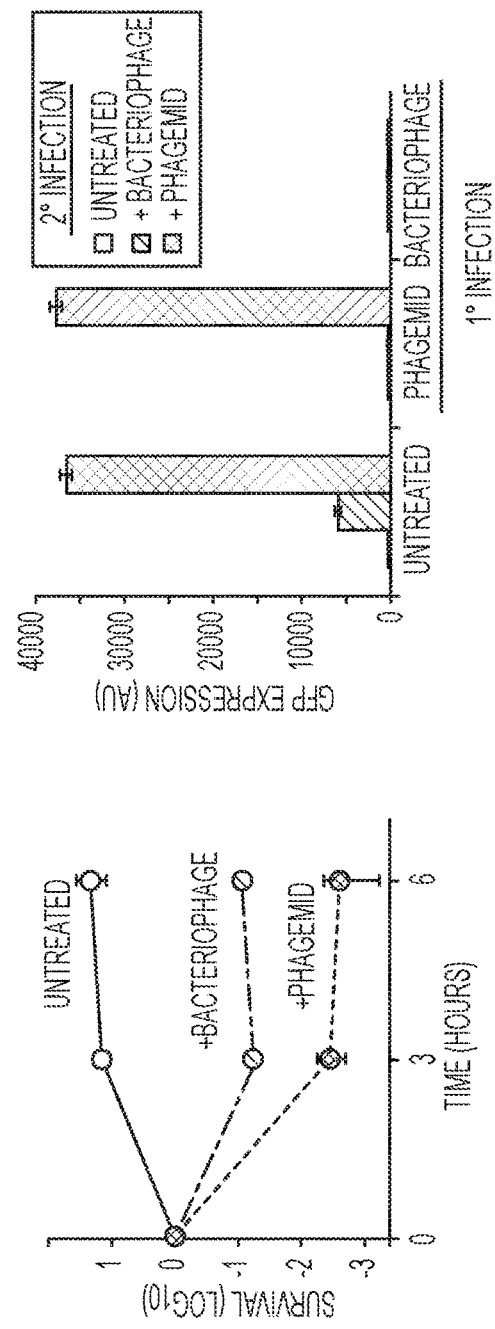

In addition to the ability of the phagemid to sustain bacterial death, it was tested whether this approach induced resistance in target cells at a level comparable to that seen with bacteriophage therapy. Target bacteria were first infected with either phagemid or bacteriophage particles expressing the cecropin AMP network and then subsequently re-infected with phagemid or bacteriophage particles expressing a GFP network (FIG. 3A). Bacteria first infected with bacteriophage particles expressing the cecropin network were found to be resistant to a repeated bacteriophage infection with a GFP-expressing network (FIG. 3B). In contrast, bacteria first infected with phagemid particles carrying the cecropin network maintained their ability to be re-infected with a second round of GFP-expressing phagemid particles. These results highlight both the unreliability of bacteriophage therapy and the increased risk of resistance formation, which are avoided or reduced through the use of phagemids.

Example 3

After distinguishing phagemids as a superior therapy option over bacteriophages, the modular nature of the phagemid system was next studied by examining whether simultaneous targeting could increase phagemid-induced bacterial cell death (cecropin and apidaecin target distinct intracellular processes). Three combination networks expressing both AMPs together were generated (FIG. 4A). Two of these networks (designated $\phi_I$ and $\phi_{II}$) expressed a single copy of each AMP in varying order, while a third network (designated $\phi_{III}$) expressed two copies of each AMP with a $P_{LtetO}$ promoter driving each set. The combined phagemid networks had an enhanced effect upon the target bacteria, with the $\phi_{III}$ network producing a 3.5 log reduction in bacterial cell viability.

To potentially increase the antibacterial efficacy of the phagemid treatment, the effects of three bacterial toxins—Ccdb, YeeV' and ParE—were evaluated by introducing networks expressing the toxin genes into the modular $\phi_{III}$ phagemid platform. The first toxin, CcdB, is a topoisomerase inhibitor that interferes with DNA gyrase and results in the breakdown of bacterial DNA (Couturier, M. et al. *Trends in Microbiology* 1998, 6 (7), 269-275; Callura, J. M. et al. *PNAS* 2010, 107 (36), 15898-15903; and Dwyer, D. J. et al. *Molecular Systems Biology* 2007, 3 (91), 1-15), leading to cell death. YeeV is a toxin that inhibits cellular division by targeting two cytoskeletal proteins, FtsZ and MreB (Tan, Q. et al. *Molecular Microbiology* 2011, 79 (1), 109-118); however, this dual inhibition causes cells to balloon and lyse, which is undesirable for purposes of these experiments. Sole inhibition of FtsZ can be accomplished by expression of a modified version of the YeeV protein truncated at the C terminus by 52 residues (designated YeeV'), which results in filamented cells that do not lyse (Tan, Q. et al. *Molecular Microbiology* 2011, 79 (1), 109-118). The last toxin, ParE, acts by halting the F1* formation from both chromosomal and plasmid DNA replication origins by inhibiting bacterial gyrase, causing filamentation and cell death (Jiang, Y. et al. *Molecular Microbiology* 2002, 44 (4), 971-979). Infection of target cells with phagemid particles carrying the combined AMP-CcdB network resulted in increased bacterial cell death, leading to a 4.0 log reduction in bacterial cell viability within the first two hours (FIG. 4B). The addition of yeeV' resulted in bacterial cell death comparable to that of $\phi_{III}$ alone, while the addition of parE led to reduced killing, possibly due to direct interaction with our phagemid plasmid's ability to replicate.

With these results, a final synthetic network employing the most productive toxin was generated. This construct, designated $\phi_{IV}$, overexpressed ccdB through tandem gene expression in order to maximize its antibacterial effect and was combined with the $\phi_{III}$ AMP network. Purified phagemid particles were then tested against the target bacteria for induced bacterial cell death (FIG. 4C). Expression of $\phi_{IV}$ provided almost an order of magnitude of increased bacterial cell death compared to $\phi_{III}$ alone. This difference was further enhanced by increasing the virion particle dose, resulting in over 5.0 log reduction in bacterial survival after 6 hours of exposure to the $\phi_{IV}$ network (FIG. 4D). Taken altogether, our screen identified that the combined phagemid-based expression of two copies of cecropin PR-39, apidaecin Ia, and ccdB genes resulted in robust killing of target *E. coli* bacteria.

Example 4

Figures 5A, 5B:
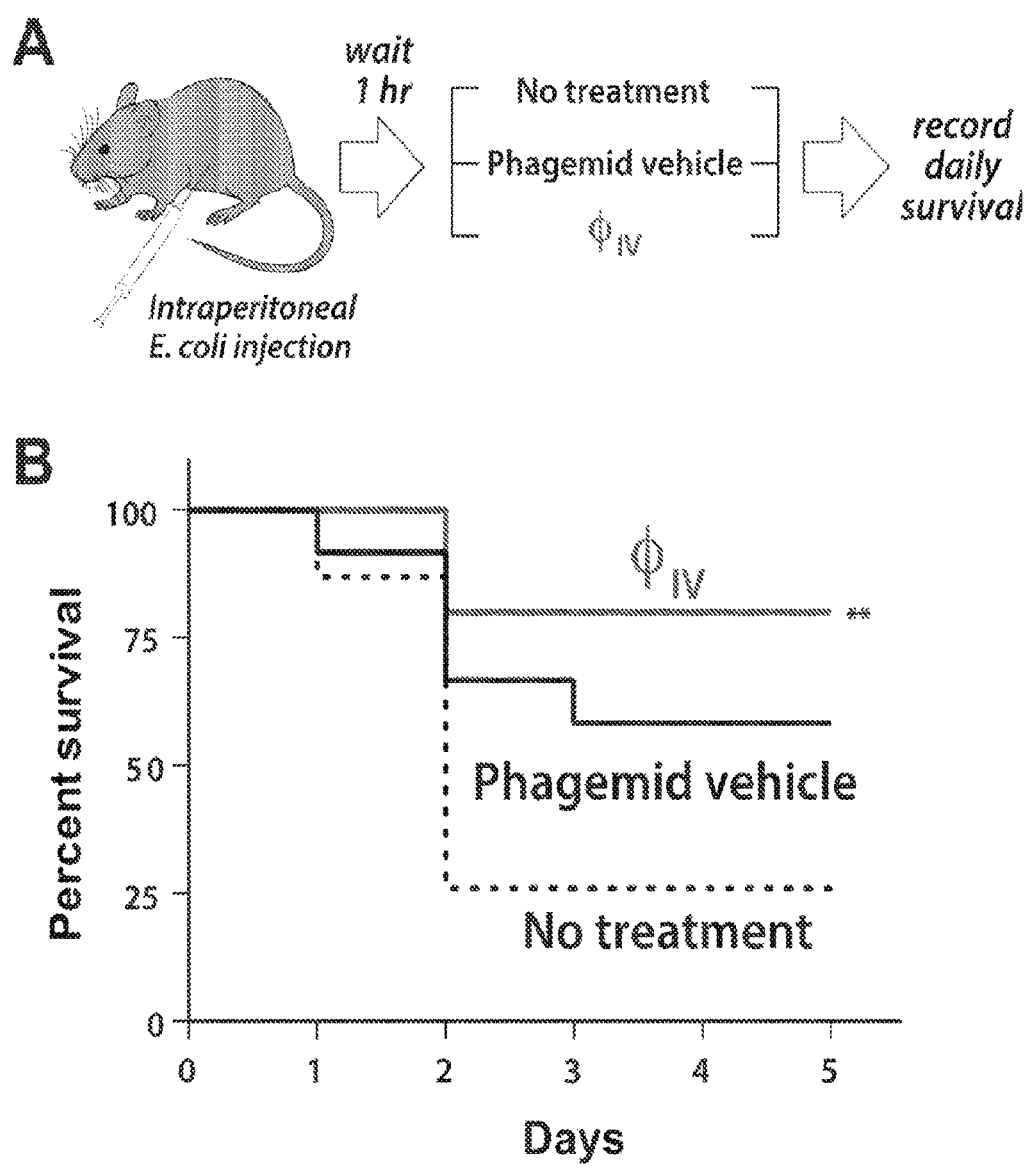
FIGS. 5A-5B show an example of a murine peritonitis infection model with $\phi_{IV}$-expressing phagemid particles. (A) Overview of murine model for bacterial peritoneal infection with EMG2 *E. coli* bacteria and subsequent phagemid treatment. (B) Survival data for murine infection model with phagemid treatments and controls. Mice were divided into three groups: untreated (n=22), vehicle only (n=12), and $\phi_{IV}$ (n=10). Data were obtained from two separate experiments and significance was determined by a Mantel-Cox test.
Figure 7:
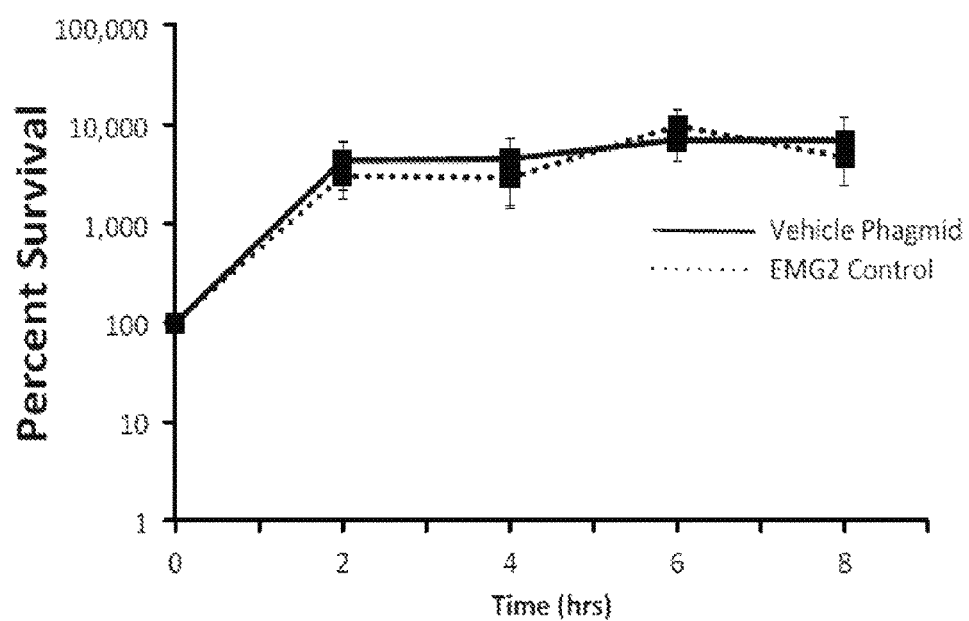
FIG. 7 shows gene expression by bacteriophage- and phagemid-delivered networks. Effects of vehicle phagemid particles expressing no antibacterial genes against EMG2 bacteria.

The in vivo efficacy of this system was tested next by employing a murine model for *E. coli* peritonitis (Domenech, A. et al. *Microbial Drug Resistance* 2004, 10 (4), 346-353). Seven-week-old C57Bl/6 female mice were administered $10^6$ colony forming units (CFUs) of the target bacteria via intraperitoneal (IP) injection. After 1 hour, mice were treated with IP injections of phagemids expressing the $\phi_{IV}$ antibacterial-toxin network (FIG. 5A). Mice were either not treated, injected with phagemid particles that do not express any genes (vehicle), or injected with phagemid particles containing the $\phi_{IV}$ network (FIG. 5B). Mice given the $\phi_{IV}$ phagemid treatment had an average survival rate of 80% over the course of the experiment, compared to 27% survival in the untreated group, an increase that was statistically significant (p=0.003). The vehicle group experienced an improved survival of 58%, which was not statistically significant when compared to the untreated group (p=0.08). This effect was not observed in vitro (FIG. 7), suggesting that the increased survival was due to interactions with the host. A survival advantage provided by phage particles has been previously reported (Duerkop, B. A. et al. *Nat. Immunol.* 2013, 14 (7), σ54-659) and may be associated with type I interferon and other proinflammatory gene induction upon exposure to phage capsid proteins. This proinflammatory effect is beneficial for treatment of bacterial infections, as phagemid particles prime the host immune system against unwanted bacteria. Taken together, our results show that engineered phagemids can effectively target and produce highly effective non-lytic killing of *E. coli* in vitro and in vivo, without the use of antibiotics.

Experimental Details

Strains and Culture Conditions.

Bacterial cultures were grown in a 37° C. shaking incubator with Luria-Bertani (LB) medium (Fisher Scientific).

Bacterial strains used were either MG1655 containing the pro cassette (mgpro, spectinomycin resistant), EMG2, or DH5α cells carrying the pro cassette (DH5αpro). When needed, antibiotics were added to the growth medium at the following final concentrations: kanamycin (Km) 50 μg/ml, ampicillin (Am) 50 μg/ml, and chloramphenicol (Cm) 34 μg/ml.

TSS Transformation Assay.

Overnight cultures of the desired cell type were diluted 1:100 in fresh LB and grown to an optical density (OD600) of approximately 0.5-0.6. These cultures were then split into 1 ml aliquots and spun at 3500 rpm for 10 minutes at 4° C. The supernatant was then aspirated and the pellets were resuspended in ⅒th the original volume of TSS buffer. After approximately 50 ng of ligated or plasmid DNA was added to the cells, the aliquots were incubated on ice for 30 minutes before heat shocking for 30 seconds at 42° C. Next, 300 μl of LB was added and the aliquots were incubated at 37° C. for 1 hrl. Finally 100 μl of competent cells were plated on the appropriate agar plate and incubated overnight at 37° C. To make TSS buffer 5 g PEG 8000, 2.4 ml DMSO, and 1.5 ml of 1M magnesium chloride was added to LB at a final volume of 50 ml. Next, it was filtered through a 0.22 μm filter and stored at −20° C. A working stock was kept at 4° C.

Primer Design.

The PCR primers used for plasmid constriction and modification (Table 2) were designed according to the following algorithm. Each primer began (5') with six bases arbitrarily selected to create primers with similar Tm, calculated using OligoCalc (basic.northwestern.edu/biotools/oligocalc.html). The next six bases (5'-3') comprised the desired restriction enzyme recognition site. The remainder of the primer, the 3' end, consisted of either the 'Forward Primer Homology' or the 'Reverse Primer Homology' sequences, annotated in the component sequence entries. Thus, the final primer design was 5'—six arbitrary bases+six bases for recognition site+fw./rev. primer homology—3'. For genes, a ribosomal binding site (RBS) was added as determined by the RBS calculator designed by the Salis Lab. All RBS were designed to operate at a translation rate of 100,000 arbitrary units. The primers were ordered from Integrated DNA Technologies (IDT).

Antibacterial Peptide Plasmid Construction.

In order to generate the antibacterial peptide plasmids, the breadboard plasmid pKE3_MCS described by Litcofsky et al.8 was used. The PLtet0 promoter and T0 terminator parts were amplified from the library plasmids pKLi008 and pKLi027, respectively, using PCR. Primers added the proper restriction and the parts were cloned into the multiple cloning site (MCS) of the pKE3_MCS plasmid using standard cloning methods to create the general cloning plasmid pRJK034 (kanamycin resistant) (GenBank accession number KT003672). Plasmids were transformed into the desired cell type using the TSS competent cell protocol. Antimicrobial peptides (AMPs) were synthesized by Genewiz and amplified using primers designed to add proper restriction sites and the appropriate RBS. These PCR products were then digested and cloned into the MCS of the general cloning plasmid pRJK034 in order to create the AMP test networks pRJK037 (KT003673), pRJK046 (KT003674), pRJK055 (KT003675), pRJK062 (KT003676), and pRJK070 (KT003677) respectively for cecropin PR-39, apidaecin Ia, buforin II, dermaseptin, and pleurocidin networks.

Test Network Induction Assays.

Overnight cultures of the AMP test networks were diluted 1:100 in fresh LB and grown to an optical density (OD600) of approximately 0.2-0.3. Cultures were then induced as appropriate with 100 ng/ml of aTc. Cultures were then grown for 8 hours post induction, with time points taken every 2 hours to track the cellular growth and determine colony forming units. All conditions were performed in triplicate.

Colony Forming Unit (CFU) Determination.

In order to determine the CFUs, 300 μl of culture was placed into the top well of a 96-well plate (Costar). The culture was serially diluted 1:10 into phosphate-buffered saline (Fisher Scientific) a total of 7 times. Five μl of each dilution was then plated onto a dry LB agar plate and put into a 30° C. static incubator overnight. Colonies were counted in the first dilution that allowed for distinguishable colonies and the CFUs were determined. All conditions were performed in triplicate.

Phagemid Network Construction.

To create the phagemid networks, the F1 origin was first synthesized from Genewiz with XhoI/SspI restriction sites on either end. This was then introduced into the general cloning plasmid pRJK034 to create the phagemid plasmid pPh034. The AMP PCR products of cecropin PR-39 and apidaecin Ia were cloned into this plasmid in order to make the phagemid plasmids pPh037 and pPh046. To make the combined AMP phagemid networks ΦI and ΦII, the second AMP cassette from both pPh037 (GenBank accession number KT003678) and pPh046 (KT003679) were digested out of the plasmid and replaced with the AMP cassette of the other corresponding AMP network. To make the combined AMP phagemid ΦIII, the AMP network from pPh037 was amplified using PCR and subsequently digested and cloned into the slot in the MCS of pPh046 to create the pPh079 plasmid (KT003680).

Phagemid Purification and Characterization.

Phagemid plasmids were transformed into DH5αpro bacteria, which contained the m13cp plasmid (chloramphenicol resistant) using the TSS protocol. This was then plated on LB agar plates containing 50 μg/ml Km and 34 μg/ml Cm. A single colony was then grown up and spun at 4000 rpm for 10 minutes at 4° C. The supernatant was sent through a 0.2 μm filter (Fisher Scientific) and the resulting phagemid particles were stored at 4° C. To quantify the concentration, samples were read on a spectrophotometer for absorbance at 269 and 320 nm. From this, the concentration was calculated using the formula established by G. Smith (abdesignlabs.com/technicalresources/bacteriophage-spectrophotometry/).

Phagemid Network Induction Assays.

Overnight cultures of EMG2 were diluted 1:100 in fresh LB and grown to an optical density of approximately 0.2-0.3. Cultures were treated with approximately $5 \times 10^{11}$ phagemid particles per ml culture. Cultures were then grown for 8 hours post infection with time points taken every 2 hours unless otherwise stated. All conditions were performed in triplicate.

Reinfection Assay.

Overnight cultures of EMG2 were diluted 1:100 in fresh LB and grown to an optical density of approximately 0.2-0.3. Cultures were treated with approximately $5 \times 10^{11}$ bacteriophage or phagemid particles per ml culture. Cultures were then grown for 6 hours and plated for CFU determination. Cultures were then diluted 1:1000 and grown overnight. The following day, overnight cultures were diluted 1:100 in fresh LB and grown to an optical density of approximately 0.2-0.3. Cultures were then treated with approximately 5×10$^{11}$ bacteriophage or phagemid particles per ml culture. Cultures were then grown for 6 hours and read for fluorescence.

Toxin Plasmid Construction.

Effector genes were synthesized from Genewiz to create ccdB, yeeV', and parE DNA sequences. These genes were amplified by PCR and cloned into the pRJK034 general cloning plasmid using the proper restriction enzymes and normal cloning methods. The completed networks were amplified by PCR and cloned into the phagemid plasmid pPh079 in order to create the toxin networks pPh110 (GenBank accession number KT003681), pPh112 (KT003682), pPh113 (KT003683), and pPh115 (KT003684) (expressing the YeeV mutant, ParE, two copies of CcdB, or a single copy of CcdB, respectively).

Murine Peritonitis Model.

Seven-week-old female mice weighing an average of 16.6 grams were injected with ~8.6×10$^5$ CFU/mouse of EMG2 bacteria via intraperitoneal (IP) injection. One hour later, the mice received either 200 µl of phage treatment (approximately 3×10$^{10}$ virons/µl), 200 µl of vehicle (approximately 3×10$^{10}$ virons/µl), or no treatment. These treatments were administered via intraperitoneal injection. The mice were monitored daily for survival for 5 days. Two different experiments were combined to obtain the statistics shown using a Mantel-Cox test (untreated n=22, vehicle only n=12, ΦCcdB phagemid n=10, ΦCcdB/LexA3 phagemid n=12).

Data Analysis and Statistics.

For the CFU determination experiments, the results of biological triplicates were imputed into Excel and the geometric mean and standard deviation were determined. For the murine model, the results of the two experiments were entered into Prism 6.0 software, which computed the Mantel-Cox Test p-value for the survival curves compared to the untreated group.

TABLE 2

List of designed primers

| Plasmid | Part | Name | Sequence | SEQ ID NO: | Site |
|---|---|---|---|---|---|
| pPh034 | P$_{LTetO}$ Promoter | fpRJK035 | GCCCGCAAGCTTTCCCTATCAGTGATAGAGATTGACA | 1 | HindIII |
| | P$_{LTetO}$ Promoter | rpRJK035 | ATTTTTGGTACCGGTCAGTGCGTCCTGCTGATGTGCT | 2 | KpnI |
| | T0 Terminator | fpRJK039 | TATTTAGGATCCCGAGAATTGGCTTGGACTCCTGTTG | 3 | BamHI |
| | T0 Terminator | rpRJK039 | GATTATGAGCTCTGACTACTGCTTGATTCTCACCAA | 4 | SacI |
| | F1 Origin | fpRJK042 | TATTTACTCGAGAGCGCCCTGTAGCGGCGCATT | 5 | XhoI |
| | F1 Origin | rpRJK042 | GGCGCGAATATTTAATTCGCGTTAAATTTTTGTTAAATCAGCTCATTTTTTAACCAATAG | 6 | SspI |
| pPh037 | Cecropin PR-39 | fpRJK037 | AATTTAGGTACCCTATAAGTTACACAACATAAGGAGGAATATAATGCGTCGTCGTCCGCGTCC | 7 | KpnI |
| | Cecropin PR-39 | rpRJK037a | AGAATTCCGCGGTTACGGGAAACGCGGCGGGAAACGC | 8 | SacII |
| | Cecropin PR-39 | fpRJK038 | ATTTATTGTACATTCTATCAAAGTATCATAAGGAGGAGAATAATGCGTCGTCGTCCGCGTCC | 9 | BsrGI |
| | Cecropin PR-39 | rpRJK038a | GAGGTCGGATCCTTACGGGAAACGCGGCGGGAAACGC | 10 | BamHI |
| pPh046 | Apidaecin Ia | fpRJK044 | ATTTATGGTACCCAACAGGGATTCGTTAATTTAAGGAGGTCTCCAAATGGGCAACAACCG | 11 | KpnI |
| | Apidaecin Ia | rpRJK044a | ATTTATCCGCGGTTAAATGCGCGGATGCGGCG | 12 | SacII |
| | Apidaecin Ia | fpRJK045 | ATTGCGTGTACAGAGGTACAACTCAACTAATATAAGGAGGTTCAAATGGGCAACAACCG | 13 | BsrGI |
| | Apidaecin Ia | rpRJK045a | ATCGCGGGATCCTTAAATGCGCGGATGCGGCG | 14 | BamHI |
| pPh054 | Buforin II | fpRJK046 | ATTTTTGGTACCCGACTAACAACTCTATAAGGAGGTCCATAAATGACCCGCAGCAGC | 15 | KpnI |
| | Buforin II | rpRJK046a | ATTGCCCCGCGGTTATTTGCGCAGCAGGCGAT | 16 | SacII |
| | Buforin II | fpRJK047 | ATTTATTGTACAGAGGTACAACTCAACTAATATAAGGAGGTTCAAATGACCCGCAGCAG | 17 | BsrGI |
| | Buforin II | rpRJK047a | GCGCCCGGATCCTTATTTGCGCAGCAGGCGAT | 18 | BamHI |
| pPh062 | Dermaseptin | fpRJK048 | ATTTATGGTACCTAAAAGAGGAGACTCACCCTTAAGGAGGTATAAGATGGCGCTGTGGAA | 19 | KpnI |
| pPh062 | Dermaseptin | rpRJK048a | ATTCCCCCGCGGTTAGCTTTCCGCGCCCACCA | 20 | SacII |

TABLE 2-continued

List of designed primers

| Plasmid | Part | Name | Sequence | SEQ ID NO: | Site |
|---|---|---|---|---|---|
| | Dermaseptin | fpRJK049 | ATTTATTGTACACAAGTACAGAGGAGTAAGGAGGTAAAGTATGGCGCTGTGGAAAAACAT | 21 | BsrGI |
| | Dermaseptin | rpRJK049a | CCTGCGGGATCCTTAGCTTTCCGCGCCCACCA | 22 | BamHI |
| pPh070 | Pleurocidin | fpRJK050 | ATTTATGGTACCAACGGTAAGAGGCATAATTTAAGGAGGTAACACATGGGCTGGGGCAG | 23 | KpnI |
| | Pleurocidin | rpRJK050a | CGCCGCCCGCGGTTACAGATAATGGGTCAGCG | 24 | SacII |
| | Pleurocidin | fpRJK051 | ATTGTTTGTACAGATTTATAAAATCGGAATAGATAAGGAGGTACACATGGGCTGGGGCAG | 25 | BsrGI |
| | Pleurocidin | rpRJK051a | CGCCGCGGATCCTTACAGATAATGGGTCAGCG | 26 | BamHI |
| pPh079 | Cecropin Network | fpRJK052 | AATCATCTGCAGTCCCTATCAGTGATAGAGATTGACATCCCT | 27 | PstI |
| | Cecropin Network | rpRJK052 | GGCCCGGAATTCTGACTACTGCTTGGATTCTCACCAATAAAA | 28 | EcoRI |
| pPh080 | LexA3 | fpRJK053 | TATAATGGTACCCAGGGAGGGAAAGTCAATAAGGACGGATATTATGAAAGCGTTAACGGCCAG | 29 | KpnI |
| | LexA3 | rpRJK053 | CCGGCCGGATCCTTACAGCCAGTCGCCGTTGCGAATA | 30 | BamHI |
| pPh082 | SoxR | fpRJK054 | ATTTATCCGCGGGCCTACTAGAAACTAATAAGGAGACTACCGAGAATGGAAAAGAAATTACCC | 31 | SacII |
| | SoxR | rpRJK054 | ATTTATGGATCCTTAGTTTTGTTCATCTTCCAGCAAGCGTGCGCCGG | 32 | BamHI |
| pPh084 | CedB | fpRJK055 | ATTTATGGTACCTATCCATCATTAACGACCAAATCAAGGAGGACGTATGCAGTTTAAGGTTTACA C | 33 | KpnI |
| | CedB | rpRJK055 | GGCCGCGGATCCTTATATTCCCCAGAACATCAGGTTAATGGCGTTTT | 34 | BamHI |
| pPh086 | CsrA | fpRJK056 | ATTTATGGTACCGCCCCAACGAACAATATTACTAAGGAGGAAAGATATGCTGATTCTGACTCGT | 35 | KpnI |
| | CsrA | rpRJK056 | GGCATTGGATCCTTAGTAACTGGACTGCTGGGATTTTTCAGCCTGGATA | 36 | BamHI |
| Effector Phagemid Networks | Effector Networks | fpRJK059 | ATTGGCCTTAAGTCCCTATCAGTGATAGAGATTGACATCC | 37 | AflIII |
| | Effector Networks | rpRJK059a | ATTTCCCCTAGGTGACTACTGCTTGGATTCTCACCAATAA | 38 | AvrII |
| | Effector Networks | rpRJK059b | ATTTTTGGCGCCTGACTACTGCTTGGATTCTCACCAATAA | 39 | KasI |
| | Effector Networks | rpRJK059c | ATTCAGCAATTGTGACTACTGCTTGGATTCTCACCAATAA | 40 | MfeI |
| pPh110 | YeeV Mutant | fpRJK063 | TATATTGGTACCCAAGAAGATAGAGGAGGTAATATACAAGAGAATGAACACCCTGCCGGATACCCATG | 41 | KpnI |
| | YeeV Mutant | rpRJK063 | GGGCGGCCGCGGTTATTTTTTCCACCAGAAAGTTCACCGCATC | 42 | SacII |
| | YeeV Mutant | fpRJK064 | ATTTATTGTACAAGCCTAACGGAAGTCGACTAGTAAGGAGAACTAAATGAACACCCTGCCGGATA | 43 | BsrGI |
| pPh110 | YeeV Mutant | rpRJK064 | GGGCGGGGATCCTTATTTTTTCCACCAGAAAGTTCACCGCATC | 44 | BamHI |
| pPh112a | ParE | fpRJK066 | ATTTATGGTACCTCACAATCAAATCTAAGGAGTTACAAATGACCGCGTATATTCTGACCGTCG | 45 | KpnI |
| | ParE | rpRJK066 | ATTGATCCGCGGTTAGCCTTTCAGGCGATCCGCCAGG | 46 | SacII |
| | ParE | fpRJK067 | ATTTATTGTACATACACTATATTAACCTAAAAAGGAGCGTAACGAATGACCGCGTATATTCTGAC CGCTG | 47 | BsrGI |

TABLE 2-continued

List of designed primers

| Plasmid | Part | Name | Sequence | SEQ ID NO: | Site |
|---|---|---|---|---|---|
| | ParE | rpRJK067 | GGCGCGGGATCCTTAGCCTTTCAGGCGATCCGCCAGG | 48 | BamHI |
| pPh113 | CcdB | fpRJK065 | AATTATCCGCGGTACCAACCCCCCTATTAGAATAAGGAGTATCACGCATGCAGTTTAAGGTTTAC A | 49 | SacII |
| | CcdB | rpRJK065a | CAGGGGCCGCGGTTATATTCCCCAGAACATCAGGTTAATGGCGTTTT | 50 | SacII |
| | CcdB | rpRJK065b | CCGGGGGGATCCTTATATTCCCCAGAACATCAGGTTAATGGCGTTTT | 51 | BamHI |
| pPh114 | LexA3 Network | fpRJK069 | ATTTATGGCGCCTCCCTATCAGTGATAGAGATTGACATCCCTATCAGTGATAGAG | 52 | KasI |
| | LexA3 Network | rpRJK069 | ATTCAGGATATCTGACTACTGCTTGGATTCTCACCAATAAAAAACGCCCGG | 53 | EcoRV |
| | LexA3 Network | rpRJK069a | ATTCAGCCTAGGTGACTACTGCTTGGATTCTCACCAATAAAAAACGCCCGG | 54 | AvrII |

Sequences

\>pRJK034 [organism = cloning vector] SEQ ID NO: 55
gacgtctgtgcaagtactactgttctgcagtcacttgaattcgatacccagctgggtggagtgcaccaaggagcatgcgaaggaaacg
tttcgcagaagctttccctatcagtgatagagattgacatccctatcagtgatagagatactgagcacatcagcaggacgcactgacc
ggtaccactttgccgcggagtatttgtacatttgaaggatcccgagaattggcttggactcctgttgatagatccagtaatgacctca
gaactccatctggatttgttcagaacgctcggttgccgccgggcgttttttattggtgagaatccaagcagtagtcagagctcggact
gcttaagtcgctccatatgctcgttcccgggactacacaattgtccccggcgccagggttgatatctatcgccctagggaccgtctc
gagagaatcaatattaatccaacgcgtggcatcaaataaaacgaaaggctcagtcgaaagactgggcctttcgttttatctgttgttt
gtcggtgaacgctctcctgagtaggacaaatccgccgccctagacttaggcgttcggctgcggcgagcggtatcagctcactcaaagg
cggtaatacggttatccacagaatcaggggataacgcaggaaaagaacatgtgagcaaaaggccagcaaaaggccaggaaccgtaaaaa
ggccgcgttgctggcgtttttccataggctccgcccccctgacgagcatcacaaaaatcgacgctcaagtcagaggtggcgaaacccg
acaggactataaagataccaggcgtttccccctggaagctccctcgtgcgctctcctgttccgaccctgccgcttaccggatacctgt
ccgcctttctcccttcgggaagcgtggcgctttctcatagctcacgctgtaggtatctcagttcggtgtaggtcgttcgctccaagct
gggctgtgtgcacgaaccccccgttcagcccgaccgctgcgccttatccggtaactatcgtcttgagtccaacccggtaagacacgac
ttatcgccactggcagcagccactggtaacaggattagcagagcgaggtatgtaggcggtgctacagagtcttgaagtggtggccta
actacggctacactagaaggacagtatttggtatctgcgctctgctgaagccagttaccttcggaaaaagagttggtagctcttgatc
cggcaaacaaaccaccgctggtagcggtggtttttttgtttgcaagcagcagattacgcgcagaaaaaaggatctcaagaagatcct
ttgatcttttctacggggtctgacgctcagtggaacgaaaactcacgttaagggattttggtcatgagattatcaaaaaggatcttca
cctagatccttttaaattaaaaatgaagttttaaatcaatctaaagtatatatgagtaaacttggtctgacagttaccaatgcttaat
cagtgaggcacctatctcagcgatctgtctatttcgttcatccatagttgcctgactccccgtcgtgtagataactacgatacgggag
ggcttaccatctggccccagtgctgcaatgataccgcgagacccacgctcaccggctccagatttatcagcaataaaccagccagccg
gaagggccgagcgcagaagtggtcctgcaactttatccgcctccatccagtctattaattgttgccgggaagctagagtaagtagttc
gccagttaatagtttgcgcaacgttgttgccattgctacaggcatcgtggtgtcacgctcgtcgtttggtatggcttcattcagctcc
ggttcccaacgatcaaggcgagttacatgatcccccatgttgtgcaaaaaagcggttagctccttcggtcctccgatcgttgtcagaa
gtaagttggccgcagtgttatcactcatggttatggcagcactgcataattctcttactgtcatgccatccgtaagatgcttttctgt
gactggtgagtactcaaccaagtcattctgagaatagtgtatgcggcgaccgagttgctcttgcccggcgtcaatacgggataatacc
gcgccacatagcagaactttaaaagtgctcatcattggaaaacgttcttcggggcgaaaactctcaaggatcttaccgctgttgagat
ccagttcgatgtaacccactcgtgcacccaactgatcttcagcatcttttactttcaccagcgtttctgggtgagcaaaaacaggaag
gcaaaatgccgcaaaaaagggaataagggcgacacggaaatgttgaatactcatactcttcctttttcaatattattgaagcatttat
cagggttattgtctcatgagcggatacatatttgaatgtatttagaaaaataaacaaataggggttccgcgcacatttccccgaaaag
tgccacctgacgtctaagaaaccattattatcatgacattaacctataaaaataggcgtatcacgaggccctttcgtcttcaagaatt
ctcatgtttgacagcttatcatcgataagctttaatgcggtagtttatcacagttaaattgctaacgcagtcaggcaccgtgtatgaa
atctaacaatgcgctcatcgtcatcctcggcaccgtcaccctggatgctgtaggcataggcttggttatgccggtactgccgggccct
cagaagccaaagctatgatggtttctgtggtggaggaggctacgcgcagggcgtatctgcccacgtcacatccgaaggtatcggcacc
ctcatatgttactgccgtagaagacgtttgatcttgatttctgcgcaacttcagcaatatcacgggtagccaacgctatgtcctgata
gcggtccgccacacccagccggccacagtcgatgaatccagaaaagcggccattttccaccatgatattcggcaagcaggcatcgccg
tgggtcacgacgagatcctcgccgtcgggcatacgcgccttgagcctggcgaacagttcggctggcgcgagcccctgatgctcttcgt
ccagatcatcctgatcgacaagaccggcttccatccgagtacgtgctcgctcgatgcgatgtttcgcttggtggtcgaatgggcaggt
agccggatcaagcgtatgcagccgccgcattgcatcagccatgatggatactttctcggcaggagcaaggtgagatgacaggagatcc
tgccccggcacttcgcccaatagcagccagtcccttcccgcttcagtgacaacgtcgagcacagccgcgcaaggaacgcccgtcgtgg
ccagccacgatagccgcgctgcctcgtcttgcagttcattcagggcaccggacaggtcggtcttgacaaaaagaaccgggcgcccctg
cgctgacagccggaacacggcggcatcagagcagccgattgtctgttgtgcccagtcatagccgaatagcctctccacccaagcgccg
ccagaacctgcgtgcaatccatcttgttcaatcatgcgaaacgatcctcatcctgtctcttgatcagatcttgatccctgcgccatca
gatccttggcggcaagaaagccatccagtttactttgcagggcttcccaaccttaccagagggcgccccaactggcaattcc \>pRJK037 [organism = cloning vector] SEQ ID NO: 56
gacgtctgtgcaagtactactgttctgcagtcacttgaattcgatacccagctgggtggagtgcaccaaggagcatgcgaaggaaacg
tttcgcagaagctttccctatcagtgatagagattgacatccctatcagtgatagagatactgagcacatcagcaggacgcactgacc
ggtaccctataagttacacaacataaggaggaatataatgcgtcgtcgtccgcgtccgcgtacctgccgcgtccgcgtccgccgccgt
ttcttcccgccgcgtctgccgccgcgtatcccgccgggtttccccgccgcgtttcccgccgcgtttcccgtaaggatcccgagaattggcttgg
actcctgttgatagatccagtaatgacctcagaactccatctggatttgttcagaacgctcggttgccgccgggcgttttttattggt
gagaatccaagcagtagtcagagctcggactgcttaagtcgctccatatgctcgttcccgggactacacaattgtccccggcgccag
ggttgatatctatcgccctagggaccgtctcgagagcgccctgtagcgcgcattaagcgcggcgggtgtggtggttacgcgcagcgt
gaccgctacacttgccagcgccctagcgcccgctcctttcgctttcttcccttcctttctcgccacgttcgccggctttccccgtcaa
gctctaaatcggggctccctttagggttccgatttagtgctttacggcacctcgaccccaaaaaacttgattagggtgatggttcac
gtagtgggccatcgccctgatagacggtttttcgccctttgacgttggagtccacgttctttaatagtggactcttgttccaaactgg
aacaacactcaaccctatctcggtctattcttttgatttataagggattttgccgatttcggcctattggttaaaaaatgagctgatt
taacaaaaatttaacgcgaattaaatattaatccaacgcgtggcatcaaataaaacgaaaggctcagtcgaaagactgggcctttcgt
tttatctgttgtttgtcggtgaacgctctcctgagtaggacaaatccgccgccctagacttaggcgttcggctgcggcgagcggtatc
agctcactcaaaggcggtaatacggttatccacagaatcaggggataacgcaggaaaagaacatgtgagcaaaaggccagcaaaaggccag
gaaccgtaaaaaggccgcgttgctggcgtttttccataggctccgcccccctgacgagcatcacaaaaatcgacgctcaagtcaga
ggtggcgaaacccgacaggactataaagataccaggcgtttccccctggaagctccctcgtgcgctctcctgttccgaccctgccgct
taccggatacctgtccgcctttctcccttcgggaagcgtggcgctttctcatagctcacgctgtaggtatctcagttcggtgtaggtc
gttcgctccaagctgggctgtgtgcacgaaccccccgttcagcccgaccgctgcgccttatccggtaactatcgtcttgagtccaacc

| Sequences |
|---|
| cggtaagacacgacttatcgccactggcagcagccactggtaacaggattagcagagcgaggtatgtaggcggtgctacagagttctt
gaagtggtggcctaactacggctacactagaaggacagtatttggtatctgcgctctgctgaagccagttaccttcggaaaaagagtt
ggtagctcttgatccggcaaacaaaccaccgctggtagcggtggttttttttgtttgcaagcagcagattacgcgcagaaaaaaaggat
ctcaagaagatcctttgatcttttctacggggtctgacgctcagtggaacgaaaactcacgttaagggattttggtcatggctagtgc
ttggattctcaccaataaaaaacgcccggcggcaaccgagcgttctgaacaaatccagatggagttctgaggtcattactggatctat
caacaggagtccaagccaattctcgaaccccagagtcccgctcagaagaactcgtcaagaaggcgatagaaggcgatgcgctgcgaat
cgggagcggcgataccgtaaagcacgaggaagcggtcagcccattcgccgccaagctcttcagcaatatcacgggtagccaacgctat
gtcctgatagcggtccgccacacccagccggccacagtcgatgaatccagaaaagcggccattttccaccatgatattcggcaagcag
gcatcgccgtgggtcacgacgagatcctcgccgtcgggcatacgcgccttgagcctggcgaacagttcggctggcgcgagcccctgat
gctcttcgtccagatcatcctgatcgacaagaccggcttccatccgagtacgtgctcgctcgatgcgatgtttcgcttggtggtcgaa
tgggcaggtagccggatcaagcgtatgcagccgccgcattgcatcagccatgatggatacttctcggcaggagcaaggtgagatgac
aggagatcctgccccggcacttcgcccaatagcagccagtccctttcccgcttcagtgacaacgtcgagcacgcgcgcaaggaacgc
ccgtcgtggccagccacgatagccgcgctgcctcgtcttgcagttcattcagggcaccggacaggtcggtcttgacaaaaagaaccgg
gcgacccctgcgctgacagccggaacacggcggcatcagagcagccgattgtctgttgtgcccagtcatagccgaatagcctctccacc
caagccgccggagaacctgcgtgcaatccatcttgttcaatcatgcgaaacgatcctcatcctgtctcttgatcagatcttgatcccc
tgcgccatcagatccttggcggcaagaaagccatccagtttactttgcagggcttcccaaccttaccagagggcggcccaactggcaa
ttcc |

>pRJK046 [organism = cloning vector] SEQ ID NO: 57
gacgtctgtgcaagtactactgttctgcagtcacttgaattcgatacccagctgggtggagtgcaccaaggagcatgcgaaggaaacg
tttcgcagaagctttccctatcagtgatagagattgacatccctatcagtgatagagatactgagcacatcagcaggacgcactgacc
ggtacccaacagggattcgttaatttaaggaggtctccaaatgggcaacaaccgcccggtgtatattccgcagccgcgcccgccgcat
ccgcgcatttaaccgcggagtatttgtacagaggtacaactcaactaatataaggaggttcaaaatgggcaacaaccgcccggtgtat
attccgcagccgcgcccgccgcatccgcgcatttaaggatcccgagcattggacttggcttgactcctgttgatagatccagtaagdacctca
gaactccatctggatttgttcagaacgctcggttgccgccgggcgttttttattggtgagaatccaagcagtagtcagagctcggact
gcttaagtcgctccatatgctcgttcccgggactacacaattgtccccggcgcagggttgatatctatcgccctagggaccgtctc
gagagcgccctgtagcggcgcattaagcgcggcgggtgtggtggttacgcgcagcgtgaccgctacacttgccagcgccctagcgccc
gctccttcgctttcttccctttctcgccacgttcgccggctttcccgtcaagctctaaatcggggcctccctttaggggttcc
gatttagtgctttacggcacctcgaccccaaaaaacttgattagggtgatggttcacgtagtgggccatcgccctgatagacggtttt
tcgccctttgacgttggagtccacgttctttaatagtggactcttgttccaaactggaacaacactcaaccctatctcggtctattct
tttgatttataaggggattttgccgatttcggcctattggttaaaaaatgagctgatttaacaaaaatttaacgcgaattaaatattaa
tccaacgcgtggcatcaaataaaacgaaaggctcagtcgaaagactgggcctttcgttttatctgttgtttgtcggtgaacgctctcc
tgagtaggacaaatccgccgccctagacttaggcgttcggctgcggcgagcggtatcagctcactcaaaggcggtaatacggttatcc
acagaatcaggggataacgcaggaaagaacatgtgagcaaaaggccagcaaaaggccaggaaccgtaaaaaggccgcgttgctggcgt
ttttccataggctccgcccccctgacgagcatcacaaaaatcgacgctcaagtcagaggtggcgaaacccgacaggactataaagata
ccaggcgtttccccctggaagctccctcgtgcgctctcctgttccgaccctgccgcttaccggatacctgtccgcctttctcccttcg
ggaagcgtggcgctttctcatagctcacgctgtaggtatctcagttcggtgtaggtcgttcgctccaagctgggctgtctgcacgaac
ccccgttcagcccgaccgctgcgccttatccggtaactatcgtcttgagtccaacccggtaagacacgacttatcgccactggcagc
agccactggtaacaggattagcagagcgaggtatgtaggcggtgctacagagttcttgaagtggtggcctaactacggctacactaga
aggacagtatttggtatctgcgctctgctgaagccagttaccttcggaaaaagagttggtagctcttgatccggcaaacaaaccaccg
ctggtagcggtggtttttttgtttgcaagcagcagattacgcgcagaaaaaaaggatctcaagaagatcctttgatcttttctacggg
gtctgacgctcagtggaacgaaaactcacgttaagggattttggtcatggctagtgcttggattctcaccaataaaaaacgcccggcg
gcaaccgagcgttctgaacaaatccagatggagttctgaggtcattactggatctatcaacaggagtccaagccaattctcgaacccc
agagtcccgctcagaagaactcgtcaagaaggcgatagaaggcgatgcgctgcgaatcgggagcggcgataccgtaaagcacgaggaa
gcggtcagcccattcgccgccaagctcttcagcaatatcacgggtagccaacgctatgtcctgatagcggtccgccacacccagccgg
ccacagtcgatgaatccagaaaagcggccattttccaccatgatattcggcaagcaggcatcgccgtgggtcacgacgagatcctcgc
cgtcgggcatacgcgccttgagcctggcgaacagttcggctggcgcgagcccctgatgctcttcgtccagatcatcctgatcgacaag
accggcttccatccgagtacgtgctcgctcgatgcgatgtttcgcttggtggtcgaatgggcaggtagccggatcaagcgtatgcagc
cgccgcattgcatcagccatgatggatacttctcggcaggagcaaggtgagatgacaggagatcctgccccggcacttcgcccaata
gcagccagtcccttcccgcttcagtgacaacgtcgagcacagcgcgcaaggaacgcccgtcgtggccagccacgatagccgcgctgc
ctcgtcttgcagttcattcagggcaccggacaggtcggtcttgacaaaaagaaccgggcgacccctgcgctgacagccggaacacggcg
gcatcagagcagccgattgtctgttgtgcccagtcatagccgaatagcctctccacccaagccgccggagaacctgcgtgcaatccat
cttgttcaatcatgcgaaacgatcctcatcctgtctcttgatcagatcttgatccccgcgccatcagatccttggcggcaagaaagc
catccagtttactttgcagggcttcccaaccttaccagagggcggcccaactggcaattcc >pRJK055 [organism = cloning vector] SEQ ID NO: 58
gacgtctgtgcaagtactactgttctgcagtcacttgaattcgatacccagctgggtggagtgcaccaaggagcatgcgaaggaaacg
tttcgcagaagctttccctatcagtgatagagattgacatccctatcagtgatagagatactgagcacatcagcaggacgcactgacc
ggtacccgactaacaactctataaggaggtccataaatgacccgcagcagccgcgcgggcctgcagtttccggtgggccgcgtgcatc
gcctgctgcgcaaagactacaaagacgacgacgacaaataaccgcggagtatttgtacagaggtacaactcaactaatataaggaggt
tcaaaatgacccgcagcagccgcgcgggcctgcagtttccggtgggccgcgtgcatcgcctgctgcgcaaagactacaaagacgacga
cgacaaataaggatcccgagcattggacttggcttgactcctgttgatagatccagtaatgacctcagaactccatctggatttgttcagaac
gctcggttgccgccgggcgttttttattggtgagaatccaagcagtagtcagagctcggactgcttaagtcgctccatatgctcgttc
ccgggactacacaattgtccccggcgcagggttgatatctatcgccctagggaccgtctcgagagaatcaatattaatccaacgcg
tggcatcaaataaaacgaaaggctcagtcgaaagactgggcctttcgttttatctgttgtttgtcggtgaacgctctcctgagtagga
caaatccgccgccctagacttaggcgttcggctgcggcgagcggtatcagctcactcaaaggcggtaatacggttatccacagaatca
ggggataacgcaggaaagaacatgtgagcaaaaggccagcaaaaggccaggaaccgtaaaaaggccgcgttgctggcgtttttccata
ggctccgcccccctgacgagcatcacaaaaatcgacgctcaagtcagaggtggcgaaacccgacaggactataaagataccaggcgtt
tccccctggaagctccctcgtgcgctctcctgttccgaccctgccgcttaccggatacctgtccgcctttctcccttcgggaagcgtg
gcgctttctcatagctcacgctgtaggtatctcagttcggtgtaggtcgttcgctccaagctgggctgtctgcacgaaccccccgttc
agcccgaccgctgcgccttatccggtaactatcgtcttgagtccaacccggtaagacacgacttatcgccactggcagcagccactgg
taacaggattagcagagcgaggtatgtaggcggtgctacagagttcttgaagtggtggcctaactacggctacactagaaggacagta
tttggtatctgcgctctgctgaagccagttaccttcggaaaaagagttggtagctcttgatccggcaaacaaaccaccgctggtagcg
gtggtttttttgtttgcaagcagcagattacgcgcagaaaaaaaggatctcaagaagatcctttgatcttttctacggggtctgacgc
tcagtggaacgaaaactcacgttaagggattttggtcatggctagtgcttggattctcaccaataaaaaacgcccggcggcaaccgag
cgttctgaacaaatccagatggagttctgaggtcattactggatctatcaacaggagtccaagccaattctcgaaccccagagtcccg
ctcagaagaactcgtcaagaaggcgatagaaggcgatgcgctgcgaatcgggagcggcgataccgtaaagcacgaggaagcggtcagc

| Sequences |
|---|
| ccattcgccgccaagctcttcagcaatatcacggggtagccaacgctatgtcctgatagcggtccgccacacccagccggccacagtcg
atgaatccagaaaagcggccatttttccaccatgatattcggcaagcaggcatcgccgtgggtcacgacgagatcctcgccgtcgggca
tacgcgccttgagcctggcgaacagttcggctggcgcgagccctgatgctcttcgtccagatcatcctgatcgacaagaccggcttc
catccgagtacgtgctcgctcgatgcgatgtttcgcttggtggtcgaatgggcaggtagccggatcaagcgtatgcagccgccgcatt
gcatcagccatgatggatactttctcggcaggagcaaggtgagatgacaggagatcctgccccggcacttcgcccaatagcagccagt
cccttcccgcttcagtgacaacgtcgagcacagccgcgcaaggaacgcccgtcgtggccagccacgatagccgcgctgcctcgtcttg
cagttcattcagggcaccggacaggtcggtcttgacaaaaagaaccgggcgaccctgcgctgacagccggaacacggcggcatcagag
cagccgattgtctgttgtgcccagtcatagccgaatagcctctccacccaagccgccggagaacctgcgtgcaatccatcttgttcaa
tcatgcgaaacgatcctcatcctgtctcttgatcagatcttgatccctgcgccatcagatccttggcggcaagaaagccatccagtt
tactttgcagggcttcccaaccttaccagagggcggcccaactggcaattcc |

>pRJK062 [organism = cloning vector] SEQ ID NO: 59
gacgtctgtgcaagtactactgttctgcagtcacttgaattcgatacccagctgggtggagtgcaccaaggagcatgcgaaggaaacg
tttcgcagaagcttccctatcagtgatagagattgacatccctatcagtgatagagatactgagcacatcagcaggacgcactgacc
ggtacctaaaagaggagactcacccttaaggaggtataagatggcgctgtggaaaaacatgctgaaaggcattggcaaactggcgggc
aaagcggcgctgggcgcggtgaaaaaactggtgggcgcgagccctaaccgcggagtattttgtacacaagtacagaggagtaaggagg
taaagtatggcgctgtggaaaaacatgctgaaaggcattggcaaactggcgggcaaagcggcgctgggcgcggtgaaaaaactggtgg
gcgcggaaagctaaggatcccgagaattggcttggactcctgttgatagatccagtaatgacctcagaactccatctggatttgttca
gaacgctcggttgccgccgggcgttttttattggtgagaatccaagcagtagtcagagctcggactgcttaagtcgctccatatgctc
gttcccgggactacacaattgtcccccggcgccagggttgattctatcgccctaggggaccgtctcgagagaatcaatattaatccaa
cgcgtggcatcaaataaaacgaaaggctcagtcgaaagactgggcctttcgttttatctgttgtttgtcggtgaacgctctcctgagt
aggacaaatccgccgccctagacttaggcgttcggctgcggagcggtatcagctcactcaaaggcggtaatacggttatccacaga
atcagggataacgcaggaaagaacatgtgagcaaaaggccagcaaaaggccaggaaccgtaaaaaggccgcgttgctggcgtttttc
cataggctccgcccccctgacgagcatcacaaaaatcgacgctcaagtcagaggtggcgaaacccgacaggactataaagataccagg
cgtttccccctggaagctccctcgtgcgctctcctgttccgaccctgccgcttaccggatacctgtccgcctttctcccttcgggaag
cgtggcgctttctcatagctcacgctgtaggtatctcagttcggtgtaggtcgttcgctccaagctgggctgtctgcacgaacccccc
gttcagcccgaccgctgcgccttatccggtaactatcgtcttgagtccaacccggtaagacacgacttatcgccactggcagcagcca
ctggtaacaggattagcagagcgaggtatgtaggcggtgctacagagttcttgaagtggtggcctaactacggctacactagaaggac
agtatttggtatctgcgctctgctgaagccagttaccttcggaaaaagagttggtagctcttgatccggcaaacaaaccaccgctggt
agcggtggtttttttgtttgcaagcagcagattacgcgcagaaaaaaaggatctcaagaagatcctttgatcttttctacggggtctg
acgctcagtggaacgaaaactcacgttaagggattttggtcatggctagtgcttggattctcaccaataaaaaacgcccggcggcaac
cgagcgttctgcaacaaatccagatggagttctgaggtcattactggatctatcaacaggagtccaagccaattctcgaacccagagt
cccgctcagaagaactcgtcaagaagtcgatagaaggcgatagcgctgcgaatcgggagcggcgataccgtaaagcacgaggaagcggt
cagcccattcgccgccaagctcttcagcaatatcacggggtagccaacgctatgtcctgatagcggtccgccacacccagccggccaca
gtcgatgaatccagaaaagcggccatttttccaccatgatattcggcaagcaggcatcgccgtgggtcacgacgagatcctcgccgtcg
ggcatacgcgccttgagcctggcgaacagttcggctggcgcgagccctgatgctcttcgtccagatcatcctgatcgacaagaccgg
cttccatccgagtacgtgctcgctcgatgcgatgtttcgcttggtggtcgaatgggcaggtagccggatcaagcgtatgcagccgccg
cattgcatcagccatgatggatactttctcggcaggagcaaggtgagatgacaggagatcctgccccggcacttcgcccaatagcagc
cagtcccttcccgcttcagtgacaacgtcgagcacagccgcgcaaggaacgcccgtcgtggccagccacgatagccgcgctgcctcgt
cttgcagttcattcagggcaccggacaggtcggtcttgacaaaaagaaccgggcgaccctgcgctgacagccggaacacggcggcatc
agagccgattgtctgttgtgcccagtcatagccgaatagcctctccacccaagccgccggagaacctgcgtgcaatccatcttgt
tcaatcatgcgaaacgatcctcatcctgtctcttgatcagatcttgatcccctgcgccatcagatccttggcggcaagaaagccatcc
agtttactttgcagggcttcccaaccttaccagagggcggcccaactggcaattcc >pRJK070 [organism = cloning vector] SEQ ID NO: 60
gacgtctgtgcaagtactactgttctgcagtcacttgaattcgatacccagctgggtggagtgcaccaaggagcatgcgaaggaaacg
tttcgcagaagcttccctatcagtgatagagattgacatccctatcagtgatagagatactgagcacatcagcaggacgcactgacc
ggtaccaacggtaagaggcataatttaaggaggtaacacatgggctggggcagctttttaaaaaagcggcgcatgtgggcaaacatg
tgggcaaagcggcgctgaccccattatctgtaaccgccggagtattttgtacagatttataaaatcggaatagataaggagtacacatgg
gctggggcagctttttaaaaaagcggcgcatgtgggcaaacatgtgggcaaagcggcgctgaccccattatctgtaaggatcccgaga
attggcttggactcctgttgatagatccagtaatgacctcagaactccatctggatttgttcagaacgctcggttgccgccgggcgtt
ttttattggtgagaatccaagcagtagtcagagctcggactgcttaagtcgctccatatgctcgttcccgggactacacaattgtccc
ccggcgccagggttgattctatcgccctaggggaccgtctcgagagaatcaatattaatccaacgcgtggcatcaaataaaacgaaag
gctcagtcgaaagactgggcctttcgttttatctgttgtttgtcggtgaacgctctcctgagtaggacaaatccgccgccctagactt
aggcgttcggctgcggagcggtatcagctcactcaaaggcggtaatacggttatccacagaatcagggataacgcaggaaagaac
atgtgagcaaaaggccagcaaaaggccaggaaccgtaaaaaggccgcgttgctggcgtttttccataggctccgcccccctgacgagc
atcacaaaaatcgacgctcaagtcagaggtggcgaaacccgacaggactataaagataccaggcgtttccccctggaagctccctcgt
gcgctctcctgttccgaccctgccgcttaccggatacctgtccgcctttctcccttcgggaagcgtggcgctttctcatagctcacgc
tgtaggtatctcagttcggtgtaggtcgttcgctccaagctgggctgtctgcacgaaccccccgttcagcccgaccgctgcgcccttat
ccggtaactatcgtcttgagtccaacccggtaagacacgacttatcgccactggcagcagccactggtaacaggattagcagagcgag
gtatgtaggcggtgctacagagttcttgaagtggtggcctaactacggctacactagaaggacagtatttggtatctgcgctctgctg
aagccagttaccttcggaaaaagagttggtagctcttgatccggcaaacaaaccaccgctggtggttttttgtttgcaagc
agcagattacgcgcagaaaaaaaggatctcaagaagatcctttgatcttttctacggggtctgacgctcagtggaacgaaaactcacg
ttaagggattttggtcatggctagtgcttggattctcaccaataaaaaacgcccggcggcaaccgagcgttctgaacaaatccagatg
gagttctgaggtcattactggatctatcaacaggagtccaagccaattctcgaacccagagtcccgctcagaagaactcgtcaagaa
ggcgatagaaggcgatgcgctgcgaatcgggagcggcgataccgtaaagcacgaggaagcggtcagcccattcgccgccaagctcttc
agcaatatcacggggtagccaacgctatgtcctgatagcggtccgccacacccagccggccacagtcgatgaatccagaaaagcggcca
ttttccaccatgatattcggcaagcaggcatcgccgtgggtcacgacgagatcctcgccgtcgggcatacgcgccttgagcctggcga
acagttcggctggcgcgagccctgatgctcttcgtccagatcatcctgatcgacaagaccggcttccatccgagtacgtgctcgctc
gatgcgatgtttcgcttggtggtcgaatgggcaggtagccggatcaagcgtatgcagccgccgcattgcatcagccatgatggatact
ttctcggcaggagcaaggtgagatgacaggagatcctgccccggcacttcgcccaatagcagccagtcccttcccgcttcagtgacaa
cgtcgagcacagccgcgcaaggaacgcccgtcgtggccagccacgatagccgcgctgcctcgtcttgcagttcattcagggcaccgga
caggtcggtcttgacaaaaagaaccgggcgaccctgcgctgacagccggaacacggcggcatcagagccgattgtctgttgtgccc
cagtcatagccgaatagcctctccacccaagccgccggagaacctgcgtgcaatccatcttgttcaatcatgcgaaacgatcctcatc
ctgtctcttgatcagatcttgatcccctgcgccatcagatccttggcggcaagaaagccatccagtttactttgcagggcttcccaac
cttaccagagggcggcccaactggcaattcc

| Sequences |
|---|
| >pPh037 [organism = cloning vector] SEQ ID NO: 61<br>gacgtctgtgcaagtactactgttctgcagtcacttgaattcgatacccagctgggtggagtgcaccaaggagcatgcgaaggaaacg<br>tttcgcagaagctttccctatcagtgatagagattgacatccctatcagtgatagagatactgagcacatcagcaggacgcactgacc<br>ggtaccctataagttacacaacataaggaggaatataatgcgtcgtcgtccgcgtccgcgtacctgccgcgtccgcgtccgccgccg<br>ttcttcccgccgcgtctgccgccgcgtatcccgccgggtttcccgccgcgtttcccgccgcgtttccgtaaccgcggagtatttgta<br>cattctatcaaagtatcataaggaggagaataatgcgtcgtcgtccgcgtccgccgtacctgccgcgtccgcgtccgccgccgttctt<br>cccgccgcgtctgccgccgcgtatcccgccgggtttcccgccgcgtttcccgccgcgtttccgtaaggatcccgagaattggcttgg<br>actcctgttgatagatccagtaatgacctcagaactccatctggatttgttcagaacgctcggttgccgccgggcgtttttttattggt<br>gagaatccaagcagtagtcagagctcggactgcttaagtcgctccatatgctcgttcccgggactacacaattgtccccggcgccag<br>ggttgatatctatcgccctagggaccgtctcgagagcgccctgtagcggcgcattaagcgcggcgggtgtggtggttacgcgcagcgt<br>gaccgctacacttgccagcgccctagcgcccgctccttcgctttcttccctccttctcgccacgttcgccggctttcccgtcaa<br>gctctaaatcggggctcccttagggttcgatttagtgcttacggcacctcgaccccaaaaaacttgattagggtgatggttcac<br>gtagtgggccatcgccctgatagacggttttcgccctttgacgttggagtccacgttcttttaatagtggactcttgttccaaactgg<br>aacaacactcaaccctatctcggtctattctttgatttataagggattttgccgatttcggcctattggttaaaaaatgagctgatt<br>taacaaaaatttaacgcgaattaaatattaatccaacgcgtggcatcaaataaaacgaaaggctcagtcgaaagactgggcctttcgt<br>tttatctgttgtttgtcggtgaacgctctcctgagtaggacaaatccgccgccctagacttaggcgttcggctgcggcgagcggtatc<br>agctcactcaaaggcggtaatacggttatccacagaatcaggggataacgcaggaaagaacatgtgagcaaaaggccagcaaaaggcc<br>aggaaccgtaaaaaggccgcgttgctggcgtttttccataggctccgcccccctgacgagcatcacaaaaatcgacgctcaagtcaga<br>ggtggcgaaacccgacaggactataaagataccaggcgtttccccctggaagctccctcgtgcgctctcctgttccgaccctgccgct<br>taccggatacctgtccgcctttctcccttcgggaagcgtggcgctttctcatagctcacgctgtaggtatctcagttcggtgtaggtc<br>gttcgctccaagctgggctgtctgcacgaaccccccgttcagcccgaccgctgcgccttatccggtaactatcgtcttgagtccaacc<br>cggtaagacacgacttatcgccactggcagcagccactggtaacaggattagcagagcgaggtatgtaggcggtgctacagagttctt<br>gaagtggtggcctaactacggctacactagaaggacagtatttggtatctgcgctctgctgaagccagttaccttcggaaaaagagtt<br>ggtagctcttgatccggcaaacaaaccaccgctggtagcggtggtttttttgtttgcaagcagcagattacgcgcagaaaaaaaggat<br>ctcaagaagatcctttgatcttttctacggggtctgacgctcagtggaacgaaaactcacgttaagggattttggtcatggctagtgc<br>ttggattctcaccaataaaaaacgcccggcggcaaccgagcgttctgaacaaatccagatggagttctgaggtcattactggatctat<br>caacaggagtccaagccaattctcgaaccccagagtcccgctcagaagaactcgtcaagaaggcgatagaaggcgatgcgctgcgaat<br>cgggagcggcgataccgtaaagcacgaggaagcggtcagcccattcgccgccaagctcttcagcaatatcacgggtagccaacgctat<br>gtcctgatagcggtccgccacacccagccggccacagtcgatgaatccagaaaagcggccattttccaccatgatattcggcaagcag<br>gcatcgccgtgggtcacgacgagatcctcgccgtcgggcatacgcgccttgagcctggcgaacagttcggctggcgcgagccctgat<br>gctcttcgtccagatcatcctgatcgacaagaccggcttccatccgagtacgtgctcgctcgatgcgatgtttcgcttggtggtcgaa<br>tgggcaggtagccggatcaagcgtatgcagccgccgcattgcatcagccatgatggatacttttctcggcaggagcaaggtgagatgac<br>aggagatcctgccccggcacttcgcccaatagcagccagtcccttcccgcttcagtgacaacgtcgagcacagctgcgcaaggaacgc<br>ccgtcgtggccagccacgatagccgcgctgcctcgtcttgcagttcattcagggcaccggacaggtcggtcttgacaaaaagaaccgg<br>gcgacccgctgcgctgacagccggaacacggcggcatcagagcagccgattgtctgttgtgcccagtcatagccgaatagcctctccacc<br>caagccgccggagaacctgcgtgcaatccatcttgttcaatcatgcgaaacgatcctcatcctgtctcttgatcagatcttgatcccc<br>tgcgccatcagatccttggcggcaagaaagccatccagtttactttgcagggcttcccaaccttaccagagggcgggcccaactggcaa<br>ttcc |
| >pPh046 [organism = cloning vector] SEQ ID NO: 62<br>gacgtctgtgcaagtactactgttctgcagtcacttgaattcgatacccagctgggtggagtgcaccaaggagcatgcgaaggaaacg<br>tttcgcagaagctttccctatcagtgatagagattgacatccctatcagtgatagagatactgagcacatcagcaggacgcactgacc<br>ggtacccaacagggattcgttaatttaaggaggtctccaaatgggcaacaaccgccggtgtatattccgcagccgcgcccgccgcat<br>ccgcgcatttaaccgcggagtatttgtacagaggtacaactcaactaataataaggaggttcaaaatgggcaacaaccgccggtgtat<br>attccgcagccgcgcccgccgcatccgcgcatttaaggatccccgagaattggcttggactcctgttgatagatccagtaatgacctca<br>gaactccatctggatttgttcagaacgctcggttgccgcggggcgtttttattggtgagaatccaagcagtagtcagagctcggact<br>gcttaagtcgctccatatgctcgttcccgggactacacaattgtccccggcgccagggttgatatctatcgccctagggaccgtctc<br>gagagcgccctgtagcggcgcattaagcgcggcgggtgtggtggttacgcgcagcgtgaccgctacacttgccagcgccctagcgccc<br>gctccttcgctttcttcccttcctttctcgccacgttcgccggctttccccgtcaaagctctaaatcggggctcccttagggttccc<br>gatttagtgctttacggcacctcgaccccaaaaaacttgattagggtgatggttcacgtagtgggccatcgccctgatagacggttttt<br>cgccctttgacgttggagtccacgttctttaatagtggactcttgttccaaactggaacaacactcaaccctatctcggtctattct<br>tttgatttataagggattttgccgatttcggcctattggttaaaaaatgagctgatttaacaaaaatttaacgcgaattaaatattaa<br>tccaacgcgtggcatcaaataaaacgaaaggctcagtcgaaagactgggcctttcgttttatctgttgtttgtcggtgaacgctctcc<br>tgagtaggacaaatccgccgccctagacttaggcgttcggctgcggcgagcggtatcagctcactcaaaggcggtaatacggttatcc<br>acagaatcaggggataacgcaggaaagaacatgtgagcaaaaggccagcaaaaggccaggaaccgtaaaaaggccgcgttgctggcgt<br>ttttccataggctccgcccccctgacgagcatcacaaaaatcgacgctcaagtcagaggtggcgaaacccgacaggactataaagata<br>ccaggcgtttccccctggaagctccctcgtgcgctctcctgttccgaccctgccgcttaccggatacctgtccgcctttctcccttcg<br>ggaagcgtggcgctttctcatagctcacgctgtaggtatctcagttcggtgtaggtcgttcgctccaagctgggctgtctgcacgaac<br>cccccgttcagcccgaccgctgcgccttatccggtaactatcgtcttgagtccaacccggtaagacacgacttatcgccactggcagc<br>agccactggtaacaggattagcagagcgaggtatgtaggcggtgctacagagttcttgaagtggtggcctaactacggctacactaga<br>aggacagtatttggtatctgcgctctgctgaagccagttaccttcggaaaaagagttggtagctcttgatccggcaaacaaaccaccg<br>ctggtagcggtggtttttttgtttgcaagcagcagattacgcgcagaaaaaaaggatctcaagaagatcctttgatcttttctacggg<br>gtctgacgctcagtggaacgaaaactcacgttaagggattttggtcatggctagtgcttggattctcaccaataaaaaacgcccggcg<br>gcaaccgagcgttctgaacaaatccagatggagttctgaggtcattactggatctatcaacaggagtccaagccaattctcgaaccc<br>cagagtcccgctcagaagaactcgtcaagaaggcgatagaaggcgatgcgctgcgaatcgggagcggcgataccgtaaagcacgaggaa<br>gcggtcagcccattcgccgccaagctcttcagcaatatcacgggtagccaacgctatgtcctgatagcggtccgccacacccagccgg<br>ccacagtcgatgaatccagaaaagcggccattttccaccatgatattcggcaagcaggcatcgccgtgggtcacgacgagatcctcgc<br>cgtcgggcatacgcgccttgagcctggcgaacagttcggctggcgcgagccctgatgctcttcgtccagatcatcctgatcgacaag<br>accggcttccatccgagtacgtgctcgctcgatgcgatgtttcgcttggtggtcgaatgggcaggtagccggatcaagcgtatgcagc<br>cgccgcattgcatcagccatgatggatacttttctcggcaggagcaaggtgagatgacaggagatcctgccccggcacttcgcccaata<br>gcagccagtcccttcccgcttcagtgacaacgtcgagcacagctgcgcaaggaacgcccgtcgtggccagccacgatagccgcgctgc<br>ctcgtcttgcagttcattcagggcaccggacaggtcggtcttgacaaaaagaaccgggcgacccgctgcgctgacagccggaacacggcg<br>gcatcagagcagccgattgtctgttgtgcccagtcatagccgaatagcctctccacccaagccgccggagaacctgcgtgcaatccat<br>cttgttcaatcatgcgaaacgatcctcatcctgtctcttgatcagatcttgatccccgcgccatcagatccttggcggcaagaaagc<br>catccagtttactttgcagggcttcccaaccttaccagagggcgggcccaactggcaattcc |

Sequences

>pPh079 [organism = cloning vector] SEQ ID NO: 63
gacgtctgtgcaagtactactgttctgcagtccctatcagtgatagagattgacatccctatcagtgatagagatactgagcacatca
gcaggacgcactgaccggtaccctataagttacacaacataaggaggaatataatgcgtcgtcgtccgcgtccgccgtacctgccgcg
tccgcgtccgccgccgttcttcccgccgcgtctgccgccgcgtatcccgccgggtttcccgccgcgtttcccgccgcgtttcccgtaa
ccgcggagtatttgtacattctatcaaagtatcataaggaggagaataatgcgtcgtcgtccgcgtccgccgtacctgccgcgtccgc
gtccgccgccgttcttcccgccgcgtctgccgccgcgtatcccgccgggtttcccgccgcgtttcccgccgcgtttcccgtaaggatc
ccgagaattggcttggactcctgttgatagatccagtaatgacctcagaactccatctggatttgttcagaacgctcggttgccgccg
ggcgttttttattggtgagaatccaagcagtagtcagaattcgatacccagctgggtggagtgcaccaaggagcatgcgaaggaaacg
tttcgcagaagctttccctatcagtgatagagattgacatccctatcagtgatagagatactgagcacatcagcaggacgcactgacc
ggtacccaacagggattcgttaatttaaggaggtctccaaatgggcaacaaccgccggtgtatattccgcagccgcgcccgccgcat
ccgcgcatttaaccgcggagtatttgtacagaggtacaactcaactaatataaggaggttcaaaatgggcaacaaccgcccggtgtat
attccgcagccgcgcccgccgcatccgcgcatttaaggatcccgagaattggcttggactcctgttgatagatccagtaatgacctca
gaactccatctggatttgttcagaacgctcggttgccgccgggcgttttttattggtgagaatccaagcagtagtcagagctcggact
gcttaagtcgctccatatgctcgttcccgggactacacaattgtccccggcgcaggggttgatatctatcgccctagggaccgtctc
gagagcgccctgtagccgccgcattaagcgcggcgggtgtggtggttacgcgcagcgtgaccgctacactgccagcgccctagcgcg
gctccttcgctttcttcccttcctttctcgcacgttcgccggcttccccgtcaagctctaaatcggggcgtccctttagggttcc
gatttagtgcttacggcacctcgaccccaaaaaacttgattagggtgatggttcacgtagtgggccatcgccctgatagacggtttt
tcgcccttttgacgttggagtccacgttctttaatagtggactcttgttccaaactggaacaacactcaaccctatctcggtctattct
tttgatttataagggattttgccgatttcggcctattggttaaaaaaatgagctgatttaacaaaaatttaacgcgaattaaatattaa
tccaacgcgtggcatcaaataaaacgaaaggctcagtcgaaagactgggcctttcgttttatctgttgtttgtcggtgaacgctctcc
tgagtaggacaaatccgccgccctagacttaggcgttcggctgcggagcggtatcagctcactcaaaggcggtaatacggttatcc
acagaatcaggggataacgcaggaaagaacatgtgagcaaaaggccagcaaaaggccaggaaccgtaaaaaggccgcgttgctggcgt
ttttccataggctccgcccccctgacgagcatcacaaaaatcgacgctcaagtcagaggtggcgaaacccgacaggactataaagata
ccaggcgtttccccctggaagctccctcgtgcgctctcctgttccgaccctgccgcttaccggatacctgtccgcctttctcccttcg
ggaagcgtggcgctttctcatagctcacgctgtaggtatctcagttcggtgtaggtcgttcgctccaagctgggctgtctgcacgaac
cccccgttcagcccgaccgctgcgccttatccggtaactatcgtcttgagtccaacccggtaagacacgacttatcgccactggcagc
agccactggtaacaggattagcagagcgaggtatgtaggcggtgctacagagttcttgaagtggtggcctaactacggctacactaga
aggacagtatttggtatctgcgctctgctgaagccagttaccttcggaaaaagagttggtagctcttgatccggcaaacaaaccaccg
ctggtagcggtggtttttttgtttgcaagcagcagattacgcgcagaaaaaaaggatctcaagaagatcctttgatcttttctacggg
gtctgacgctcagtggaacgaaaactcacgttaagggattttggtcatgctagtgcttggattctcaccaataaaaaacgcccggcg
gcaaccgagcgttctgaacaaatccagatggagttctgaggtcattactggatctcaacaggagtccaagccaattctcgaacccc
agagtcccgctcagaagaactcgtcaagaaggcgatagaaggcgatgcgctgcgaatcgggagcggcgataccgtaaagcacgaggaa
gcggtcagcccattcgccgccaagctcttcagcaatatcacgggtagccaacgctatgtcctgatagcggtccgccacacccagccgg
ccacagtcgatgaatccagaaaagcggccattttccaccatgatattcggcaagcaggcatcgccgtgggtcacgacgagatcctcgc
cgtcgggcatacgcgccttgagcctggcgaacagttcggctggcgcgagcccctgatgctcttcgtccagatcatcctgatcgacaag
accggcttccatccgagtacgtgctcgctcgatgcgatgtttcgcttggtggtcgaatgggcaggtagccggatcaagcgtatgcagc
cgccgcattgcatcagccatgatggatactttctcggcaggacaaggtgagatgacaggagatcctgccccggcacttcgcccaata
gcagccagtcccttcccgcttcagtgacaacgtcgagcacagccgcgcaaggaacgcccgtcgtggccagccacgatagccgcgctgc
ctcgtcttgcagttcattcagggcaccggacaggtcggtcttgacaaaaagaaccgggcgaccctgcgctgacagccggaacacggcg
gcatcagagcagccgattgtctgttgtgcccagtcatagccgaatagcctctccaccaagcgccggagaacctgcgtgcaatccat
cttgttcaatcatgcgaaacgatcctcatcctgtctcttgatcagatcttgatccccctgcgccatcagatcctggcggcaagaaagc
catccagtttactttgcagggcttcccaaccttaccagagggcgccccaactggcaattcc >pPh110 [organism = cloning vector] SEQ ID NO: 64
gacgtctgtgcaagtactactgttctgcagtccctatcagtgatagagattgacatccctatcagtgatagagatactgagcacatca
gcaggacgcactgaccggtaccctataagttacacaacataaggaggaatataatgcgtcgtcgtccgcgtccgccgtacctgccgcg
tccgcgtccgccgccgttcttcccgccgcgtctgccgccgcgtatcccgccgggtttcccgccgcgtttcccgccgcgtttcccgtaa
ccgcggagtatttgtacattctatcaaagtatcataaggaggagaataatgcgtcgtcgtccgcgtccgccgtacctgccgcgtccgc
gtccgccgccgttcttcccgccgcgtctgccgccgcgtatcccgccgggtttcccgccgcgtttcccgccgcgtttcccgtaaggatc
ccgagaattggcttggactcctgttgatagatccagtaatgacctcagaactccatctggatttgttcagaacgctcggttgccgccg
ggcgttttttattggtgagaatccaagcagtagtcagaattcgatacccagctgggtggagtgcaccaaggagcatgcgaaggaaacg
tttcgcagaagctttccctatcagtgatagagattgacatccctatcagtgatagagatactgagcacatcagcaggacgcactgacc
ggtacccaacagggattcgttaatttaaggaggtctccaaatgggcaacaaccgccggtgtatattccgcagccgcgcccgccgcat
ccgcgcatttaaccgcggagtatttgtacagaggtacaactcaactaatataaggaggttcaaaatgggcaacaaccgcccggtgtat
attccgcagccgcgcccgccgcatccgcgcatttaaggatcccgagaattggcttggactcctgttgatagatccagtaatgacctca
gaactccatctggatttgttcagaacgctcggttgccgccgggcgttttttattggtgagaatccaagcagtagtcagagctcggact
gcttaagtccctatcagtgatagagattgacatccctatcagtgatagagatactgagcacatcagcaggacgcactgaccggtaccc
aagaagatagaggaggtaatatacaagagaatgaacaccctgccggatacccatgtcgcgaagcgagccgctgcccgagcccggtga
ccatttggcagaccctgctgacccgcctgctggatcagcattatggcctgaccctgaacgataccccgtttgcggataacgtgtgat
tgaacagcatattgaagcgggcattagcctgtgcgatgcggtgaactttctggtggaaaataaccgcggagtatttgtacaagccta
acggaagtcgactagtaaggagaactaaatgaaccctgccggatacccatgtcgcgaagcgagccgctgcccgagcccggtga
ccatttggcagaccctgctgacccgcctgctggatcagcattatggcctgaccctgaacgataccccgtttgcggataacgtgtgattg
aacagcatattgaagcgggcattagcctgtgcgatgcggtgaactttctggtggaaaataaggcccgagaattggcttggactcc
tgttgatagatccagtaatgacctcagaactccatctggatttgttcagaacgctcggttgccgccgggcgttttttattggtgagaa
tccaagcagtagtcacaattgtccccggcgcaggggttgatatctatcgccctagggaccgtctcgagagcgccctgtagcggcgca
ttaagcgcggcgggtgtggtggttacgcgcagcgtgaccgctacactgccagcgccctcttcgctttcttcccctt
cctttctcgccacgttcgccggctttccccgtcaagctctaaatcggggctcccctttagggttccgatttagtgctttacggcacct
cgaccccaaaaaacttgattagggtgatggttcacgtagtgggccatcgccctgatagacggttttttcgccctttgacgttggagtcc
acgttctttaatagtggactcttgttccaaactggaacaacactcaaccctatctcggtctattcttttgatttataagggattttgc
cgatttcggcctattggttaaaaaatgagctgatttaacaaaaatttaacgcgaattaaatattaatccaacgcgtggcatcaaataa
aacgaaaggctcagtcgaaagactgggcctttcgttttatctgttgtttgtcggtgaacgctctcctgagtaggacaaatccgccgccc
ctagacttaggcgttcggctgcggagcggtatcagctcactcaaaggcggtaatacggttatccacagaatcaggggataacgcag
gaaagaacatgtgagcaaaaggccagcaaaaggccaggaaccgtaaaaaggccgcgttgctggcgtttttccataggctccgccccc
tgacgagcatcacaaaaatcgacgctcaagtcagaggtggcgaaacccgacaggactataaagataccaggcgtttccccctggaagc
tccctcgtgcgctctcctgttccgaccctgccgcttaccggatacctgtccgcctttctcccttcggggaagcgtggcgctttctcata
gctcacgctgtaggtatctcagttcggtgtaggtcgttcgctccaagctgggctgtctgcacgaaccccccgttcagcccgaccgctg -continued

| Sequences |
|---|
| cgccttatccggtaactatcgtcttgagtccaacccggtaagacacgacttatcgccactggcagcagccactggtaacaggattagc
agagcgaggtatgtaggcggtgctacagagttcttgaagtggtggcctaactacggctacactagaaggacagtatttggtatctgcg
ctctgctgaagccagttaccttcggaaaaagagttggtagctcttgatccggcaaacaaaccaccgctggtagcggtggtttttttgt
ttgcaagcagcagattacgcgcagaaaaaaggatctcaagaagatcctttgatcttttctacggggtctgacgctcagtggaacgaa
aactcacgttaagggatttggtcatggctagtgcttggattctcaccaataaaaaacgcccggcggcaaccgagcgttctgaacaaa
tccagatggagttctgaggtcattactggatctatcaacaggagtccaagccaattctcgaaccccagagtcccgctcagaagaactc
gtcaagaaggcgatagaaggcgatgcgctgcgaatcgggagcggcgataccgtaaagcacgaggaagcggtcagcccattcgccgcca
agctcttcagcaatatcacgggtagccaacgctatgtcctgatagcggtccgccacacccagccggccacagtcgatgaatccagaaa
agcggccattttccaccatgatattcggcaagcaggcatcgccgtgggtcacgacgagatcctcgccgtcgggcatacgcgccttgag
cctggcgaacagttcggctggcgcgagcccctgatgctcttcgtccagatcatcctgatcgacaagaccggcttccatccgagtacgt
gctcgctcgatgcgatgtttcgcttggtggtcgaatgggcaggtagccggatcaagcgtatgcagccgccgcattgcatcagccatga
tggatacttctcggcaggagcaaggtgagatgacaggagatcctgccccggcacttcgcccaatagcagccagtcccttcccgcttc
agtgacaacgtcgagcacagccgcgcaaggaacgcccgtcgtggccagccacgatagccgcgctgcctcgtcttgcagttcattcagg
gcaccggacaggtcggtcttgacaaaaagaaccgggcgacccgctgcgctgacagccggaacacggcggcatcagagcagccgattgtct
gttgtgcccagtcatagccgaatagcctctccacccaagccgccggagaacctgcgtgcaatccatcttgttcaatcatgcgaaacga
tcctcatcctgtctcttgatcagatcttgatccctgcgccatcagatccttggcggcaagaaagccatccagtttactttgcagggc
ttcccaaccttaccagagggcggcccaactggcaattcc >pPh112 [organism = cloning vector] SEQ ID NO: 65
gacgtctgtgtgcaagtactactgttctgcagtccctatcagtgatagagattgacatccctatcagtgatagagatactgagcacatca
gcaggacgcactgaccggtaccctataagttacacaacataaggaggaatataatgcgtcgtcgtccgcgtccgccgtacctgccgcg
tccgcgtccgccgccgttcttcccgccgcgtctgccgccgcgtatcccgccgggtttcccgccgcgtttcccgccgcgtttcccgtaa
ccgcggagtatttgtacattctatcaaagtatcataaggaggagaataatgcgtcgtcgtccgcgtccgccgtacctgccgcgtccgc
gtccgccgccgttcttcccgccgcgtctgccgccgcgtatcccgccgggtttcccgccgcgtttcccgccgcgtttcccgtaaggatc
ccgagaattggcttggactcctgttgatagatccagtaatgaccctcagaactccatctggatttgttcagaacgctcggttgccgcg
ggcgttttttattggtgagaatccaagcagtagtcagaattcgatacccagctgggtggagtgcaccaaggagcatgcgaaggaaacg
tttcgcagaagctttccctatcagtgatagagattgacatccctatcagtgatagagatactgagcacatcagcaggacgcactgacc
ggtacccaacagggattcgttaatttaaggaggtctccaaatgggcaacaacgcccggtgtatattccgcagccgcgcccgccgccgcat
ccgcgcattttaaccgcggagtatttgtacagaggtacaactcaactaatataaggaggttcaaaatgggcaacaacgcccggtgtat
attccgcagccgcgcccgccgcatccgcgcatttaaggatcccgagaattggcttggactcctgttgatagatccagtaatgacctca
gaactccatctggatttgttcagaacgctcggttgccgccgggcgttttttattggtgagaatccaagcagtagtcagagctcggact
gcttaagtccctatcagtgatagagattgacatccctatcagtgatagagatactgagcacatcagcaggacgcactgaccggtacct
cacaatcaaatctaaggagttacaaatgaccgcgtatatctgaccgctgaagcggaagcggatctgcgcggcattattcgctataccc
gccgcgaatggggcgcggcgcaggtgcgccgctatattgcgaaactggaacagggcattgcgcgcctggcggcgggcgaaggcccgt
ttaaagatatgagcgaactgtttccggcgctgcgcatggcgcgctgcgaacatcattatgtgttttgcctgccgcgcgcgggcgaacc
ggcgctggtggtggcgattctgcatgaacgcatggatctgatgacccgcctggcggatcgcctgaaaggctaaccgcggagtatttgt
acatacactatattaacctaaaaaggagcgtaacgaatgaccgcgtatattctgaccgctgaagcggaagcggatctgcgcggcatta
ttcgctataccgccgcgaatggggcgcggcgcaggtgcgccgctatattgcgaaactggaacagggcattgcgcgcctggcggcgggg
cgaaggcccgtttaaagatatgagcgaactgtttccggcgctgcgcatggcgcgctgcgaacatcattatgtgttttgcctgccgcgc
gcgggcgaaccggcgctggtggtggcgattctgcatgaacgcatggatctgatgacccgcctggcggatcgcctgaaaggctaaggat
cccgagaattggcttggactcctgttgatagatccagtaatgacctcagaactccatctggatttgttcagaacgctcggttgccgcc
gggcgttttttattggtgagaatccaagcagtagtcacaattgtccccggcgccagggttgatatctatcgccctagggaccgtctc
gagagcgccctgtagcggcgcattaagcgcggcgggtgtggtggttacgcgcagcgtgaccgctacacttgccagcgccctagcgccc
gctccttttcgctttcttcccttcctttctcgccacgttcgccggctttcccgtcaagctctaaatcgggggctcccttagggttcc
gatttagtgctttacggcacctcgaccccaaaaacttgatttagggtgatggttcacgtagtgggccatcgccctgatagacggtttt
tcgcccttgacgttggagtccacgttctttaatagtggactcttgttccaaactggaacaacactcaaccctatctcggtctattct
tttgatttataaggggattttgccgatttcggcctattggttaaaaaatgagctgatttaacaaaaatttaacgcgaattaaatattaa
tccaacgcgtggcatcaaataaaacgaaaggctcagtcgaaagactgggcctttcgttttatctgttgtttgtcggtgaacgctctcc
tgagtaggacaaatccgccgccctagacttaggcgttcggctgcggcgagcggtatcagctcactcaaaggcggtaatacggttatcc
acagaatcaggggataacgcaggaaagaacatgtgagcaaaaggccagcaaaaggccaggaaccgtaaaaaggccgcgttgctggcgt
ttttccataggctccgcccccctgacgagcatcacaaaaatcgacgctcaagtcagaggtggcgaaacccgacaggactataaagata
ccaggcgtttccccctggaagctccctcgtgcgctctcctgttccgaccctgccgcttaccggatacctgtccgcctttctcccttcg
ggaagcgtggcgctttctcatagctcacgctgtaggtatctcagttcggtgtaggtcgttcgctccaagctgggctgtgtgcacgaac
cccccgttcagcccgaccgctgcgccttatccggtaactatcgtcttgagtccaacccggtaagacacgacttatcgccactggcagc
agccactggtaacaggattagcagagcgaggtatgtaggcggtgctacagagttcttgaagtggtggcctaactacggctacactaga
aggacagtatttggtatctgcgctctgctgaagccagttaccttcggaaaaagagttggtagctcttgatccggcaaacaaaccaccg
ctggtagcggtggtttttttgttgcaagcagcagattacgcgcagaaaaaaggatctcaagaagatcctttgatcttttctacggg
gtctgacgctcagtggaacgaaaactcacgttaagggattttggtcatggctagtgcttggattctcaccaataaaaaacgcccggg
gcaaccgagcgttctgaacaaatccagatggagttctgaggtcattactggatctatcaacaggagtccaagccaattctcgaaccc
cagagtcccgctcagaagaactcgtcaagaaggcgatagaaggcgatgcgctgcgaatcgggagcggcgataccgtaaagcacgaggaa
gcggtcagcccattcgccgccaagctcttcagcaatatcacgggtagccaacgctatgtcctgatagcggtccgccacacccagccgg
ccacagtcgatgaatccagaaaagcggccgccatttttccaccatgatattcggcaagcaggcatcgccgtgggtcacgacgagatcctcgc
cgtcgggcatacgcgcttgagcctggcgaacagttcggctggcgcgagcccctgatgctcttcgtccagatcatcctgatcgacaag
accggcttccatccgagtacgtgctcgctcgatgcgatgtttcgcttggtggtcgaatgggcaggtagccggatcaagcgtatgcagc
cgccgcattgcatcagccatgatggatactttctcggcaggagcaaggtgagatgacaggagatcctgccccggcacttcgcccaata
gcagccagtcccttcccgcttcagtgacaacgtcgagcacagccgcgcaaggaacgcccgtcgtggccagccacgatagccgcgctgc
ctcgtcttgcagttcattcagggcaccggacaggtcggtcttgacaaaaagaaccgggcgacccgctgcgctgacagccggaacacggcg
gcatcagagcagccgattgtctgttgtgcccagtcatagccgaatagcctctccacccaagccgccggagaacctgcgtgcaatccat
cttgttcaatcatgcgaaacgatcctcatcctgtctcttgatcagatcttgatccctgcgccatcagatccttggcggcaagaaagc
catccagtttactttgcagggcttcccaaccttaccagagggcggcccaactggcaattcc >pPh113 [organism = cloning vector] SEQ ID NO: 66
gacgtctgtgcaagtactactgttctgcagtccctatcagtgatagagattgacatccctatcagtgatagagatactgagcacatca
gcaggacgcactgaccggtaccctataagttacacaacataaggaggaatataatgcgtcgtcgtccgcgtccgccgtacctgccgcg
tccgcgtccgccgccgttcttcccgccgcgtctgccgccgcgtatcccgccgggtttcccgccgcgtttcccgccgcgtttcccgtaa
ccgcggagtatttgtacattctatcaaagtatcataaggaggagaataatgcgtcgtcgtccgcgtccgccgtacctgccgcgtccgc
gtccgccgccgttcttcccgccgcgtctgccgccgcgtatcccgccgggtttcccgccgcgtttcccgccgcgtttcccgtaaggatc |

Sequences ccgagaattggcttggactcctgttgatagatccagtaatgacctcagaactccatctggatttgttcagaacgctcggttgccgcg
ggcgttttttattggtgagaatccaagcagtagtcagaattcgatacccagctgggtggagtgcaccaaggagcatgcgaaggaaacg
tttcgcagaagctttccctatcagtgatgagattgacatccctatcagtgatagagatactgagcacatcagcaggacgcactgacc
ggtacccaacagggattcgttaatttaaggaggtctccaaatgggcaacaaccgcccggtgtatattccgcagccgcgcccgccgcat
ccgcgcatttaaccgcggagtatttgtacagaggtacaactcaactaatataaggaggttcaaaatgggcaacaaccgcccggtgtat
attccgcagccgcgcccgccgcatccgcgcatttaaggatcccgagaattggcttggactcctgttgatagatccagtaatgacctca
gaactccatctggatttgttcagaacgctcggttgccgcgggcgttttttattggtgagaatccaagcagtagtcagagctcggact
gcttaagtccctatcagtgatagagattgacatccctatcagtgatagagatactgagcacatcagcaggacgcactgaccggtacct
atccatcattaacgaccaaatcaaggaggacgtatgcagtttaaggtttacacctataaaagagagagccgttatcgtctgtttgtgg
atgtacagagtgatattattgacacgcccgggcgacggatggtgatcccctggccagtgcacgtctgctgtcagataaagtctcccg
tgaactttacccggtggtgcatatcggggatgaaagctggcgcatgatgaccaccgatatggccagtgtgccggtctccgttatcggg
gaagaagtggctgatctcagccaccgcgaaaatgacatcaaaaacgccattaacctgatgttctggggaatataaggatcccgagaattggct
tggactcctgttgatagatccagtaatgacctcagaactccatctggatttgttcagaacgctcggttgccgcgggcgttttttatt
ggtgagaatccaagcagtagtcacaattgtccccccggcgccaggagttgatatctatcgccctagggaccgtctcgagagcgccctgta
gcggcgcattaagcgcggcgggtgtggtggttacgcgcagcgtgaccgctacacttgccagcgccctagcgcccgctccttttcgcttt
cttccctccttctcgccacgttcgccggctttccccgtcaagctctaaatcgggggctccctttagggttccgatttagtgctttta
cggcacctcgaccccaaaaaacttgatttagggtgatggttcacgtagtgggccatcgccctgatagacggttttttcgccctttgacgt
tggagtccacgttctttaatagtggactcttgttccaaactggaacaacactcaaccctatctcggtctattcttttgatttataagg
gattttgccgatttcggcctattggttaaaaaatgagctgatttaacaaaaaatttaacgcgaattaaatattaatccaacgcgtggca
tcaaatataacgaaaggctcagtcgaaagactgggcctttcgttttatctgttgtttgtcggtgaacgctctcctgagtaggacaaat
ccgccgcccctagacttaggcgttcggctgcggcgagcggtatcagctcactcaaaggcggtaatacggttatccacagaatcagggga
taacgcaggaaagaacatgtgagcaaaaggccagcaaaaggccaggaaccgtaaaaaggccgcgttgctggcgttttccataggctc
cgcccccctgacgagcatcacaaaaatcgacgctcaagtcagaggtggcgaaacccgacaggactataaagataccaggcgtttccc
ctggaagctccctcgtgcgctctcctgttccgaccctgccgcttaccggatacctgtccgcctttctcccttcgggaagcgtggcgct
ttctcatagctcacgctgtaggtatctcagttcggtgtaggtcgttcgctccaagctgggctgtctgcacgaaccccccgttcagccc
gaccgctgcgccttatccggtaactatcgtcttgagtccaacccggtaagacacgacttatcgccactggcagcagccactggtaaca
ggattagcagagcgaggtatgtaggcggtgctacagagttcttgaagtggtggcctaactacggctacactagaaggacagtatttgg
tatctgcgctctgctgaagccagttaccttcggaaaaagagttggtagctcttgatccggcaaacaaaccaccgctggtagcggtggt
ttttttgtttgcaagcagcagattacgcgcagaaaaaaaggatctcaagaagatccttttgatcttttctacggggtctgacgctcagt
ggaacgaaaactcacgttaagggattttggtcatggctagtgcttggattctcaccaataaaaaacgcccggcggcaaccgagcgttc
tgaacaaatccagatggagttctgaggtcattactggatctatcaacaggagtccaagccaattctcgaaccccagagtcccgctcag
aagaactcgtcaagaaggcgatagaaggcgatgcgctgcgaatcgggagcggcgataccgtaaagcacgaggaagcggtcagcccatt
cgccgccaagctcttcagcaatatcacgggtagccaacgctatgtcctgatagcggtccgccacacccagccggccacagtcgatgaa
tccagaaaagcggccattttccaccatgatattcggcaagcaggcatcgccgtgggtcacgacgagatcctcgccgtcgggcatacgc
gccttgagcctggcgaacagttcggctggcgcgagccctgatgctcttcgtccagatcatcctgatcgacaagaccggcttccatcc
gagtacgtgctcgctcgatgcgatgtttcgcttggtggtcgaatgggcaggtagccggatcaagcgtatgcagccgccgcattgcatc
agccatgatggatacttctccggcaggacaaggtgagatgacaggagatcctgccccggcacttcgcccaatagcagccagtcccttt
cccgcttcagtgacaacgtcgagcacagccgcgcaaggaacgcccgtcgtggccacgatagccgcgctgcctcgtcttgcagtt
cattcagggcaccggacaggtcggtcttgacaaaaagaaccgggcgaccctgcgctgacagccgaacacggcggcatcagagcagcc
gattgtctgttgtgcccagtcatagccgaatagcctctccacccaagccgccggagaacctgcgtgcaatccatcttgttcaatcatg
cgaaacgatcctcatcctgtctcttgatcagatcttgatccctgcgccatcagatccttggcggcaagaaagccatccagtttactt
tgcagggcttcccaaccttaccagagggcgccccaactggcaattcc >pPh115 [organism = cloning vector] SEQ ID NO: 67
gacgtctgtgcaagtactactgttctgcagtccctatcagtgatagagattgacatccctatcagtgatagagatactgagcacatca
gcaggacgcactgaccggtacccataagttacacaacataaggaggaatataatgcgtcgtcgtccgcgtccgccgtacctgccgcg
tccgcgtccgccgcgtcttcccgccgcgtctgccgccgcgtatcccgccgggtttcccgccgcgtttcccgccgcgtttcccgtaa
ccgcggagtatttgtacattctatcaaagtatcataaggaggagaataatgcgtcgtcgtccgcgtccgccgtacctgccgcgtccgc
gtccgccgccgttcttcccgccgcgtctgccgccgcgtatccgccgcgttcccgccgcgtttcccgccgcgttttcccgctaaggatc
ccgagaattggcttggactcctgttgatagatccagtaatgacctcagaactccatctggatttgttcagaacgctcggttgccgcg
ggcgttttttattggtgagaatccaagcagtagtcagaattcgatacccagctgggtggagtgcaccaaggagcatgcgaaggaaacg
tttcgcagaagctttccctatcagtgatagagattgacatccctatcagtgatagagatactgagcacatcagcaggacgcactgacc
ggtacccaacagggattcgttaatttaaggaggtctccaaatgggcaacaaccgcccggtgtatattccgcagccgcgcccgccgcat
ccgcgcatttaaccgcggagtatttgtacagaggtacaactcaactaatataaggaggttcaaaatgggcaacaaccgcccggtgtat
attccgcagccgcgcccgccgcatccgcgcatttaaggatcccgagaattggcttggactcctgttgatagatccagtaatgacctca
gaactccatctggatttgttcagaacgctcggttgccgcgggcgttttttattggtgagaatccaagcagtagtcagagctcggact
gcttaagtccctatcagtgatagagattgacatccctatcagtgatagagatactgagcacatcagcaggacgcactgaccggtacct
atccatcattaacgaccaaatcaaggaggacgtatgcagtttaaggtttacacctataaaagagagagccgttatcgtctgtttgtgg
atgtacagagtgatattattgacacgcccgggcgacggatggtgatcccctggccagtgcacgtctgctgtcagataaagtctcccg
tgaactttacccggtggtgcatatcggggatgaaagctggcgcatgatgaccaccgatatggccagtgtgccggtctccgttatcggg
gaagaagtggctgatctcagccaccgcgaaaatgacatcaaaaacgccattaacctgatgttctggggaatataaggatcccgagaat
tggcttggactcctgttgatagatccagtaatgacctcagaactccatctggatttgttcagaacgctcggttgccgcgggcgtttt
ttattggtgagaatccaagcagtagtcaggcgcctccctatcagtgatagagattgacatccctatcagtgatagagatactgagcac
atcagcaggacgcactgaccggtacctatccatcattaacgaccaaatcaaggaggacgtatgcagtttaaggtttacacctataaaa
gagagagccgttatcgtctgtttgtggatgtacagagtgatattattgacacgcccgggcgacggatggtgatcccctggccagtgc
acgtctgctgtcagataaagtctcccgtgaactttacccggtggtgcatatcggggatgaaagctggcgcatgatgaccaccgatatg
gccagtgtgccggtctccgttatcggggaagaagtggctgatctcagccaccgcgaaaatgacatcaaaaacgccattaacctgatgt
tctggggaatataaggatcccgagaattggcttggactcctgttgatagatccagtaatgacctcagaactccatctggatttgttca
gaacgctcggttgccgccgggcgttttttattggtgagaatccaagcagtagtcacctagggaccgtctcgagagcgccctgtagcgg
cgcattaagcgcggcgggtgtggtggttacgcgcagcgtgaccgctacacttgccagcgccctagcgcccgctccttttcgcttcttc
ccttcctttctcgccacgttcgccggctttccccgtcaagctctaaatcgggggctccctttagggttccgatttagtgctttacggc
acctcgaccccaaaaaacttgatttagggtgatggttcacgtagtgggccatcgccctgatagacggttttttcgccctttgacgttgga
gtccacgttctttaatagtggactcttgttccaaactggaacaacactcaaccctatctcggtctattcttttgatttataagggatt -continued Sequences ttgccgatttcggcctattggttaaaaaatgagctgatttaacaaaaatttaacgcgaattaaatattaatccaacgcgtggcatcaa
ataaaacgaaaggctcagtcgaaagactgggcctttcgttttatctgttgtttgtcggtgaacgctctcctgagtaggacaaatccgc
cgccctagacttaggcgttcggctgcggcgagcggtatcagctcactcaaaggcggtaatacggttatccacagaatcaggggataac
gcaggaaagaacatgtgagcaaaaggccagcaaaaggccaggaaccgtaaaaaggccgcgttgctggcgttttttccataggctccgcc
ccctgacgagcatcacaaaaatcgacgctcaagtcagaggtggcgaaacccgacaggactataaagataccaggcgtttccccctgg
aagctccctcgtgcgctctcctgttccgaccctgccgcttaccggatacctgtccgcctttctcccttcgggaagcgtggcgctttct
catagctcacgctgtaggtatctcagttcggtgtaggtcgttcgctccaagctgggctgtgtgcacgaaccccccgttcagcccgacc
gctgcgccttatccggtaactatcgtcttgagtccaacccggtaagacacgacttatcgccactggcagcagccactggtaacaggat
tagcagagcgaggtatgtaggcggtgctacagagttcttgaagtggtggcctaactacggctacactagaaggacagtatttggtatc
tgcgctctgctgaagccagttaccttcggaaaaagagttggtagctcttgatccggcaaacaaaccaccgctggtagcggtggttttt
ttgtttgcaagcagcagattacgcgcagaaaaaaaggatctcaagaagatcctttgatcttttctacggggtctgacgctcagtggaa
cgaaaactcacgttaaggga ttttggtcatggctagtgcttggattctcaccaataaaaaacgccgggcggcaaccgagcgttctgaa
caaatccagatggagttctgaggtcattactggatctatcaacaggagtccaagccaattctcgaacccagagtcccgctcagaaga
actcgtcaaggaaggcgatagaaggcgatgcgctgcgaatcgggagcggcgataccgtaaagcacgaggaagcggtcagccattcgcc
gccaagctcttcagcaatatcacgggtagccaacgctatgtcctgatagcggtccgccacacccagccggccacagtcgatgaatcca
gaaaagcggccattttccaccatgatattcggcaagcaggcatcgccgtgggtcacgacgagatcctcgccgtcgggcatacgcgcct
tgagcctggcgaacagttcggctggcgcgagcccctgatgctcttcgtccagatcatcctgatcgacaagaccggcttccatccgagt
acgtgctcgctcgatgcgatgtttcgcttggtggtcgaatgggcaggtagccggatcaagcgtatgcagccgccgcattgcatcagcc
atgatggatactttctcggcaggagcaaggtgagatgacaggagatcctgccccggcacttcgcccaatagcagccagtcccttcccg
cttcagtgacaacgtcgagcacagccgcgcaaggaacgcccgtcgtggccagcgacgatagccgcgctgcctcgtcttgcagttcatt
cagggcaccggacaggtcggtcttgacaaaaagaaccgggcgaccctcgcgctgacagccggaacacggcggcatcagagcagccgatt
gtctgttgtgcccagtcatagccgaatagcctctccacccaagccgccggagaacctgcgtgcaatccatcttgttcaatcatgcgaa
acgatcctcatcctgtctcttgatcagatcttgatccctgcgccatcagatccttggcggcaagaaagccatccagtttactttgca
gggcttcccaaccttaccagagggcggcccaactggcaattcc All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. An engineered phagemid that comprises
at least one synthetic genetic circuit, wherein the at least one synthetic genetic circuit comprises two tandem copies each of gene sequences encoding at least two non-lytic antimicrobial peptides (AMPs) and at least one antibacterial toxin protein,
an origin of replication, and
a bacteriophage-packaging signal;
wherein the engineered phagemid does not comprise any gene sequences encoding bacteriophage proteins required for assembly of a bacteriophage particle.

2. The engineered phagemid of claim 1, wherein the origin of replication is an F1 origin of replication.

3. The engineered phagemid of claim 1, wherein the engineered phagemid is an M13-derived phagemid.

4. The engineered phagemid of claim 1, wherein at least one of the gene sequences encoding the at least two non-lytic AMP or at least one antibacterial toxin protein is operably linked to a tetR-repressed $P_{LtetO}$ promoter.

5. The engineered phagemid of claim 1, wherein the genetic circuit further comprises at least one ribosome binding site (RBS).

6. The engineered phagemid of claim 1, wherein the antibacterial toxin protein is selected from the group consisting of CcdB, YeeV, YeeV truncated at the C terminus by 52 residues (YeeV') and ParE.

7. A phagemid particle comprising the engineered phagemid of claim 1.

8. A composition comprising the engineered phagemid of claim 1.

9. A composition comprising the phagemid particle of claim 7.

10. A method of treating a bacterial infection, comprising administering to a subject in need of treatment of a bacterial infection an effective amount of the engineered phagemid of claim 1.

11. A method of treating a bacterial infection, comprising administering to a subject in need of treatment of a bacterial infection an effective amount of the phagemid particle of claim 7.

12. A method of treating a bacterial infection, comprising administering to a subject in need of treatment of a bacterial infection an effective amount of the composition of claim 8.

13. A method of treating a bacterial infection, comprising administering to a subject in need of treatment of a bacterial infection an effective amount of the composition of claim 9.

14. A phagemid system comprising
the engineered phagemid of claim 1; and
a plasmid comprising a phagemid helper system that expresses bacteriophage proteins required for assembly of a bacteriophage particle, wherein the plasmid is not packaged in the bacteriophage particle.

15. A bacterial cell comprising the phagemid system of claim 14.

16. A method, comprising transforming a bacterial cell with the phagemid system of claim 14.

17. The method of claim 16 further comprising isolating phagemid particles secreted by the bacterial cell.

18. The method of claim 17 further comprising delivering the isolated phagemid particles to a target bacterial cell.

* * * * *